(12) United States Patent
Huntington et al.

(10) Patent No.: US 9,982,035 B2
(45) Date of Patent: May 29, 2018

(54) MODIFIED SERPINS FOR THE TREATMENT OF BLEEDING DISORDERS

(71) Applicant: Cambridge Enterprise Limited, Cambridge (GB)

(72) Inventors: James Andrew Huntington, Cambridge (GB); Stéphanie Polderdijk, Cambridge (GB); Trevor Baglin, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days. days.

(21) Appl. No.: 15/103,420

(22) PCT Filed: Dec. 15, 2014

(86) PCT No.: PCT/EP2014/077783
§ 371 (c)(1),
(2) Date: Jun. 10, 2016

(87) PCT Pub. No.: WO2015/086854
PCT Pub. Date: Jun. 18, 2015

(65) Prior Publication Data
US 2016/0311887 A1    Oct. 27, 2016

(30) Foreign Application Priority Data
Dec. 13, 2013 (GB) .................................. 1322091.8

(51) Int. Cl.
| | |
|---|---|
| *A61K 38/36* | (2006.01) |
| *A61P 7/02* | (2006.01) |
| *C07K 14/745* | (2006.01) |
| *C07K 14/81* | (2006.01) |
| *A61L 26/00* | (2006.01) |
| *A61K 38/00* | (2006.01) |

(52) U.S. Cl.
CPC ...... *C07K 14/8121* (2013.01); *A61L 26/0047* (2013.01); *C07K 14/8125* (2013.01); *A61K 38/00* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,711,848 A | 12/1987 | Insley et al. | |
| 4,973,668 A | 11/1990 | Jallat et al. | |
| 5,612,194 A | 3/1997 | Rubin et al. | |
| 6,566,493 B1 | 5/2003 | Butenas et al. | |
| 6,753,164 B2 | 6/2004 | Ni et al. | |
| 6,924,267 B2 | 8/2005 | Daemen et al. | |
| 7,265,220 B2 | 9/2007 | De Nanteuil et al. | |
| 8,106,002 B2 | 1/2012 | Suzuki | |
| 8,153,766 B2 | 4/2012 | Xu et al. | |
| 8,183,345 B2 | 5/2012 | Fay et al. | |
| 8,338,571 B2 | 12/2012 | Fay et al. | |
| 8,557,961 B2* | 10/2013 | Silverman ............ | C07K 16/244 530/333 |
| 8,741,844 B2 | 6/2014 | Borgel born Botbol et al. | |
| 9,012,606 B2* | 4/2015 | Chung ............... | C07K 14/8125 530/350 |
| 9,072,722 B2 | 7/2015 | Fay et al. | |
| 9,127,072 B2 | 9/2015 | Xu et al. | |
| 9,127,274 B2 | 9/2015 | Akinc et al. | |
| 9,376,680 B2 | 6/2016 | Akinc et al. | |
| 2009/0170760 A1 | 7/2009 | Suzuki | |
| 2010/0333236 A1* | 12/2010 | Van Breusegem | C12N 15/8286 800/298 |
| 2011/0288005 A1* | 11/2011 | Silverman .......... | C07K 14/8125 514/1.8 |

FOREIGN PATENT DOCUMENTS

| | | | |
|---|---|---|---|
| EP | 0280135 | A2 | 8/1988 |
| EP | 1567199 | A2 | 8/2005 |
| EP | 2081589 | A2 | 7/2009 |
| EP | 2175877 | A1 | 4/2010 |
| EP | 2205638 | A2 | 7/2010 |
| EP | 2209908 | A1 | 7/2010 |
| EP | 2841443 | A2 | 3/2015 |
| JP | 2002010783 | A | 1/2002 |
| JP | 2003039063 | A | 4/2003 |
| WO | WO-9100291 | A1 | 1/1991 |
| WO | WO-9528422 | A1 | 10/1995 |
| WO | WO-2003/039585 | A1 | 5/2003 |
| WO | WO-2004/056309 | A2 | 7/2004 |
| WO | WO-2006/090282 | A2 | 8/2006 |

(Continued)

OTHER PUBLICATIONS

Richer et al. The Spn4 gene of *Drosohpila* encodes a potent furin-directed secretory pathway serpin. PNAS, 2004. vol. 101, No. 29, pp. 10560-10565.*
Jiang et al. Three Pairs of Protease-Serpin Complexes Cooperatively Regulate the Insect Innate Immune Responses. The Journal of Biological Chemistry, 2009. vol. 284, No. 51, pp. 35652-35658.*
Bertina, R.M. et al., Mutation in blood coagulation factor V associated with resistance to activated protein C, Nature, 369(6475):64-67 (1994).
Brummel-Ziedins, K.E. et al., Activated protein C inhibitor for correction of thrombin generation in hemophilia A blood and plasma, Journal of Thrombosis and Haemostasis, 9(11):2262-2267 (2011).

(Continued)

*Primary Examiner* — Marcela M Cordero Garcia
(74) *Attorney, Agent, or Firm* — Choate, Hall & Stewart LLP; Charles E. Lyon; Robert N. Sahr

(57) ABSTRACT

This invention relates pro-coagulant serpin molecules engineered by modification of the P4, P2, P1 and/or P1' residues within the reactive center loop (RCL) to display increased specificity for anticoagulant proteases. These modified serpin molecules may be useful in therapy, for example as pro-coagulants for the treatment of bleeding.

24 Claims, 32 Drawing Sheets

(56) References Cited

FOREIGN PATENT DOCUMENTS

| WO | WO-2008/045148 A2 | 4/2008 | |
|---|---|---|---|
| WO | WO-2008/059009 A2 | 5/2008 | |
| WO | WO-2008/059041 A2 | 5/2008 | |
| WO | WO-2008/059043 A2 | 5/2008 | |
| WO | WO-2009/013251 A1 | 1/2009 | |
| WO | WO-2009/015446 A2 | 2/2009 | |
| WO | WO-2009/055669 A2 | 4/2009 | |
| WO | WO2010123290 * | 10/2010 | ............ C07K 19/00 |
| WO | WO 2013/163430 A2 | 10/2013 | |
| WO | WO-2014/184794 A1 | 11/2014 | |

OTHER PUBLICATIONS

Butenas, S. et al., Peptidomimetic inhibitors for activated protein C: implications for hemophilia management, Journal of Thrombosis and Haemostasis, 4(11):2411-2416 (2006).

De Nanteuil, G. et al., Low Molecular Weight Activated Protein C Inhibitors as a Potential Treatment for Hemophilic Disorders, J. Med. Chem., 49(17):5047-5050 (2006).

Franchini, M. and Lippi, G., Factor V Leiden and hemophilia, *Thrombosis Research*, 125(2):119-123 (2010).

Huntington, J.A., Serpin structure, function and dysfunction, Journal of Thrombosis and Haemostasis, 9(Suppl.1):26-34 (2011).

Owen, M.C. et al., Mutation of antitrypsin to antithrombin, The New England Journal of Medicine, 309(12):694-698 (1983).

Rau, J.C. et al., Serpins in thrombosis, hemostasis and fibrinolysis, Journal of Thrombosis and Haemostasis, 5(Suppl.1):102-115 (2007).

Schechter, I. and Berger, A., On the size of the active site in proteases. I. Papain., Biochemical and Biophysical Research Communications, 27(2):157-162 (1967).

Schulman, S. et al., The plasma concentration of activated protein C appears normal in patients with haemophilia, Haemophilia, 15(2):566-570 (2009).

Filion, M.L. et al., Full or Partial Substitution of the Reactive Center Loop of [alpha]-1-Proteinase Inhibitor by that of Heparin Cofactor II: P1 Arg is Required for Maximal Thrombin Inhibition, Biochemistry, 43(46): 14864-14872 (2004).

Huntington, J.A. and Li, W., Structural insights into the multiple functions of protein C inhibitor, Cell. Mol. Life Sci., 66:113-121 (2009).

Huntington, J.A., Thrombin inhibition by the serpins, Journal of Thrombosis and Haemostasis, 11(Suppl. 1):254-264 (2013).

Hwang, S-R. and Hook, V.Y.H., Multiple domains of endopin 2A for serpin cross-class inhibition of papain, Archives of Biochemistry and Biophysics, 461(20: 219-224 (2007).

International Search Report for PCT/EP2014/077783, 7 pages (May 20, 2015).

Li, W. and Huntington, J.A., Enzyme catalysis and regulation: the heparin binding site of protein C inhibitor is protease-dependent, The Journal of Biological Chemistry, 283:36039-36045 (2008).

Li, W. et al., Molecular basis of thrombin recognition by protein C inhibitor revealed by the 1.6-Angstrom structure of the heparin-bridged complex, PNAS, 105(12):4661-4666 (2008).

Plotnick, M.I. et al., The Effects of Reactive Site Location on the Inhibitory Properties of the Serpin alpha 1-Antichymotrypsin, 277(33): 29927-29935 (2002).

Whisstock, J.C. et al., Serpins flex their muscle: II. Strucural insights into target peptidase recognition, polymerization, and transport functions, Journal of Biological Chemistry, 285(32):24307-24312 (2010).

Written Opinion for PCT/EP2014/077783, 10 pages (May 20, 2015).

Yamasaki, M. et al., Molecular bases of α1-antitrypsin deficiency revealed by the structure of a domain-swapped trimer, EMBO reports, 12(10):1011-1017 (2011).

* cited by examiner

US 9,982,035 B2

MODIFIED SERPINS FOR THE TREATMENT OF BLEEDING DISORDERS

FIELD

This invention relates to modified serpin molecules with altered specificity, in particular serpin molecules modified to have increased specificity for anticoagulant proteases, such as activated Protein C (APC).

BACKGROUND

Hemophilias are bleeding disorders, which are caused by a deficiency in circulating plasma fVIII (hemophilia A, HA) or fIX (hemophilia B, HB) (reviewed in Bolton-Maggs & Pasi, 2003). This reduces the activity of the intrinsic tenase (Xase) and thereby the amount of thrombin generated when tissue injury occurs. This leads to uncontrolled bleeding after injury as well as spontaneous bleeding into joints and soft tissue.

Hemophilia affects around 1 in 5,000 people. The 170,000 patients identified in the World Federation of Hemophilia Global Survey is an underestimate of the global health burden (World Federation of Hemophilia, 2011). The treatment costs are very high and treatment is frequent and lifelong.

Standard treatments for hemophilia entail replacement of the clotting factor affected, using either recombinant or plasma-derived factors (reviewed in Mannucci, 2003; 2008). However, a significant proportion of patients treated in this manner will develop inhibitory antibodies against the supplemented coagulation factor, rendering the treatment ineffective (reviewed in Brettler, 1996). Inhibitors occur in 30% of treated patients with hemophilia (reviewed in Teitel & Sholzberg 2013) but global estimates are low due to high mortality in untreated inhibitor patients and a low prevalence of inhibitors in many countries in which factor VIII replacement therapy is not available. Another drawback of conventional therapies is their expense, as well as the short half-life of the injected clotting factor, necessitating frequent treatments (reviewed in Lee et al, 2006).

In the case where patients develop inhibitory antibodies, bypassing agents are used for treatment of bleeding events (reviewed in (Negrier et al, 2006)). Bypassing agents reduce bleeding without directly supplying the clotting factor affected; they 'bypass' the activity of the tenase complex. Examples of current bypassing agents include recombinant fVIIa and FEIBA (Factor Eight Bypassing Activity), a prothrombin complex concentrate. These replacement treatments are very expensive (Bohn et al, 2004; Di Minno et al, 2010; Gringeri et al, 2003; Escobar, 2010) and need to be given even more frequently than the conventional therapies and in high doses due to the short half-lives of both products (reviewed in Haya et al, 2007). In addition, patient response has been shown to be variable and unpredictable (reviewed in Berntorp, 2009).

In addition, the short half-life of factor concentrates renders standard replacement therapy of hemophilia suboptimal. This is particularly evident in hemophilia A as factor VIII has a half-life of less than 12 hours. Consequently, despite the availability of treatment for both hemophilia A and B the bleeding rates are higher in hemophilia A and chronic hemophilic arthropathy is more common. This may be related to the short half-life of factor VIII and consequently the difficulty in maintaining a hemostatic level of factor VIII (Escobar and Sallah 2013). In a national review of treatment the annual frequency of bleeding in patients with severe hemophilia A without inhibitors was 14 compared to 9 in patients with hemophilia B (Nagel, et al 2011). The need for musculoskeletal surgery was 3-times greater in patients with hemophilia A. Tagariello et al found that patients with hemophilia A required joint replacement three times more often than patients with hemophilia B (Tagariello, et al 2009). Lowe et al found that hospitalization was required three times more frequently for patients with hemophilia A compared to hemophilia B (Lowe and Ludlam 2008).

Current treatments for bleeding disorders, such as hemophilia therefore have a range of drawbacks.

SUMMARY

The present inventors have recognised that the specificity of serpin molecules can be engineered by modification of residues within the reactive center loop (RCL), and have identified modified serpin molecules with increased specificity for anticoagulant proteases. These modified serpin molecules may be useful in therapy, for example for the treatment of bleeding.

An aspect of the invention provides a modified serpin having mutations at one or more of residues P4, P2, P1 and P1' in the reactive center loop (RCL) thereof.

Another aspect of the invention provides a modified serpin having mutations at one or both of residues P1' and P2 and optionally residues P4 and/or P1 in the reactive center loop (RCL) thereof.

The mutations may increase the inhibition of activated Protein C relative to the inhibition of thrombin.

The mutations may also increase the inhibition of activated Protein C relative to the inhibition of other procoagulant proteases, such as fVIIa, fIXa, fXa and fXIa.

Other aspects of the invention relate to the use of modified serpins as described herein for the treatment of bleeding, for example bleeding in patients with heritable bleeding disorders and acquired bleeding, including trauma, surgery and in patients receiving anticoagulant therapy.

BRIEF DESCRIPTION OF FIGURES

FIG. 3A shows pooled normal plasma from three separate plasmas incubated with either no PCI (black bar, -) or 5 μM of A22 wild-type (WT) PCI (grey bar, WT) or A22 P2KP1'K PCI (white bar, P2KP1'K). aPTT reagent was added and the samples incubated for 5 min at 37° C. Coagulation was then initiated by the addition of $CaCl_2$, to initiate coagulation via the intrinsic pathway and the time until clot formation measured. Bars show averages of at least three measurements, error bars show the standard deviation. The assay was stopped at 300 s. Samples shown at 300 s did not clot within the time of the experiment and are marked with asterisks. FIG. 3B shows the data from A without A22 WT PCI samples to show a small effect on the clotting time.

FIG. 5 shows the results of an activated partial thromboplastin time assay (aPTT) to determine the effect of FL $\alpha_1$AT Pitts C232S P2KP1'K on coagulation through the contact activation pathway (intrinsic).

FIG. 7 shows that FL $\alpha_1$AT Pitts C232S P2KP1'K rescues the anticoagulant effect of TM in normal human plasma (NP).

Figure 1:
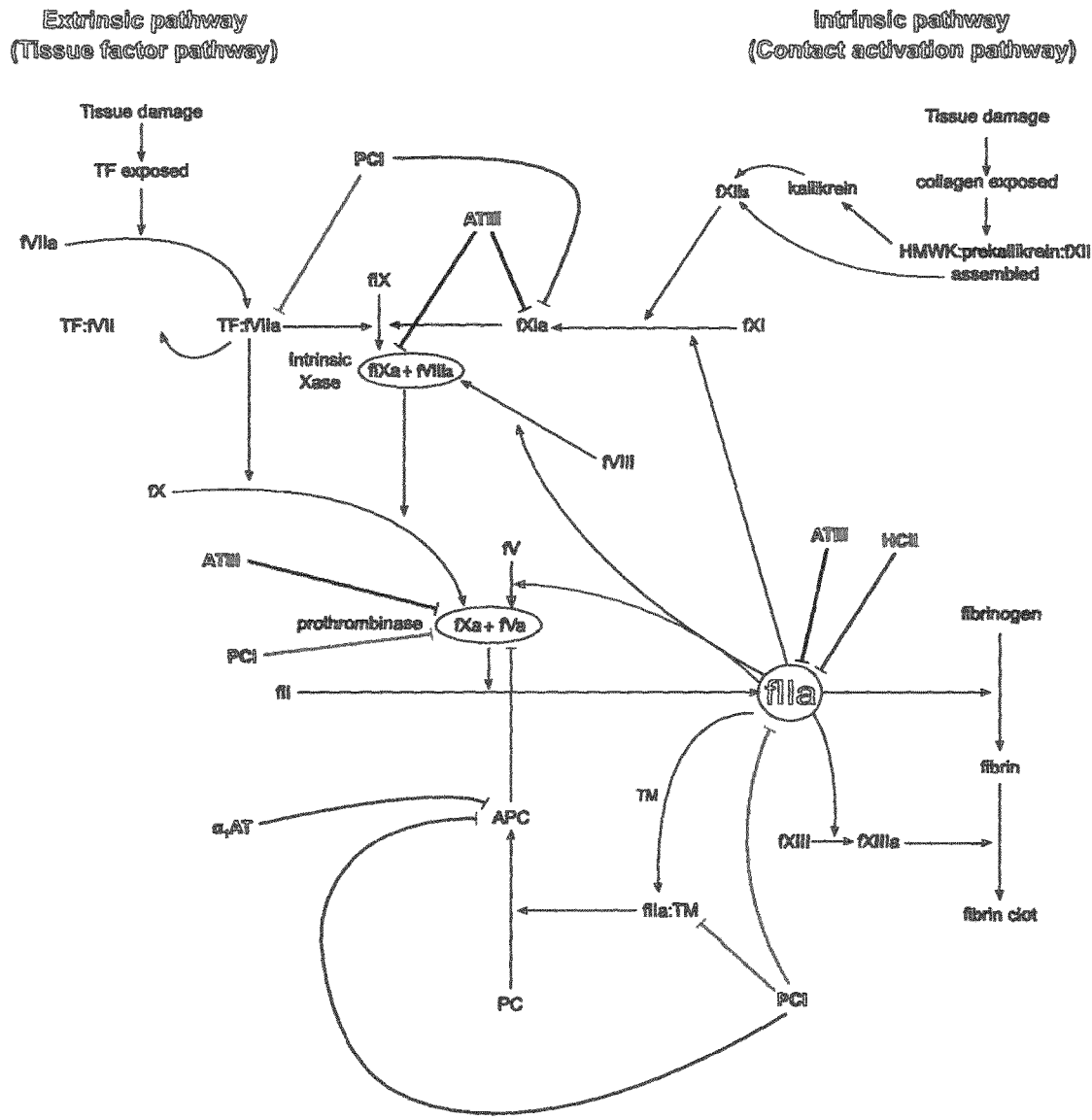
FIG. 1 shows the coagulation cascade and the regulatory role of serpins in this cascade.

Mean ETPs are shown from at least two independent experiments performed in duplicate. Error bars show standard deviations.

FIG. 9 shows that FL $\alpha_1$AT Pitts C232S P2KP1'K rescues the effect of on human HA plasma (fVIII-deficient plasma). FIGS. 9A-C show representative thrombin generation curves for reactions containing increasing concentrations of FL $\alpha_1$AT Pitts C232S P2KP1'K in the presence of (A) no TM (B) 1.25 nM TM (C) 5 nM TM. Curves show an average of duplicates. All assays were performed in fVIII-deficient plasma (less than 1% fVIII activity) from George King Biomedical. Coagulation was initiated by the addition of $CaCl_2$ and TF/phospholipid (RB low TF and phospholipid reagent #5006210, Technoclone GmbH) and 1:4,000 Dade Innovin (Siemens) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone). FIG. 9D shows mean ETPs (endogenous thrombin potentials), representing the total amount of thrombin generated during the reactions. Bars show the mean of two independent experiments performed in duplicate. Error bars represent the standard deviation.

FIG. 10 shows that FL $\alpha_1$AT Pitts C232S P2KP1'K rescues the effect of TM on human HB plasma (fIX-deficient plasma). (A-C) Representative thrombin generation curves are shown for reactions containing increasing concentrations of FL $\alpha_1$AT Pitts C232S P2KP1'K in the presence of (A) no TM (B) 1.25 nM TM (C) 5 nM TM. Curves show an average of duplicates. All assays were performed in fIX-deficient plasma (less than 1% fIX activity) from George King Biomedical. Coagulation was initiated by the addition of CaCl$_2$ and TF/phospholipid (RB low TF and phospholipid reagent #5006210, Technoclone GmbH) and 1:4,000 Dade Innovin (Siemens) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone). FIG. 10D shows mean ETPs (endogenous thrombin potentials), representing the total amount of thrombin generated during the reactions. Bars show the mean of at least two independent experiments performed in duplicate. Error bars represent the standard deviation.

FIG. 11 shows the effect of FL $\alpha_1$AT Pitts C232S and FL $\alpha_1$AT Pitts C232S P2KP1'K in HB mouse plasma. FIG. 11A-D show representative thrombin generation curves for reactions containing increasing concentrations of (A-B) FL $\alpha_1$AT Pitts C232S or (C-D) FL $\alpha_1$AT Pitts C232S P2KP1'K in the presence of (A and C) no TM (B and D) 750 nM soluble human TM. All assays were performed in HB mouse plasma collected by tail bleed into citrate, centrifuged to remove red cells and frozen at −80° C. Coagulation was initiated by the addition of $CaCl_2$, TF/phospholipid (RB low TF and phospholipid reagent, Technoclone) and 1:12,000 Dade Innovin (Siemens) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone). FIG. 11E shows mean ETPs (endogenous thrombin potentials), representing the total amount of thrombin generated during the reactions. Bars show the mean of four independent experiments. Error bars represent the standard deviation. All assays were performed at 33° C.

FIG. 12 shows that FL $\alpha_1$AT Pitts C232S P2KP1'K reduces bleeding in HB mice in a tail clip assay. Tail clip results show the total blood loss over a 10 min collection period after tail transection at 3 mm diameter for WT mice or HB mice. Mice were injected either with PBS, FL $\alpha_1$AT Pitts C232S or FL $\alpha_1$AT Pitts C232S P2KP1'K at the indicated doses in a total injection volume of 200 μl. Protein solutions were made up to 200 μl using PBS. The volume blood loss was determined by collection of blood from the tail into 14 ml saline. The collected blood was spun down and the red cells lysed, followed by measurement of the absorbance at 575 nm. A standard curve was constructed by determining the absorbance at 575 nm after red cell lysis using known volumes of collected blood. Blood loss in the experimental samples was then calculated from this standard. Each point shown indicates data from a single mouse and the horizontal lines show the mean of all animals per group. P values were calculated using an unpaired t-test. Circles indicate WT mice injected with PBS, squares indicate HB mice injected with PBS, triangles indicate HB mice injected with 7.5 mg/kg FL $\alpha_1$AT Pitts C232S, inverted triangles indicate HB mice injected with 7.5 mg/kg FL $\alpha_1$AT Pitts C232S P2KP1'K and diamonds indicate HB mice injected with 15 mg/kg FL $\alpha_1$AT Pitts C232S P2KP1'K.

FIG. 13 shows that FL $\alpha_1$AT Pitts C232S P2KP1'K increases stable clot formation in HB mice in a cremaster arteriole laser injury model. HB mice were infused with a fluorescently tagged α-fibrin antibody and a fluorescently tagged antibody for labeling platelets through a jugular vein cannula. Controls indicate the baseline level of clot formation after injury in mice infused with antibodies only. m indicates the number of mice per condition, n indicates the number of injuries performed for that condition. Light grey indicates no clot, dark grey indicates a platelet only clot, and black represents clots containing platelets and fibrin.

FIG. 14 shows that FL $\alpha_1$AT Pitts C232S P2KP1'K increases stable clot formation in HB mice in a cremaster arteriole laser injury model. FIG. 14 shows representative raw data of the results shown in FIG. 13. Fluorescence was quantified over time from all injuries for each condition. Graphs display the median value from all injuries in the indicated condition. Number of mice and total number of injuries were as follows: Control: 5 mice, 8 injuries; FL $\alpha_1$AT Pitts C232S at 7.5 mg/kg: 1 mouse, 7 injuries; FL $\alpha_1$AT Pitts C232S P2KP1'K at 7.5 mg/kg: 4 mice, 18 injuries; FL $\alpha_1$AT Pitts C232S P2KP1'K at 15 mg/kg: 3 mice, 20 injuries.

FIG. 15 shows the inhibition of thrombin and fXa by mutants of $\alpha_1$AT specific for APC over thrombin that were rescreened for fXa inhibition. The resulting four mutants, which should have reduced fXa inhibition were then tested for inhibition of (A) thrombin and (B) fXa, to determine if the screening had been successful in producing APC-specific mutants which did not inhibit thrombin or fXa. 1 μM serpin was incubated with 12.5 nM protease for different amounts of time. At the indicated timepoints, the reaction was stopped by addition of an excess of chromogenic substrate (S2238 for thrombin, S2222 for fXa). The residual enzyme activity was divided by the initial enzyme activity and the natural log of this value plotted against time. The slope of these plots is the observed rate constant, $k_{obs}$. To obtain an estimate of the second-order rate constant $k_2$, $k_{obs}$ was divided by the serpin concentration. Selected values are shown in the figure, to illustrate the highest inhibition of thrombin and fXa, as well as the value for the only mutant that did not substantially inhibit fXa (P2RP1'Q). The mutants shown all have the Pitts (M358R, P1R) mutation.

DETAILED DESCRIPTION

This invention relates to the modification of serpins to increase their specificity for APC relative to other coagulation proteases. Modified serpin variants specific for APC may be useful, for example as procoagulants.

Since they are specific to APC, the modified serpins described herein are expected to have few or no off-target effects and are specific to pathways that are activated on injury. This allows the modified serpins to be applied therapeutically and prophylactically, as well as in emergency situations, i.e. trauma. The dosing of modified serpins is predictable since they are suicide inhibitors, meaning that one molecule of serpin cannot inhibit more than one molecule of protease. In addition, because efficient natural clearance mechanisms are specific for serpin: protease complexes over serpins alone, the plasma half-lives of modified serpins are likely to exceed those of current bypassing agents. For example, the half-life of a modified serpin as described herein may be about 5 days.

Protein C (Gene ID 5624) is a vitamin K-dependent plasma glycoprotein that is cleaved to its activated form (activated Protein C, APC) by the thrombin-thrombomodulin complex. Human Protein C has the reference amino acid sequence of NP_000303.1 GI: 4506115 and may be encoded by the reference nucleotide sequence of NM_000312.3 GI: 270483720. APC is an anticoagulant protease that proteolytically cleaves fVa and fVIIIa (FIG. 1), thereby attenuating the production of thrombin.

A modified serpin as described herein may have one or more mutations in its reactive center loop (RCL). For example, the modified serpin may have one, two, three, four, or more than four mutations in its RCL. The residues at one, two, three or all four of positions P4, P2, P1 and P1' may be mutated. For example, the residues at one or both of positions P1' and P2 and optionally P1 and/or P4 may be mutated.

RCL residues are numbered herein according to the Schechter-Berger nomenclature for substrates and inhibitors of serine proteases (Schechter & Berger, 1967). This standard nomenclature allows the residue at specific positions in the RCL, such as positions P1', P1, P2 and/or P4, to be easily identified in any serpin sequence.

Preferably, the one or more mutations are the only mutations in the RCL of the modified serpin. For example, the RCL may consist of the sequence of the RCL of the wild-type serpin with mutations at one or both of positions P1' and P2 and optionally P1 and/or P4.

The RCL of the modified serpin may have mutations at the P1' and P2 positions; mutations at the P1', P2 and P1 positions; mutations at the P1', P2 and P4 positions or mutations at the P1', P2, P1 and P4 positions; a mutation at the P1' position; mutations at the P1' and P1 positions; mutations at the P1' and P4 positions or mutations at the P1', P1 and P4 positions; a mutation at the P2 position; mutations at the P2 and P1 positions; mutations at the P2 and P4 positions, mutations at the P2, P1 and P4 positions, a mutation at the P1 position, a mutation at the P4 position; or mutations at the P1 and P4 positions. The residues at other positions in the RCL may be unmutated wild-type residues.

Preferably, the residues at position P1'; positions P1' and P2; positions P1', P1 and P2; positions P2 and P1; positions P1 and P1'; positions P1', P2 and P4 or positions P1', P1, P2 and P4 of the RCL are mutated. In some preferred embodiments, the residues at positions P1', P1 and P2 are mutated.

The reactive center loop (RCL) of a serpin is typically about 20 residues in length and contains the scissile P1-P1' bond that is cleaved by the target protease. The RCL extends from strand 5 of beta sheet A to strand 1 of beta sheet C of the serpin. Residues P17 Glu, P15 Gly and P14 Thr are conserved in serpins. For example, the RCL of a serpin may comprise the consensus sequence P17 E, P16 E/K/R, P15 G, P14 T/S, P12-P9 (A/G/S)$_4$ (Hopkins et al. 1993; Irving et al. 2000). The RCL starts at residue P17 and usually ends at residue P3'. RCLs may be extended in some serpins, such as PCI, by additional residues on the P' side. For example, the RCL of α$_1$-antitrypsin consists of residues P17-P3' and the RCL of PCI consists of residues P17-P6'. Examples of serpins with residues P1', P1, P2 and P4 highlighted are shown in SEQ ID NOS: 1 to 11 below. The residues that constitute the mature serpin sequences are also indicated.

The residues in the other positions of the RCL in the serpin may be unmodified i.e. they may be the native residues of the wild-type serpin sequence. The modified serpin may therefore comprise an RCL having a wild-type sequence with mutations at positions P1, P1', P2 and/or P4 as described above.

The one or more mutations in the reactive center loop (RCL) of the modified serpin may comprise or consist of a mutation at the P1' position. Preferably, the mutation is a substitution. The native P1' residue in the RCL of the wild-type serpin may be replaced with a non-native residue in the modified serpin. For example, the native S residue at the P1' position in the wild-type sequence of α$_1$AT or PCI may be replaced with a residue other than S in the modified serpin.

The native P1' residue in the RCL of the wild-type serpin may be replaced with a large polar residue, such as Q, N, Y; a large hydrophobic residue, such as I, M and V; a positively charged residue such as R, H or K; or another residue such as C, A, S and E.

In some preferred embodiments, the P1' residue may be modified to a large polar residue, such as Q, N, Y; a large hydrophobic residue, such as V; or a positively charged residue such as R, H or K; more preferably, a positively charged or large polar residue, such as H, K, R, or Q; most preferably K.

In other embodiments, the P1' residue may be unmodified in the modified serpin. For example, the residue at the P1' position in the RCL of the modified serpin may be the residue that is present at the P1' residue in the wild-type serpin sequence.

The one or more mutations in the reactive center loop (RCL) of the modified serpin may comprise or consist of a mutation at the P2 residue. Preferably, the mutation is a substitution. For example, the native P2 residue in the RCL of the wild-type serpin may be replaced with a non-native residue in the modified serpin.

The native P2 residue in the RCL of the wild-type serpin may be replaced with a large polar residue, such as D, Q, N, Y, a large hydrophobic residue such as W, L, I, V and F, a positively charged residue, such as R, H or K or another residue, such as C, A, T, S or P.

In some embodiments the P2 residue in the modified serpin may be other than P.

In some preferred embodiments, the P2 residue may be modified to a large polar residue, such as Q, N, Y, a large hydrophobic residue such as W or a positively charged residue such as R, H or K, most preferably a positive residue, such as H, K or R, preferably K.

In some embodiments, the P2 residue may be unmodified in the modified serpin. For example, the residue at the P2 position in the RCL of the modified serpin may be the residue that is present at the P2 residue in the wild-type serpin sequence.

The one or more mutations in the RCL of the modified serpin may comprise or consist of substitutions at the P1' and/or P2 residues i.e. the residues located at the P1' and/or P2 positions in the RCL of the wild-type serpin sequence may be replaced by other residues in the modified serpin.

In preferred embodiments, the modified serpin has mutations at both the P2 and the P1' positions of the RCL.

Suitable residues at the P2 and P1' positions of the modified serpin are described above.

In some modified serpins described herein, at least one of the P1' and P2 residue may be a positively charged residue, such as R, H or K or a large polar residue, such as D, Y, Q or N; a large hydrophobic residue, such as W, L, F, V, M or I; or another residue, such as L, C, A, E, T, S or P. Preferably, at least one of the P1' and P2 residue is a positively charged residue, such as R, H or K; a large polar residue, such as Y, Q or N; or a large hydrophobic residue, such as W, L, F, V or I.

Examples of P2 and the P1' residues respectively in a modified serpin as described herein include KK, FK, RK, VK, LK, QK, CK, PK, FR, HR, IR, SR, TR, VR, YR, AR, PR, RS, KS, QV, RV, RI, RH, KH, TH, RC, RA, LY, QY, TY, DM, TM, WN, RN, HN, TN, KN, NN, PE, RQ, KQ and TQ.

In some preferred embodiments, both the P1' and the P2 residue may be modified to positively charged residues, such as K, H or R, most preferably K.

In some embodiments, the P2 and the P1' residues respectively in a modified serpin as described herein may be other than PN, FS, QS, AS, TS, HS, TA, PT, CC, PS, PT, PM, PH, PA or PC. For example, the P2 and P1' residues may be other than PN, FS, QS, AS, TS, HS, TA, PT, CC or PC in a PCI scaffold or other than PS, PT, PM, PH or PA in an $\alpha_1$AT scaffold, In some embodiments, the P1 residue may be unmodified in the modified serpin. For example, the residue at the P1 position in the RCL of the modified serpin may be the residue that is present at the P1 residue in the wild-type serpin sequence. For example, the P1 residue in a modified PCI may be an R residue.

In other embodiments, the P1 residue may be mutated in the modified serpin. For example, the one or more mutations in the reactive center loop (RCL) of the modified serpin further comprise a mutation at the P1 residue. Preferably, the mutation is a substitution. The native P1 residue in the RCL of the wild-type serpin may be replaced with a non-native residue in the modified serpin.

In some embodiments, the P1 residue may be mutated or modified to a positively charged residue such as H, K or R, preferably R.

Preferably, a native residue that is non-positively charged at the P1 position of a wild-type serpin may be replaced by a positively charged residue in the modified serpin. For example, M at the P1 position of wild-type $\alpha_1$AT may be replaced by a positively charged residue, such as R, in a modified $\alpha_1$AT. The Pittsburgh (Pitts) variant of $\alpha_1$AT has a mutation at residue 358 which replaces the M residue at the P1 position with an R residue.

In some embodiments, the P4 residue may be unmodified in the modified serpin. For example, the residue at the P4 position in the RCL of the modified serpin may be the residue that is present at the P4 residue in the wild-type serpin sequence. For example, the P4 residue in a PCI scaffold may be F and the P4 residue in an $\alpha_1$AT scaffold may be A.

In other embodiments, the P4 residue may be mutated in the modified serpin. For example, the one or more mutations in the reactive center loop (RCL) of the modified serpin further comprise a mutation at the P4 residue.

Preferably, the mutation is a substitution. The residue at the P4 residue in the RCL of the wild-type serpin may be replaced with a different residue in the modified serpin. For example, the P4 residue in a modified PCI may be mutated or modified to a residue other F and the P4 residue in a modified $\alpha_1$AT may be mutated or modified to a residue other than A.

Suitable residues in the P4 position of the RCL of the modified serpin include S, R, V, C, W, K, G, L, H, F, T, Q and A.

In examples of modified procoagulant serpins as described herein,
(1) the P4 residue is Q, the P2 residue is R, the P1 residue is R and the P1' residue is N;
(2) the P4 residue is K, the P2 residue is R, the P1 residue is R and the P1' residue is H;
(3) the P4 residue is S, the P2 residue is L, the P1 residue is R and the P1' residue is K;
(4) the P4 residue is H, the P2 residue is R, the P1 residue is R and the P1' residue is V;
(5) the P4 residue is F, the P2 residue is K, the P1 residue is R and the P1' residue is K;
(6) the P4 residue is F, the P2 residue is R, the P1 residue is R and the P1' residue is K;
(7) the P4 residue is F, the P2 residue is V, the P1 residue is R and the P1' residue is K;
(8) the P4 residue is C, the P2 residue is L, the P1 residue is R and the P1' residue is K;
(9) the P4 residue is F, the P2 residue is F, the P1 residue is R and the P1' residue is R;
(10) the P4 residue is S, the P2 residue is H, the P1 residue is R and the P1' residue is R;
(11) the P4 residue is G, the P2 residue is I, the P1 residue is R and the P1' residue is R;
(12) the P4 residue is R, the P2 residue is Q, the P1 residue is R and the P1' residue is V;
(13) the P4 residue is T, the P2 residue is R, the P1 residue is R and the P1' residue is V
(14) the P4 residue is R, the P2 residue is R, the P1 residue is R and the P1' residue is I;
(15) the P4 residue is V, the P2 residue is R, the P1 residue is R and the P1' residue is I;
(16) the P4 residue is L, the P2 residue is R, the P1 residue is R and the P1' residue is I;
(17) the P4 residue is T, the P2 residue is L, the P1 residue is R and the P1' residue is Y;
(18) the P4 residue is A, the P2 residue is Q, the P1 residue is R and the P1' residue is Y;
(19) the P4 residue is K, the P2 residue is D, the P1 residue is R and the P1' residue is M;
(20) the P4 residue is W, the P2 residue is W, the P1 residue is R and the P1' residue is N;
(21) the P4 residue is A, the P2 residue is K, the P1 residue is R, and the P1' residue is S;
(22) the P4 residue is A, the P2 residue is R, the P1 residue is R, and the P1' residue is S;
(23) the P4 residue is A, the P2 residue is P, the P1 residue is R, and the P1' residue is E;
(24) the P4 residue is A, the P2 residue is P, the P1 residue is R, and the P1' residue is R;
(25) the P4 residue is A, the P2 residue is P, the P1 residue is R, and the P1' residue is K;
(26) the P4 residue is A, the P2 residue is T, the P1 residue is R, and the P1' residue is M;
(27) the P4 residue is A, the P2 residue is T, the P1 residue is R, and the P1' residue is H;
(28) the P4 residue is A, the P2 residue is T, the P1 residue is R, and the P1' residue is Q;
(29) the P4 residue is A, the P2 residue is T, the P1 residue is R, and the P1' residue is N;
(30) the P4 residue is A, the P2 residue is T, the P1 residue is R, and the P1' residue is Y;
(32) the P4 residue is A, the P2 residue is T, the P1 residue is R, and the P1' residue is R;

(33) the P4 residue is A, the P2 residue is R, the P1 residue is R, and the P1' residue is A;
(34) the P4 residue is A, the P2 residue is R, the P1 residue is R, and the P1' residue is H;
(35) the P4 residue is A, the P2 residue is R, the P1 residue is R, and the P1' residue is C;
(36) the P4 residue is A, the P2 residue is R, the P1 residue is R, and the P1' residue is N;
(37) the P4 residue is A, the P2 residue is S, the P1 residue is R, and the P1' residue is R;
(38) the P4 residue is A, the P2 residue is K, the P1 residue is R, and the P1' residue is N;
(39) the P4 residue is A, the P2 residue is K, the P1 residue is R, and the P1' residue is H;
(40) the P4 residue is A, the P2 residue is K, the P1 residue is R, and the P1' residue is K;
(41) the P4 residue is A, the P2 residue is V, the P1 residue is R, and the P1' residue is R;
(42) the P4 residue is A, the P2 residue is Y, the P1 residue is R, and the P1' residue is R;
(43) the P4 residue is A, the P2 residue is A, the P1 residue is R, and the P1' residue is R;
(44) the P4 residue is A, the P2 residue is C, the P1 residue is R, and the P1' residue is K;
(45) the P4 residue is A, the P2 residue is W, the P1 residue is R, and the P1' residue is N;
(46) the P4 residue is A, the P2 residue is H, the P1 residue is R, and the P1' residue is N;
(47) the P4 residue is A, the P2 residue is Q, the P1 residue is R, and the P1' residue is K; or,
(48) the P4 residue is A, the P2 residue is N, the P1 residue is R, and the P1' residue is N.
(49) the P4 residue is F, the P2 residue is F, the P1 residue is R, and the P1' residue is K.
(50) the P4 residue is A, the P2 residue is K, the P1 residue is R, and the P1' residue is Q,
(51) the P4 residue is A, the P2 residue is R, the P1 residue is R, and the P1' residue is Q.

In some preferred modified serpins, the P4 residue is A, the P2 residue is K, the P1 residue is R, and the P1' residue is K.

In some embodiments, the residues at the P4, P2 and the P1' positions in a modified procoagulant serpin as described herein may be other than HPN, DKN, HPE, FFS, LQS, HAS, YTS, AHS, ATA, LPT, ACC, APT, APA, APM, APH, APS and VPC, respectively. For example, a modified PCI may have residues other than HPN, DKN, HPE, FFS, LQS, HAS, YTS, AHS, ATA, LPT, ACC and VPC at the P4, P2 and the P1' positions and a modified α₁AT may have residues other than APT, APA, APM or APH at the P4, P2 and the P1' positions. In some embodiments, the combination of residues at the P4, P2 and the P1' positions in a modified procoagulant serpin as described herein may be non-naturally occurring i.e. the combination of residues at the P4, P2 and the P1' positions is not found in the parent wild-type (i.e. unmodified) serpin or in other wild-type serpins.

A modified serpin as described herein may comprise the sequence of a wild-type (i.e. unmodified) serpin, preferably a mature wild-type serpin, with one or more mutations in the RCL thereof as described above, and optionally one or more additional mutations outside the RCL.

The sequences of wild-type serpins are well-known in the art, and may include SEQ ID NOS: 1 to 11 as set out herein. The sequences of wild-type serpins may include the sequence of mature wild-type proteins.

The mature protein C inhibitor (PCI) sequence including its propeptide corresponds to residues 20 to 406 of SEQ ID NO: 1. The mature α₁-antichymotrypsin corresponds to residues 26 to 423 of SEQ ID NO: 2. The mature C1-esterase inhibitor sequence corresponds to residues 23-500 of SEQ ID NO: 3. The mature α₂-antiplasmin sequence corresponds to residues 28-491 of SEQ ID NO: 4. The mature antithrombin (ATIII) sequence corresponds to residues 33-464 of SEQ ID NO: 5. The mature heparin cofactor II sequence corresponds to residues 20-499 of SEQ ID NO: 6. The mature α₁-antitrypsin (α₁AT) sequence corresponds to residues 25-418 of SEQ ID NO: 7. The mature kallistatin sequence corresponds to residues 21-427 of SEQ ID NO: 8. The mature plasminogen activator inhibitor sequence corresponds to residues 24-402 of SEQ ID NO: 9. The mature protein Z dependent inhibitor sequence corresponds to residues 22-444 of SEQ ID NO: 10. The mature protease nexin 1 isoform a sequence corresponds to residues 20-398 of SEQ ID NO: 11.

Other than mutations of residues in the RCL as described above, a modified serpin may have 50 or fewer amino acid residues altered relative to a wild-type serpin amino acid sequence (for example the mature serpin sequence of one of SEQ ID NOS 1 to 11, preferably SEQ ID NO: 1 or 7), preferably 45 or fewer, 40 or fewer, 30 or fewer, 20 or fewer, 15 or fewer, 10 or fewer, 5 or fewer or 3 or fewer. For example, a modified serpin may comprise the sequence of a wild-type serpin with 50 or fewer, 45 or fewer, 40 or fewer, 30 or fewer, 20 or fewer, 15 or fewer, 10 or fewer, 5 or fewer or 3 or fewer amino acid residues mutated or altered, in addition to the one, two, three or four amino acid residues in the RCL of the serpin that are mutated or altered as described above (i.e. the residues at positions P1' and/or P2 and optionally P1 and/or P4).

An amino acid residue in the wild-type amino acid sequence may be altered or mutated by insertion, deletion or substitution, preferably substitution for a different amino acid residue. Such alterations may be caused by one or more of addition, insertion, deletion or substitution of one or more nucleotides in the encoding nucleic acid.

For example, a modified serpin may comprise the amino acid sequence of residues 25-418 of SEQ ID NO: 12 having 50 or fewer mutations, wherein said mutations are at positions other than P4, P2, P1 and P1' i.e. the P4 residue is A in the RCL of the modified serpin is A, the P2 residue is K, P1 residue is R and the P1' residue is K.

The P4 residue in the modified serpin of SEQ ID NO: 12 is located at position 379 (355 of the mature protein), the P2 residue is located at position 381 (357 of the mature protein), the P1 residue is located at position 382 (358 of the mature protein), and the P1' residue is located at position 383 (359 of the mature protein).

The modified serpin may share at least 50% sequence identity with the wild-type amino acid sequence of a wild-type serpin, for example the mature serpin sequence of any one of SEQ ID NOS: 1 to 11, preferably SEQ ID NO: 1 or 7, at least 55%, at least 60%, at least 65%, at least 70%, at least about 80%, at least 90%, at least 95%, at least 98% or at least 99% sequence identity.

For example, a modified serpin may comprise an amino acid sequence having at least 50% sequence identity to residues 25-418 of SEQ ID NO: 12, wherein the P4 residue in the RCL of the modified serpin is A, the P2 residue is K, P1 residue is R and the P1' residue is K.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm may be used (Nucl. Acids Res. (1997) 25 3389-3402). Sequence identity and similarity may also be determined using Genomequest™ software (Gene-IT, Worcester Mass. USA).

Sequence comparisons are preferably made over the full-length of the relevant sequence described herein.

Preferably, a modified procoagulant serpin as described herein comprises the RCL consensus P17 E, P16 S/E/K/R, P15 G, P14 T/S, P12-P9 (A/G/S)$_4$.

A modified serpin may further comprise one or more residues that are conserved in wild-type serpin sequences. For example, a modified serpin may comprise some or all of the following residues (numbered according to their position in α1AT): 33F, 49N, 53S, 54P, 56S, 61L, 67G, 72T, 80L, 130F, 147F, 157I, 158N, 161V, 165T, 167G, 169I, 180T, 184L, 186N, 190F, 191K, 192G, 194W, 198F, 203T, 208F, 218V, 220M, 221M, 277Y, 254L, 255P, 289P, 290K, 299L, 303L, 307G, 312F, 316A, 327L, 334H, 342E, 344G, 347A, 369P, 370F, 383L, 384F, 386G, and 391P (Irving et al 2008). The corresponding conserved residues in other serpin sequences may be readily determined using routine sequence analysis.

Mutations or variations outside the RCL of the modified serpin may include replacement of one or more Cys residues in the modified serpin, such as the C232 (numbering according to the mature sequence) residue of $α_1$AT, to abolish disulfide bridge formation or other modifications; deletion or substitution of residues at the N terminus of the wild-type sequence, for example to facilitate expression; or mutation or modification of residues in the heparin binding sites of the modified serpins (i.e. helix D or helix H) in order to alter the heparin binding activity of the modified serpin.

In some embodiments, the modified serpin may have an N terminal truncation relative to the wild-type serpin. For example, the modified serpin may have a 10 to 30 residue truncation at the N terminus, preferably about 20 residues.

One or more residues in the modified serpin may be non-natural amino acids, modified amino acids or D-amino acids. The use of such amino acids is well-known to those of skill in the art A modified serpin as described herein may display the secondary structure of the wild-type serpin, for example a modified serpin may display a structure comprising 3 beta sheets, 8-9 alpha helices and a flexible RCL of about 20 residues.

In some preferred embodiments, the modified serpin may consist of the amino acid sequence of a wild-type serpin with one or more mutations in the reactive center loop (RCL) thereof as described herein.

Preferably, the modified serpin is non-immunogenic in a human. For example, the wild-type serpin may be a human serpin, preferably a human plasma serpin.

The wild-type serpin may be $\alpha_1$-antichymotrypsin (SERPINA3), $\alpha_2$-antiplasmin (SERPINF2) antithrombin (ATIII) (SERPINC1), heparin cofactor II (HCII) (SERPIND1), protein C inhibitor (PCI) (SERPINA5), $\alpha_1$-antitrypsin ($\alpha_1$AT) (SERPINA1), Kallistatin (SERPINA4), Plasminogen activator inhibitor-1 (SERPINE1), C1-esterase inhibitor (SERPING1), protease nexin 1 (SERPINE2) or Protein Z-dependent inhibitor (SERPINA10) (Whisstock et al JBC. 285 32 24307-24312, Rau et al Journal of Thrombosis and Hemostasis, 5 (Suppl. 1): 102-115, Huntington, Journal of Thrombosis and Hemostasis, 9 (Suppl. 1): 26-34).

Preferably, the wild-type serpin is ATIII, HCII, PCI or $\alpha_1$AT, most preferably PCI or $\alpha_1$AT (Huntington et al Cell. Mol. Life Sci. 66 (2009) 113-121; Li et al JBC. 283 51 36039-36045; and Li et al PNAS 2008 105 4661-4666).

$\alpha_1$-antichymotrypsin (SERPINA3; Gene ID 12) may have the reference amino acid sequence of NP_001076.2 GI:50659080 (SEQ ID NO: 2) and may be encoded by the reference nucleotide sequence of NM_001085.4 GI:73858562.

C1-esterase inhibitor (SERPING1; Gene ID 710) may have the reference amino acid sequence of NP_000053.2 GI: 73858568 (SEQ ID NO: 3) and may be encoded by the reference nucleotide sequence of NM_000062.2 GI:73858567.

$\alpha_2$-antiplasmin (SERPINF2 Gene ID 5345) may have the reference amino acid sequence of NP_000925.2 GI:115583663 (SEQ ID NO: 4) and may be encoded by the reference nucleotide sequence of NM_001165920.1 GI:260064047

Antithrombin (ATIII) (SERPINC1 Gene ID 462) may have the reference amino acid sequence of NP_000479.1 GI: 4502261 (SEQ ID NO: 5) and may be encoded by the reference nucleotide sequence of NM_000488.3 GI:254588059

Heparin cofactor II (HCII) (SERPIND1 Gene ID3053) may have the reference amino acid sequence of NP_000176.2 GI: 73858566 (SEQ ID NO: 6) and may be encoded by the reference nucleotide sequence of NM_000185.3 GI:73858565

Protein C inhibitor (PCI) (SERPINA5 Gene ID 5104) may have the reference amino acid sequence of NP_000615.3 GI: 194018472 and may be encoded by the reference nucleotide sequence of NM_000624.5 GI:401782581. In some preferred embodiments, the protein C inhibitor (PCI) may be an allelic variant resulting from a substitution at SNP rs6115, VAR_013081 (the S45N variant, numbering according to mature protein including the propeptide) and having the sequence shown in SEQ ID NO: 1. Residues 1-19 of SEQ ID NO: 1 correspond to the signal sequence. In plasma, PCI may exist in a full-length form which includes the propeptide of residues 20-25 of SEQ ID NO: 1 (i.e. residues 20-406 of SEQ ID NO: 1) or N terminally cleaved form which lacks the propeptide (i.e. residues 26-406 of SEQ ID NO: 1).

$\alpha_1$-antitrypsin ($\alpha_1$AT) (SERPINA1 Gene ID 5265) may have the reference amino acid sequence of NP_000286.3 GI:50363217 (SEQ ID NO: 7) and may be encoded by the reference nucleotide sequence of NM_000295.4 GI:189163524.

Kallistatin (SERPINA4 Gene ID 5267) may have the reference amino acid sequence of NP_006206.2 GI: 21361302 (SEQ ID NO: 8) and may be encoded by the reference nucleotide sequence of NM_006215.2 GI: 21361301.

Plasminogen activator inhibitor-1 (SERPINE1 Gene ID 5054) may have the reference amino acid sequence of NP_000593.1 GI: 10835159 (SEQ ID NO: 9) and may be encoded by the reference nucleotide sequence of NM_000602.4 GI: 383286745.

Protein Z-dependent inhibitor (PZI) (SerpinA10; Gene ID 51156) may have the reference amino acid sequence of NP_057270.1 GI: 7705879 (SEQ ID NO: 10) and may be encoded by the reference nucleotide sequence of NM_016186.2 GI: 154759289.

Protease nexin 1 (PN1) (SerpinE2; Gene ID 5270) may have the reference amino acid sequence of NP_001130000.1 GI: 24307907, NP_001130002.1 GI: 211904152 or NP_006207.1 GI: 211904156 (SEQ ID NO: 11) and may be encoded by the reference nucleotide sequence of NM_001136528.1 GI: 211904151, NM_001136530.1 GI: 211904155 or NM_006216.3 GI: 211904150.

The P1', P1, P2 and P4 residues that may be mutated as described above are highlighted in bold in SEQ ID NOS: 1 to 11.

The one or more mutations in the RCL alter the specificity of the modified serpin relative to the unmodified wild-type serpin. The modified serpin displays increased selectively for anticoagulant proteases over procoagulant proteases compared to the wild-type serpin.

Preferably, the one or more mutations within the RCL increase the inhibition of APC by the modified serpin relative to the inhibition of other coagulation proteases, in particular one or more procoagulant proteases out of thrombin, fXa, fVIIa, fIXa and fXIa.

For example, the one or more mutations in the RCL of the modified serpin may increase the inhibition of APC by the modified serpin relative to the inhibition of thrombin. The selective inhibition of APC relative to thrombin may be increased in the presence or absence of heparin.

In addition, the one or more mutations in the RCL of the modified serpin may increase the inhibition of APC by the modified serpin relative to the inhibition of 1, 2, 3 or all 4 of the procoagulant proteases fXa, fVIIa, fIXa and fXIa.

A serpin modified as described herein displays greater inhibition of APC relative to thrombin and other procoagulant proteases than the unmodified wild-type serpin.

The modified serpin may show greater inhibition of APC than inhibition of thrombin. For example, inhibition of APC by the modified serpin may be at least 5 fold more, at least 10 fold more at least 100 or at least 1000 fold more than inhibition of thrombin by the modified serpin. In some embodiments, the modified serpin may inhibit APC with a second-order rate constant ($k_2$) that is at least 5 fold more, at least 10 fold more at least 100 or at least 1000 fold more than the second-order rate constant for the inhibition of thrombin. Preferably the stoichiometry of inhibition of the modified serpin for APC is 1.

Preferably, a modified serpin as described herein may bind and inhibit APC but display no binding or inhibition or substantially no binding or inhibition of thrombin.

The one or more mutations in the RCL may also increase the inhibition of APC relative to the inhibition of 1, 2, 3, or all 4 of fVIIa, fIXa, fXa and fXIa. Inhibition of APC relative to fVIIa, fIXa, fXa and/or fXIa may be increased in the presence or absence of heparin.

For example, the modified serpin may display greater inhibition of APC relative to 1, 2, 3, or all 4 of fVIIa, fIXa, fXa and fXIa than the wild-type serpin.

The modified serpin may inhibit APC more than it inhibits fVIIa. For example, inhibition of APC by the modified serpin may be at least 2 fold more, at least 10 fold more, at least 100 more, or at least 1000 fold more than the inhibition of fVIIa by the modified serpin.

The modified serpin inhibits APC with a second-order rate constant ($k_2$) that is at least 2 fold more, at least 10 fold more, at least 100 more, or at least 1000 fold more than the second-order rate constant for the inhibition of fVIIa.

The modified serpin may inhibit APC more than it inhibits fIXa. For example, inhibition of APC by the modified serpin may be at least 2 fold more, at least 10 fold more, at least 100 more or at least 1000 fold more than the inhibition of fIXa by the modified serpin. The modified serpin inhibits APC with a second-order rate constant ($k_2$) that is at least 2 fold more, at least 10 fold more, at least 100 more, or at least 1000 fold more than the second-order rate constant for the inhibition of fIXa.

The modified serpin may inhibit APC more than it inhibits fXa. For example, inhibition of APC by the modified serpin may be at least 1.5 fold more, at least 2 fold more, at least 10 fold more at least 100 or at least 1000 fold more than the inhibition of fXa by the modified serpin. The modified serpin inhibits APC with a second-order rate constant ($k_2$) that is at least 1.5 fold more, at least 2 fold more, at least 10 fold more, at least 100 more, or at least 1000 fold more than the second-order rate constant for the inhibition of fXa.

The modified serpin may inhibit APC more than it inhibits fXIa. For example, inhibition of APC by the modified serpin may be at least 2 fold more, at least 10 fold more at least 100 or at least 1000 fold more than the inhibition of fXIa by the modified serpin. The modified serpin inhibits APC with a second-order rate constant ($k_2$) that is at least 2 fold more, at least 10 fold more, at least 100 more, or at least 1000 fold more than the second-order rate constant for the inhibition of fXIa.

A modified serpin as described herein may be part of a fusion protein which contains one or more heterologous amino acid sequences additional to the modified serpin sequence. For example, the fusion protein comprising the modified serpin may further comprise one or more additional domains which improve the stability, pharmacokinetic, targeting, affinity, purification and production properties of the modified serpin.

Suitable additional domains include immunoglobulin Fc domains. Immunoglobulin Fc domains are well-known in the art and include the human IgG1 Fc domain. A human immunoglobulin Fc domain may be located at the N-terminal or C-terminal end of the modified serpin.

Modified serpins as described herein may be provided using synthetic or recombinant techniques which are standard in the art.

In some embodiments, the modified serpin may be produced as a fusion protein further comprising an affinity tag, which may, for example, be useful for purification. An affinity tag is a heterologous peptide sequence which forms one member of a specific binding pair. Polypeptides containing the tag may be purified by the binding of the other member of the specific binding pair to the polypeptide, for example in an affinity column. For example, the tag sequence may form an epitope which is bound by an antibody molecule.

Suitable affinity tags include for example, glutathione-S-transferase, (GST), maltose binding domain (MBD), MRGS(H)$_6$ (SEQ ID NO: 13), DYKDDDDK (FLAG™) (SEQ ID NO: 14), T7-, S-(KETAAAKFERQHMDS; SEQ ID NO: 15), poly-Arg ($R_{5-6}$) (SEQ ID NOS: 16 and 17), poly-His ($H_{2-10}$) (SEQ ID NOS: 18 to 24), poly-Cys ($C_4$; SEQ ID NO: 25) poly-Phe ($F_{11}$) (SEQ ID NO: 26), poly-Asp ($D_{5-16}$) (SEQ ID NOS: 27 to 38), SUMO tag (Invitrogen Champion pET SUMO expression system), Strept-tag II (WSH-PQFEK; SEQ ID NO: 39), c-myc (EQKLISEEDL; SEQ ID NO: 40), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag.100 (Qiagen; 12 aa tag derived from mammalian MAP kinase 2), Cruz tag 09™ (MKAEFRRQESDR (SEQ ID NO: 41), Santa Cruz Biotechnology Inc.) and Cruz tag 22™ (MRDALDRLDRLA (SEQ ID NO: 42), Santa Cruz Biotechnology Inc.). Known tag sequences are reviewed in Terpe (2003) Appl. Microbiol. Biotechnol. 60 523-533. In preferred embodiments, a poly-His tag such as (H)$_6$ (SEQ ID NO: 20), His-SUMO tag (Invitrogen Champion pET SUMO expression system), or MRGS(H)$_6$ (SEQ ID NO: 13) may be used.

The affinity tag sequence may be separated from the modified serpin after purification, for example, using site-specific proteases.

In some embodiments, the modified serpin may be coupled to an appropriate signal leader peptide to direct secretion of the fusion polypeptide from cell into the culture medium. A range of suitable signal leader peptides are known in the art. The signal leader peptide may be a serpin signal sequence or may be heterologous to the modified serpin i.e. it may be a non-serpin signal sequence. For example, an α-factor secretion signal or BiP signal sequence may be employed. Preferably, the signal peptide is removed by post-translational processing after expression of the polypeptide.

Modified serpins as described herein may be isolated, in the sense of being free from contaminants, such as unmodified serpins and other polypeptides and/or serum components.

Modified serpins as described herein may inhibit one or more activities of activated protein C (APC). For example, modified serpins as described herein may inhibit the proteolytic cleavage of one or more APC substrates, such as fVa or fVIIIa. For example, binding of the modified serpin to APC may result in an at least 5-fold, at least 10-fold, or at least 15-fold decrease in the proteolytic cleavage of fVa, fVIIIa and/or another APC substrate. In some embodiments, binding of APC by the modified serpin may result in no detectable cleavage of fVa or fVIIIa substrate by APC.

Techniques for measuring APC activity, for example by measuring the proteolytic cleavage of APC substrates in vitro are standard in the art and are described herein. Suitable assays for use in determining APC activity include standard kinetic assays, for example to measure rate constants, and coagulation assays, including thrombin generation assays (TGA).

Techniques for measuring the activity of procoagulant proteases, for example by measuring the proteolytic cleavage of chromogenic substrates in vitro are standard in the art and are described herein. Suitable assays for use in determining protease activity include standard kinetic assays, for example to measure rate constants, and coagulation assays, including thrombin generation assays (TGA), prothrombin time assays (PT) and activated partial thromboplastin time assays (aPTT).

In some embodiments, modified serpins as described herein may be further modified by chemical modification, for example by PEGylation, or by incorporation in a liposome, to improve their pharmaceutical properties, for example by increasing in vivo half-life.

A modified serpin as described herein may be attached to one or more polyethylene glycol (PEG) or other moieties to increase the in vivo half-life of the modified serpin (Cantin et al. 2002, Am. J. Respir. Cell Mol. Biol. 27; 659-665). For example, a modified serpin may be mono-pegylated or poly-pegylated (for example, with 2-6 PEG moieties). Suitable pegylation methods are well known in the art.

The effect of a modified serpin on coagulation and bleeding may be determined. Suitable techniques are standard in the art. For example, the effect of a modified serpin on thrombin generation may be determined using a thrombin generation assay (TGA) or an activated partial thromboplastin time assay or a prothrombin time assay described herein. Suitable in vivo models include cremaster arteriole laser injury models, $FeCl_3$ carotid artery models and tail clip assays as described herein. Other suitable coagulation models are well known in the art.

Other aspects of the invention provide a nucleic acid encoding a modified serpin as described above and a vector comprising such a nucleic acid.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as *E. coli.*

Vectors may be plasmids, viral e.g. phage, or phagemid, as appropriate. For further details see, for example, Molecular Cloning: a Laboratory Manual: 3rd edition, Russell et al., 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, are described in detail in Current Protocols in Molecular Biology, Ausubel et al. eds. John Wiley & Sons, 1992.

A nucleic acid or vector as described herein may be introduced into a host cell.

Another aspect of the invention provides a recombinant cell comprising a nucleic acid or vector that expresses a polypeptide comprising or consisting of a modified serpin as described above.

A range of host cells suitable for the production of recombinant modified serpins are known in the art. Suitable host cells may include prokaryotic cells, in particular bacteria such as *Escherichia coli* and *Lactococcus lactis* and eukaryotic cells, including mammalian cells such as CHO and CHO-derived cell lines (Lec cells), HeLa, COS, HEK293 and HEK-EBNA cells, amphibian cells such as *Xenopus* oocytes, insect cells such as *Trichoplusia ni*, Sf9 and Sf21 and yeast cells, such as *Pichia pastoris.*

Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well-known in the art.

The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques.

In some embodiment, nucleic acid encoding a modified serpin as described herein may be contained in a vector suitable for administration to an individual e.g. for gene therapy applications. Suitable vectors include retroviral vectors, lentiviral vectors, adenoviral vectors and AAT vectors.

The introduction may be followed by expression of the nucleic acid to produce the encoded modified serpin. In some embodiments, host cells (which may include cells actually transformed although more likely the cells will be descendants of the transformed cells) may be cultured in vitro under conditions for expression of the nucleic acid, so that the encoded serpin polypeptide is produced. When an inducible promoter is used, expression may require the activation of the inducible promoter.

The expressed polypeptide comprising or consisting of the modified serpin may be isolated and/or purified, after production. This may be achieved using any convenient method known in the art. Techniques for the purification of recombinant polypeptides are well known in the art and include, for example HPLC, FPLC or affinity chromatography. In some embodiments, purification may be performed using an affinity tag on the polypeptide as described above.

Another aspect of the invention provides a method of producing a modified serpin comprising expressing a nucleic acid encoding a modified serpin as described above in a host cell and optionally isolating and/or purifying the modified serpin thus produced.

Polypeptides comprising or consisting of a modified serpin produced as described may be investigated further, for example the pharmacological properties and/or activity may be determined. Methods and means of protein analysis are well-known in the art.

A modified serpin as described herein, nucleic acid encoding a modified serpin or a recombinant cell expressing a modified serpin, may be useful in therapy. For example, a modified serpin as described herein, nucleic acid encoding a modified serpin or a recombinant cell expressing a modified serpin may be administered to an individual for the treatment of bleeding.

Whilst a modified serpin may be administered alone, modified serpins will usually be administered in the form of a pharmaceutical composition, which may comprise at least one component in addition to the modified serpin e.g. a nucleic acid encoding the modified serpin or recombinant cell expressing the modified serpin. Thus pharmaceutical compositions may comprise, in addition to the modified serpin, nucleic acid or cell, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by bolus, infusion, injection or any other suitable route, as discussed below.

In some embodiments, modified serpins, nucleic acids or cells may be provided in a lyophilised form for reconstitution prior to administration. For example, lyophilised serpins may be re-constituted in sterile water and mixed with saline prior to administration to an individual.

For parenteral, for example sub-cutaneous or intra-venous administration, e.g. by injection, the pharmaceutical composition comprising the modified serpin, nucleic acid or cell may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG). Suitable carriers, excipients, etc. can be found in standard pharmaceutical texts, for example, Remington's Pharmaceutical Sciences, 18th edition, Mack Publishing Company, Easton, Pa., 1990.

Pharmaceutical compositions and formulations may conveniently be presented in unit dosage form and may be prepared by any methods well known in the art of pharmacy. Such methods include the step of bringing into association the modified serpin with the carrier which constitutes one or more accessory ingredients. In general, the compositions are prepared by uniformly and intimately bringing into association the active compound with liquid carriers or finely divided solid carriers or both, and then if necessary shaping the product.

Preferably, modified serpins, nucleic acids or cells as described herein are formulated in a pharmaceutical composition for intra-venous or sub-cutaneous administration.

A pharmaceutical composition comprising a modified serpin, nucleic acid or cell may be administered alone or in combination with other treatments, either simultaneously or sequentially dependent upon the condition to be treated.

A modified serpin, nucleic acid or cell as described herein may be used in a method of treatment of the human or animal body, including therapeutic and prophylactic or preventative treatment (e.g. treatment before the onset of a condition in an individual to reduce the risk of the condition occurring in the individual; delay its onset; or reduce its severity after onset). The method of treatment may comprise administering a modified serpin to an individual in need thereof.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed. The inhibition of human and murine APC by modified serpins without the inhibition of human or murine thrombin is shown below.

Administration is normally in a "therapeutically effective amount" or "prophylactically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners.

A composition may be administered alone or in combination with other treatments, either simultaneously or sequentially dependent upon the circumstances of the individual to be treated.

Prescription of treatment, e.g. decisions on dosage etc, is within the responsibility of general practitioners and other medical doctors and may depend on the severity of the symptoms and/or progression of a disease being treated. Appropriate doses of therapeutic polypeptides are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of a modified serpin may be determined by comparing its in vitro activity and in vivo activity in an animal model. Methods for extrapolation of effective dosages in mice and other test animals to humans are known. The precise dose will depend upon a number of factors, including whether the modified serpin is for prevention or for treatment, the size and location of the area to be treated, the precise nature of the modified serpin and the nature of any detectable label or other molecule attached to the modified serpin.

A typical modified serpin dose will be in the range of 0.1 mg/kg to 100 mg/kg, for example 1 to 80 mg/kg. For example, a dose in the range 100 μg to 1 g may be used for systemic applications, and 1 μg to 1 mg for topical applications. An initial higher loading dose, followed by one or more lower doses, may be administered. This is a dose for a single treatment of an adult patient, which may be proportionally adjusted for children and infants, and also adjusted for other modified serpin formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the modified serpin composition, the route of administration and the nature of the condition being treated.

Treatment may be periodic, and the period between administrations may be about one week or more, e.g. about two weeks or more, about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of trauma, surgical treatment or invasive procedure. Suitable formulations and routes of administration are described above.

In some embodiments, modified serpins as described herein may be administered as sub-cutaneous injections. Sub-cutaneous injections may be administered using an auto-injector, for example for long term prophylaxis/treatment.

In some preferred embodiments, the therapeutic effect of the modified serpin may persist for several half-lives, depending on the dose.

Modified serpins described herein inhibit APC without inhibiting or substantially inhibiting procoagulant factors, such as thrombin, and may be useful in the treatment of bleeding and bleeding disorders; in particular disorders caused by reduced thrombin generation or increased APC anticoagulant pathway activity.

Hemostasis is the normal coagulation response to injury i.e. the prevention of bleeding or hemorrhage, for example from a damaged blood vessel. Hemostasis arrests bleeding and hemorrhage from blood vessels in the body. Modified serpins may promote hemostasis i.e. they may promote or increase the arrest of bleeding and hemorrhage from blood vessels in the body, for example in individuals with bleeding disorders or trauma.

Aspects of the invention provide; a modified serpin as described herein for use in a method of treatment of the human or animal body; a modified serpin as described herein for use in a method of treatment of bleeding or the promotion of hemostasis; the use of a modified serpin as described herein in the manufacture of a medicament for the treatment of bleeding or the promotion of hemostasis; and a method of treatment of bleeding or the promotion of hemostasis comprising administering a modified serpin as described herein to an individual in need thereof.

Bleeding may include bleeding or hemorrhage from blood vessels in the body.

An individual suitable for treatment with a modified serpin as described herein may have a bleeding disorder.

Bleeding disorders may be caused or associated with reduced thrombin generation or increased activity of the APC anticoagulant pathway.

Bleeding disorders may include any heritable or acquired bleeding disorder in which there is reduced thrombin generation, reduced fibrin clot formation or reduced clot stability. For example, bleeding disorders may include congenital deficiencies of factors VII, VIII, X, IX, XI and XIII; combined V and VIII deficiency; prothrombin deficiency; fibrin deficiency; and rare deficiencies of other clotting factors; hemophilia A, B and C; increased bleeding associated with hyperfibrinolysis; increased bleeding due to reduced platelet count or reduced platelet function; and von Willebrand Disease.

Acquired bleeding disorders may include dilutional coagulopathy associated with major blood loss, bleeding resulting from trauma and surgery and the effects of anticoagulant therapy.

In some embodiments, the individual may be resistant to exogenous coagulation factors, such as exogenous fVIII or fIX. For example, exogenous fVIII or fIX may elicit an immune response in the individual, for example the production of inhibitory alloantibodies.

An individual suitable for treatment with a modified serpin as described herein may have an acquired bleeding disorder, such as bleeding related to trauma, surgery or anti-coagulant therapy. For example, an individual suitable for treatment with a modified serpin as described herein may have suffered a trauma; or may have undergone or be undergoing surgery or anti-coagulant therapy. Suitable individuals may be bleeding or at risk of bleeding from one or more blood vessels in the body.

In some embodiments, a modified serpin as described herein may be useful in the prevention or treatment of i) bleeding in patients with clotting factor alloantibodies; ii) bleeding in patients at high risk of inhibitor development, for example to avoid development of alloantibodies; iii) bleeding in patients with factor VIII deficiency in the absence of inhibitors; iv) bleeding in patients with congenital bleeding disorders, for example a congenital bleeding disorder for which there is no current recombinant optimal replacement therapy, such as severe factor VII deficiency, factor XI deficiency, combined VIII & V deficiency, factor X deficiency and factor V deficiency; v) bleeding in patients with hemophilia, for example patients for whom replacement therapy is inappropriate or unavailable; or vi) acquired bleeding, including bleeding related to trauma, surgery, and anticoagulant therapy.

Other aspects of the invention provide the use of a modified serpin as described herein as a procoagulant and the use of a modified serpin to inhibit APC in the treatment of bleeding.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above and the tables described below.

Table 1 shows second-order rate constants for the inhibition of thrombin and APC by A22 PCI (PCI with an N-terminal truncation, starting at Ala22, numbering uses the mature protein sequence, including the propeptide), FL $\alpha_1$AT Pitts (full length $\alpha_1$AT with the P1R Pittsburgh (Pitts) mutation) and their variants. Standard errors are shown. * The rate constant of inhibition for thrombin by the P2KP1' variant of PCI is an estimate as after initial inhibition, reactions do not appear to approach complete inhibition, potentially due to serpin being shuttled down the substrate pathway or dissociation of the covalent serpin:protease inhibitory complex Table 2 shows second-order rate constants for the inhibition of thrombin and APC by PCI and variants in the presence of heparin. Standard errors are shown. * the rate constant of inhibition for thrombin by the P2KP1'K variant of PCI is an estimate from the initial slope of the plot of residual thrombin activity versus time. Complete inhibition is not achieved, potentially because of serpin being shuttled down the substrate pathway or dissociation of the covalent serpin:protease inhibitory complex.

Table 3 shows second-order rate constants for the inhibition of fXa by $\alpha_1$AT Pitts and PCI and their variants. Standard errors are shown.

Table 4 shows second-order rate constants for the inhibition of fXIa by PCI and the PCI P2KP1'K variant. APC inhibition is shown for comparison (from Table 1). Standard errors are shown.

Table 5 shows second-order rate constants for the inhibition of thrombin and APC by PCI variants generated by targeted random mutagenesis. Standard errors are shown. Constants for WT and P2KP1' PCI are shown for comparison. * The rate constant of inhibition for thrombin by the P2KP1' variant of PCI is an estimate as after initial inhibition, reactions do not appear to approach complete inhibition, potentially due to serpin being shuttled down the substrate pathway or dissociation of the covalent serpin:protease inhibitory complex.

Table 6 shows second-order rate constants for the inhibition of fXIa by FL $\alpha_1$AT Pitts C232S and its P2KP1'K variant. APC inhibition is shown for comparison (from Table 1). Standard errors are shown.

Table 7 shows a fraction of the RCL sequences of the PCI variants determined by targeted random mutagenesis to be specific for APC inhibition over thrombin inhibition. Sequences shown are from an initial experiment in which 88 mutants were assessed. The P4, P2 and P1' residues that were varied in this experiment are shown in bold. WT PCI and P2KP1'K PCI sequences are shown for comparison.

Table 8 shows a fraction of the RCL sequences of the PCI variants determined by targeted random mutagenesis to be specific for APC inhibition over thrombin inhibition. Sequences shown are from a larger experiment in which 460 mutants were assessed. The P4, P2 and P1' residues that were varied in this experiment are shown in bold. WT PCI and P2KP1'K PCI sequences are shown for comparison.

Table 9 shows a fraction of the RCL sequences of the $\alpha_1$AT variants determined by targeted random mutagenesis to be specific for APC inhibition over thrombin inhibition. Sequences are shown compared to both WT $\alpha_1$AT and $\alpha_1$AT Pitts. The P2 and P1' residues are shown in bold, the P1 residues are underlined. Prefixes show the library of origin for the particular mutant with mutants denoted P2.nr coming from the P2 variant library P1'.nr. coming from the P1' variant library and mutants labelled 1-5.nr. coming from plates 1-5 of the P2P1' variant library.

Table 10 shows second-order rate constants for the inhibition of thrombin and APC by a subset of variants of $\alpha_1$AT determined by targeted random mutagenesis to be more specific for APC than for thrombin. Standard errors are given. The second-order rate constants for thrombin and APC inhibition by FL $\alpha_1$AT Pitts C232S P2KP1'K and FL $\alpha_1$AT Pitts C232S are given for comparison.

Table 11 shows the results of PT and aPTT assays to investigate inhibition of procoagulant proteases by hits from random mutagenesis on the FL $\alpha_1$AT Pitts C232S background. PT assays were performed using ¼ diluted plasma to increase the sensitivity of the assay and performed in triplicate, except for the reactions shown for FL $\alpha_1$AT Pitts C232S P2RP1'C, which were performed in duplicate. The error shown is the standard deviation. aPTT assays were single experiments, no error is shown. For both PT and aPTT a buffer only control, where instead of protein, buffer (TBS) was added to the plasma was used as a control. Increases in PT or aPTT with respect to the control are an indication of inhibition of procoagulant proteases. For both PT and aPTT assays, the serpin mutants were used at a 5 µM concentration. For comparison, the P2K and P1'K mutants are shown as an average of triplicates. As shown from inhibition rate constants in Tables 1 and 3, these mutants show high specificity for APC over thrombin, but inhibit fXa significantly. They are therefore good comparator for an inhibition of procoagulant proteases other than thrombin. ND indicates not determined.

Table 12 shows second-order rate constants for the inhibition of fXa by $\alpha_1$AT variants from targeted random mutagenesis. The mutants evaluated here showed specificity for APC over thrombin, substantial APC inhibition and showed no prolongation of the PT. Most also showed only minor aPTT prolongation. Because of these features, they were selected for further analysis. For comparison, fXa inhibition by FL $\alpha_1$AT Pitts C232S and FL $\alpha_1$AT Pitts C232S P2KP1'K is also shown (from Table 3).

Table 13 shows a summary of the characterization of two more mutants of $\alpha_1$AT found by combining information from rational and random mutagenesis. FL $\alpha_1$AT Pitts C232S and FL $\alpha_1$AT Pitts C232S P2KP1'K C232S are shown for comparison (data from Tables 1 and 3 and FIG. 5). aPTTs for P2RP1'Q and P2KP1'Q are the average of four separate measurements, the error shown is the standard deviation. The value obtained for plasma with buffer is shown in brackets, again with the standard deviation shown as the error. The aPTTs shown for Pitts and P2KP1'K are the result of at least three separate measurements, the error shown is the standard deviation. The value shown in brackets is the value obtained for plasma with buffer, shown with the standard deviation as the error. All aPTTs were obtained using a final concentration of 5 µM serpin. FL $\alpha_1$AT Pitts C232S at this concentration rendered the plasma unclottable. The value of 300 s shown is the cut-off for the assay. Second-order rate constants for the inhibition of thrombin, APC and fXa by the variants are shown with the standard error.

Experiments

The coagulation cascade and the regulatory role of serpins in this cascade are shown in FIG. 1. Two pathways lead to activation of the coagulation cascade, the extrinsic cascade (or tissue factor pathway) and the intrinsic pathway (contact activation pathway). The main physiological pathway of activation is believed to be the extrinsic pathway. In this pathway, tissue factor (TF) is exposed on the surface of the damage blood vessel. TF can then bind fVIIa and fVII. TF:fVIIa activates fVII, as well as TF:fVII spontaneously activating to TF:fVIIa. TF:fVIIa activates fX to fXa and this activates prothrombin to thrombin (fIIa); the central protease of the coagulation cascade. Thrombin activates platelets by cleavage of protease activated receptors (PARs) and cleaves fibrinogen to fibrin. Fibrin is crosslinked by fXIIIa, which is itself activated by thrombin, to form the stable fibrin clot. Thrombin in addition activates a positive feedback mechanism to potentiate its own formation. It activates fVIII to fVIIIa and fV to fVa. fVIIIa binds to fIXa to form the intrinsic tenase (Xase) complex. The intrinsic Xase activates more fX. This fXa can bind to fVa to form prothrombinase. Prothrombinase activates prothrombin to thrombin and is responsible for most of the thrombin generated after initiation of coagulation. In addition to thrombin's positive feedback mechanism, thrombin can also shut down its own activation via a negative feedback mechanism. When it binds its cofactor thrombomodulin (TM), the thrombin:TM complex can activate protein C (PC) to activated protein C (APC). APC cleaves and inactivates both fVIIIa and fVa, effectively shutting down thrombin generation. Serpins are important inhibitors of the coagulation cascade. The inhibitory actions of the serpins protein C inhibitor (PCI), antithrombin (ATIII), heparin cofactor II (HCII) and $\alpha_1$-antitrypsin ($\alpha_1$AT) are shown in FIG. 1.

Below we describe the conversion of serpins into specific inhibitors of APC for use as procoagulant agents (treatment, prophylaxis, bypassing or synergistic) in the treatment of bleeding disorders such as hemophilia. The modifications described here for both PCI and $\alpha_1$AT show as a proof of principle that small changes in these proteins can be used to create specific APC inhibitors.

PCI was first described as the physiological inhibitor of APC and therefore served as a starting point for these investigations (Suzuki et al, 1983; 1984). However, PCI is promiscuous and also inhibits thrombin, thrombin:TM, fXIa, fXa and TF:fVIIa (Elisen et al, 1998; Mosnier et al, 2001; Suzuki et al, 1984; Fortenberry et al, 2011; Meijers et al, 1988). As a consequence, PCI can function as both a pro- and an anticoagulant. Its activity is regulated by binding to glycosaminoglycans, such as heparin and heparan sulfates (Pratt & Church, 1992; Pratt et al, 1992; Li & Huntington, 2008). For an overview of the role of PCI in the coagulation cascade, see FIG. 1.

$\alpha_1$AT is the natural inhibitor of neutrophil elastase (Kalsheker, 1989). Unlike other serpins in the coagulation cascade that have either Arg or Leu at P1, $\alpha_1$AT has a Met instead. This makes it a very poor inhibitor of coagulation proteases. Nevertheless, because of the high concentration of $\alpha_1$AT in plasma, it is believed to inhibit APC to a physiologically significant degree (Heeb & Griffin, 1988). Mutagenesis of the P1 residue has shown that the use of an Arg or Leu at P1 drastically improves inhibition of coagulation proteases by $\alpha_1$AT (Heeb et al, 1990). This is exemplified by the Pittsburgh (M358R (P1R); Pitts) variant of $\alpha_1$AT that causes a severe bleeding disorder (Owen et al, 1983).

To develop serpins specific for inhibition of APC over procoagulant proteases, PCI and $\alpha_1$AT Pittsburgh (P1R, $\alpha_1$AT Pitts) were used as template serpin scaffolds. All proteins used in this study were expressed from *Escherichia coli* cultures (Rosetta2(DE3)pLysS, Novagen) using the pETSUMO expression vector (Invitrogen) and purified using a combination of Ni-chromatography, anion-exchange and in the case of PCI, heparin affinity chromatography. The SUMO-tag was subsequently removed by SUMO protease cleavage and the tag removed by tandem Ni-anion exchange chromatography for $\alpha_1$AT Pittsburgh (Pitts, P1R) and tandem anion exchange-heparin chromatography for PCI. The PCI construct is N-terminally truncated, starting at Ala22 (A22, numbering according to the mature protein sequence, starting with the propeptide). The $\alpha_1$AT Pitts (P1R) construct is full-length (FL) and has an additional C232S mutation to abolish intermolecular disulfide bond formation and other modifications during expression and purification (Yamasaki et al, 2011). Due to the expression vector used, the $\alpha_1$AT Pitts construct has a Ser (S) as its first residue instead of a Glu (E). The C232S and E1S mutations are not expected to alter the activity of $\alpha_1$AT.

Lys residues were introduced at different positions into the RCL of PCI and $\alpha_1$AT Pittsburgh and the resulting mutants tested for inhibition of thrombin and APC. In the initial stages of this study, inhibitors were not screened or tested for their inhibition of other coagulation proteases on the premise that once thrombin inhibition was abolished in favor of APC inhibition, the inhibitor could potentially be additionally modified if it had significant residual inhibitory activity towards other coagulation proteases. The RCL residues are numbered according to the Schechter-Berger nomenclature for serpins (Schechter & Berger, 1967).

Rate constants of thrombin and APC inhibition were measured under pseudo-first-order conditions using an excess of serpin over protease (Table 1). Serpin and protease were incubated together for varying lengths of time and the residual activity was determined by adding an excess of chromogenic substrate for the protease (S2238 for thrombin and S2366 for APC). Residual protease activity was then measured by following the absorbance at 405 nm. Plots of residual protease activity over time gave the observed rate constant $k_{obs}$. The second-order rate constant, $k_2$, is the slope of the plot of $k_{obs}$ versus serpin concentration (fitted using a linear regression model). Standard errors of the slope are shown.

The lysine mutations introduced at P2 and P1' were highly effective at increasing the specificity of PCI and $\alpha_1$AT for APC over thrombin for all variants shown in Table 1. Generally, thrombin inhibition was greatly reduced in all cases. APC inhibition was also reduced for all mutants but not nearly to the same degree. Both serpins initially inhibited thrombin better than APC. This was reversed for all mutants tested.

PCI, unlike $\alpha_1$AT, binds heparin and this binding considerably increases its inhibition of thrombin and APC (Pratt & Church, 1992). We therefore tested the inhibition of thrombin and APC by the P1'K and P2KP1'K PCI mutants in the presence of heparin to see if the swap in specificity seen in Table 1 would persist. Rate constants were measured under pseudo-first-order conditions using an excess of PCI over protease. PCI was preincubated with an equimolar concentration of unfractionated heparin for 30 min prior to the experiment. PCI:heparin and protease were incubated together for varying lengths of time and the residual activity after certain timepoints determined by adding an excess of chromogenic substrate for the protease mixed with polybrene to bind the heparin. Plots of residual protease activity over time gave the observed rate constant $k_{obs}$. The second-order rate constant, $k_2$, is the slope of the plot of $k_{obs}$ versus serpin concentration (fitted using a linear regression model). Standard errors of the slope are shown. The value calculated for the inhibition of thrombin by P2KP1'K PCI was an estimate from the initial slope of the plot of residual thrombin activity versus time, as the graph suggests that complete inhibition is not achieved. This might be due to the substrate pathway or complex dissociation. The second-order rate constants are shown in Table 2. As for the inhibition in the absence of heparin, the P1'K and P2KP1'K mutants of PCI, unlike the WT protein were specific for APC over thrombin (Table 2).

These experiments showed that introducing only one or two modifications in the serpin RCL was sufficient to abolish or greatly reduce the inhibition of thrombin both in the presence and absence of cofactors. The inhibition of APC was reduced but still considerable, especially for the variants of $\alpha_1$AT and the PCI variants in the presence of heparin. However, the specificity of PCI and $\alpha_1$AT Pitts is not limited to thrombin and APC. Both these serpins also inhibit fXa, another procoagulant protease. In order not to inhibit coagulation, our variants also need to be specific for APC over fXa. We therefore also determined the rate constants of inhibition of PCI and $\alpha_1$AT and their variants for fXa (Table 3). Rate constants were measured under pseudo-first-order conditions using an excess of serpin over protease. Serpin and protease were incubated together for varying lengths of time and the residual activity determined by adding an excess of chromogenic substrate (S2222) for the protease. Plots of residual protease activity over time gave the observed rate constant $k_{obs}$. The second-order rate constant, $k_2$, is the slope of the plot of $k_{obs}$ versus serpin concentration (fitted using a linear regression model). Standard errors of the slope are shown (Table 3).

As seen before for thrombin, WT PCI inhibited fXa better than APC. $\alpha_1$AT Pitts inhibited APC better than fXa, but the inhibition of fXa was still considerable. The inhibition of fXa was still significant for P1'K PCI, P2K $\alpha_1$AT Pitts and P1'K $\alpha_1$AT Pitts (Table 3). The P2KP1'K variants of $\alpha_1$AT Pitts and PCI were both highly specific for APC over fXa, with absent or negligible inhibition of fXa and were therefore considered lead candidates. The P1'K variant of PCI is also of interest as its inhibition of fXa is very slow in the absence of heparin. The presence of heparin accelerates the rate of APC inhibition significantly, which could potentially skew the specificity ratio in favor of APC.

The PCI lead compounds will be discussed first, followed by the $\alpha_1$AT lead compound.

Figure 2:
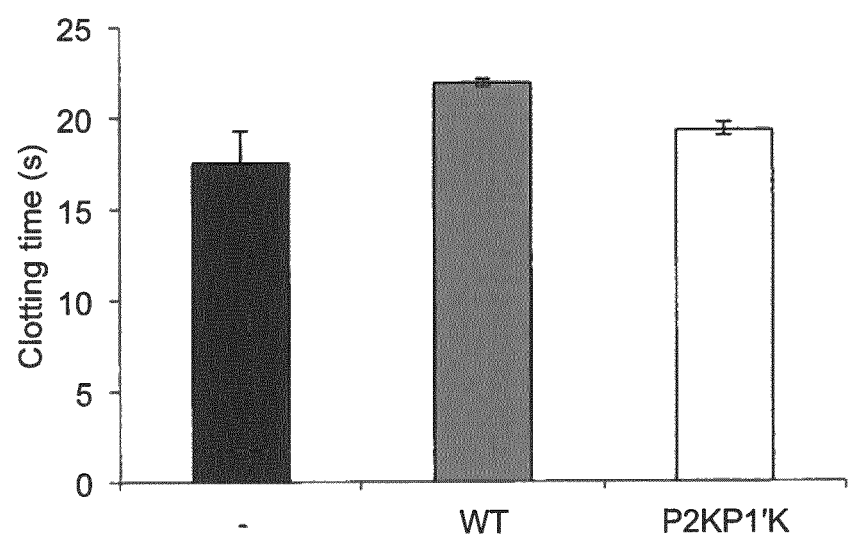
FIG. 2 shows the results of a prothrombin time (PT) assay to determine the effect of Protein C Inhibitor (PCI) with a 21 residue N-terminal truncation (N-terminal residue is A22 of the wild-type sequence, when counting residue 1 of the propeptide as residue 1 of the mature protein) and having K residues at the P2 and P1' positions within the RCL (A22 P2KP1'K PCI) on coagulation through the tissue factor pathway (extrinsic). Pooled normal plasma from three separate plasmas was incubated with either no PCI (black bar, -) or 5 µM A22 wild-type (WT) PCI (grey bar, WT) or 5 µM A22 P2KP1'K PCI (white bar, P2KP1'K). Coagulation was initiated by the addition of PT reagent, to initiate coagulation via the extrinsic pathway and the time until clot formation measured. The assay was performed in triplicate, error bars show the standard deviation. 2-fold diluted plasma was used to increase the sensitivity of the assay for inhibitors of coagulation. A22 P2KP1'K PCI has no effect on coagulation in this prothrombin time (PT) assay. This result indicates that there is no significant inhibition of TF: fVIIa, thrombin and other procoagulant proteases by A22 P2KP1'K PCI.

To investigate the properties of A22 P2KP1'K PCI in a more complex plasma system and to rule out any negative effects on the procoagulant proteases, a prothrombin time assay (PT) was performed. This assay measures the time until clot formation in plasma after coagulation is initiated via the extrinsic pathway. A22 WT PCI showed a small increase in the clotting time, whereas P2KP1'K showed a smaller increase, consistent with reduced inhibitory activity towards procoagulant proteases (FIG. 2).

In addition, we wanted to rule out any effect of the PCI mutant on the contact activation pathway of coagulation. To do so, rate constants of inhibition were measured for the inhibition of fXIa and an aPTT assay was done. This assay is similar to the PT assay except that it measures coagulation initiated via the intrinsic pathway.

Second-order rate constants of inhibition for inhibition of fXIa by PCI and the P2KP1'K variant were measured under pseudo-first-order conditions using an excess of serpin over protease. Serpin and protease were incubated together for varying lengths of time and the residual activity determined by adding an excess of chromogenic substrate for the protease (S2366). Plots of residual protease activity over time gave the observed rate constant $k_{obs}$. The second-order rate constant, $k_2$, is the slope of the plot of $k_{obs}$ versus serpin concentration (fitted using a linear regression model). Standard errors of the slope are given. fXIa inhibition by A22 P2KP1'K PCI did not go to completion over the course of the experiment, potentially due to serpin cleavage by the protease. Compared to WT, the P2KP1'K mutant showed a much reduced inhibition towards fXIa and greater specificity for APC than for fXIa (Table 4).

Figure 3:
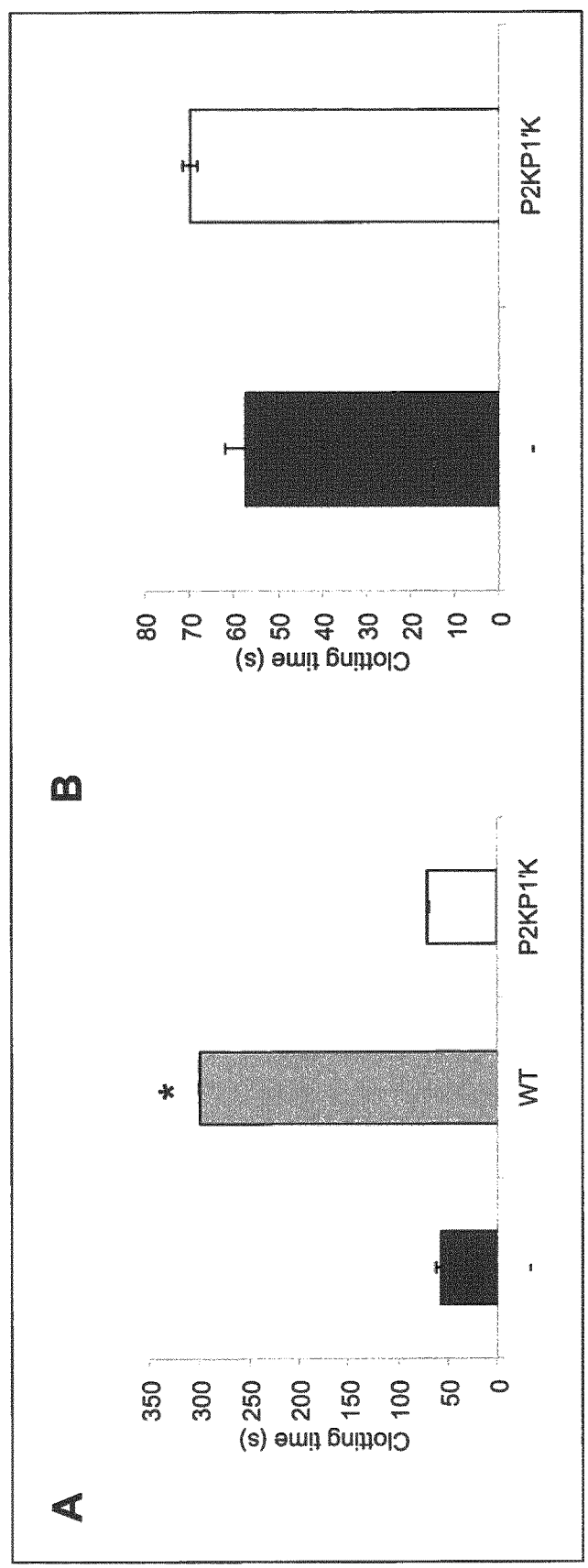
FIG. 3 shows the results of an activated partial thromboplastin time (aPTT) assay to determine the effect of A22 P2KP1'K PCI on coagulation through the contact activation pathway (intrinsic).
Figure 4:
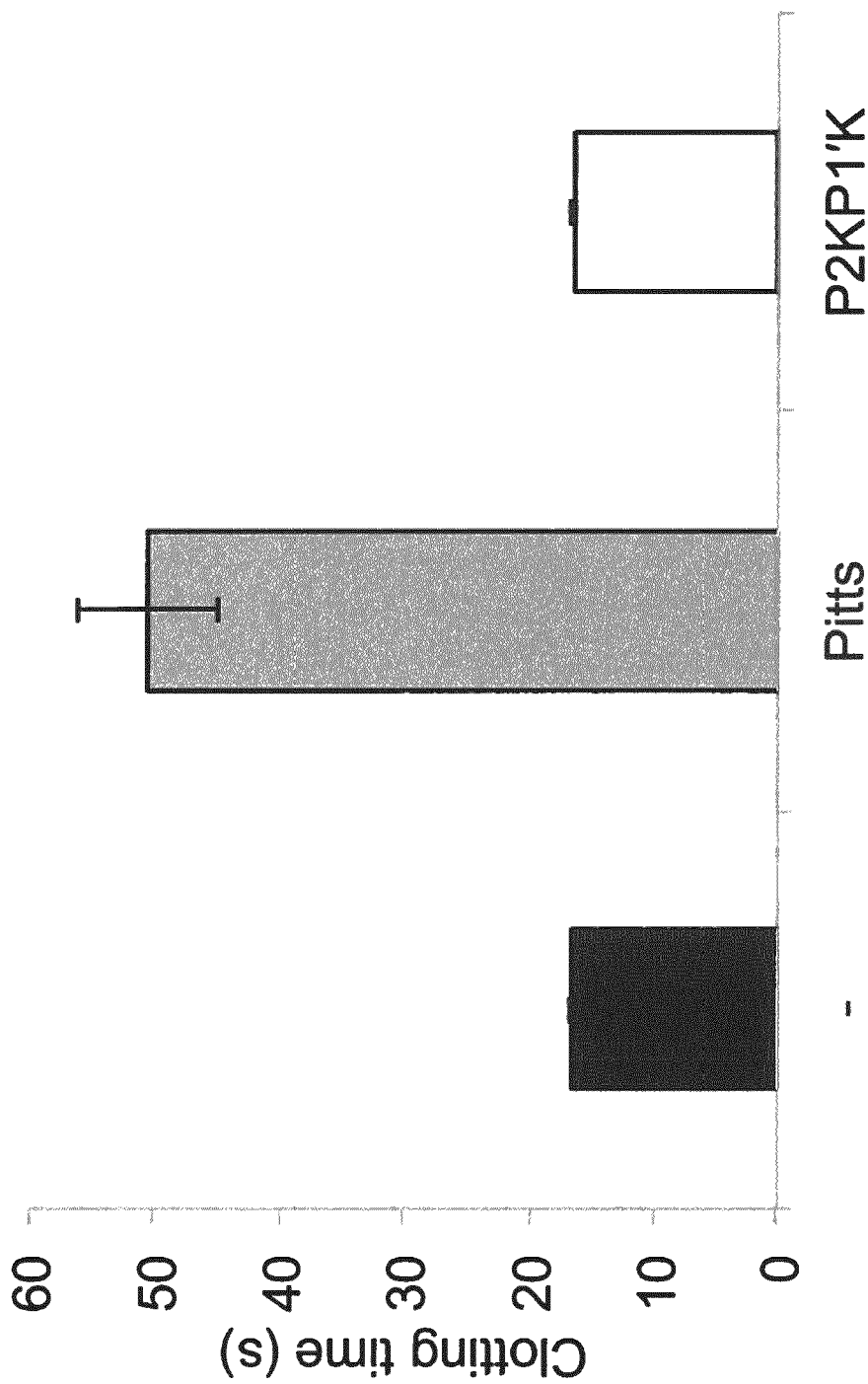
FIG. 4 shows the results of a prothrombin time assay (PT) determining the effect of a full-length (FL) $\alpha_1$-antitrypsin Pittsburgh (Pitts) mutant (M358R=P1R) that further comprises a C232S mutation and P357K (P2) and S359K (P1'K) mutations within the RCL (FL $\alpha_1$AT Pitts C232S P2KP1'K) on coagulation through the tissue factor pathway (extrinsic). Pooled normal plasma from three separate plasmas was incubated with either no $\alpha_1$AT (-, black bar) or 5 μM FL $\alpha_1$AT Pitts C232S (Pitts, grey bar) or 5 μM FL $\alpha_1$AT Pitts C232S P2KP1'K (P2KP1'K, white bar). Coagulation was initiated by the addition of PT reagent and the time until clot formation measured. Bars show averages of at least three measurements, error bars show the standard deviation. 2-fold diluted plasma was used to increase the sensitivity of the assay for inhibitors of coagulation. FL $\alpha_1$AT Pitts C232S P2KP1'K, unlike FL $\alpha_1$AT Pitts C232S does not prolong the PT. This indicates there is no significant inhibitory effect towards any of the procoagulant proteases, including TF-fVIIa, thrombin, or fXa.

The aPTT assay showed that WT PCI was a potent inhibitor of the contact activation pathway, potentially due to inhibition of fXIa or fXIIa (FIG. 3). The P2KP1'K mutant showed a small increase in the aPTT. However, since the contact activation pathway primarily activates coagulation through fIXa activation, inhibition of contact activation to a small extent is likely to be insignificant in hemophiliacs as they are deficient in either the main target of contact activation (fIX) or its cofactor (fVIII).

The results shown here so far therefore show that both A22 P1'K PCI and A22 P2KP1'K PCI are promising, APC-specific lead compounds for development into bypassing agents for the treatment of hemophilia.

To generate additional PCI mutants with specificity for APC over thrombin, a targeted random mutagenesis strategy was employed on the PCI scaffold. The residues targeted were P4, P2 and P1'. The random approach is based on a selection for APC inhibition and against thrombin inhibition by testing inhibitory activity of bacterial lysates, after PCI expression in a 96-well format.

Figure 5A:
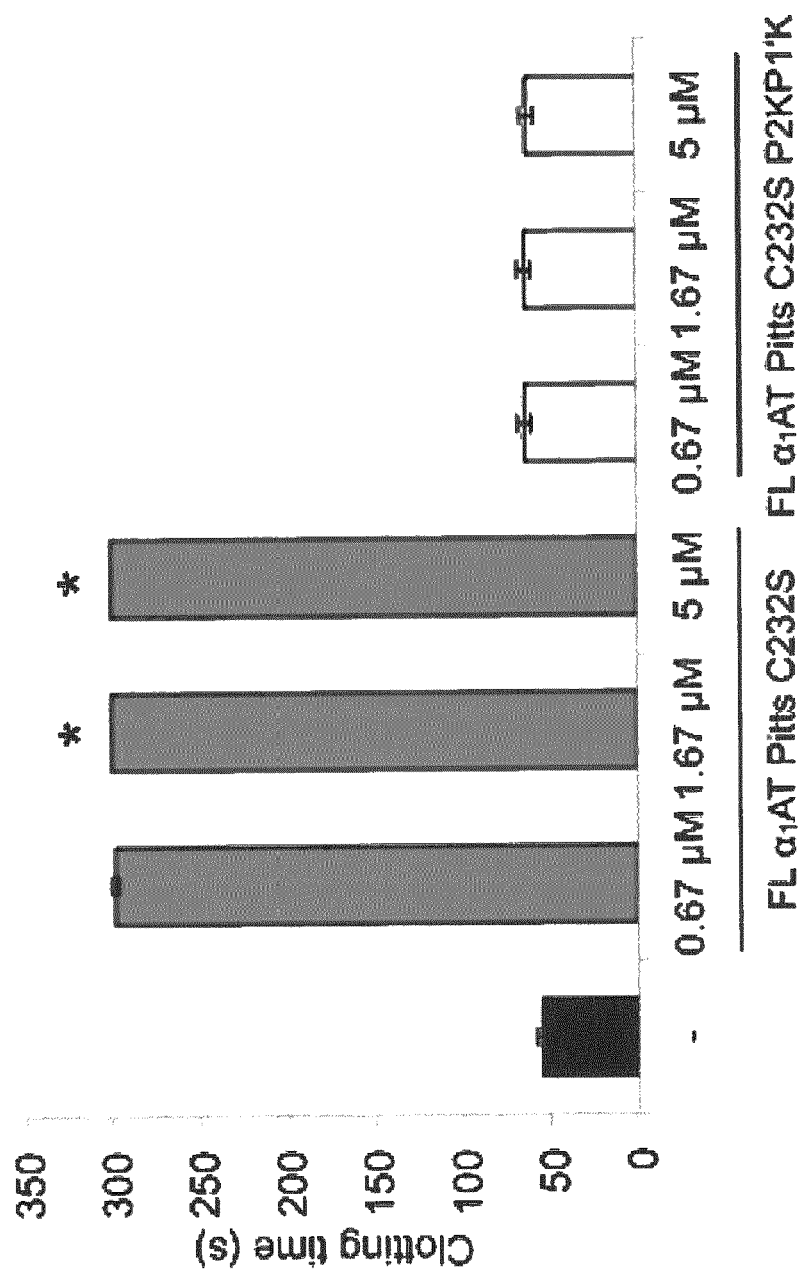
FIG. 5A shows pooled normal plasma from three separate plasmas incubated with either no $\alpha_1$AT (black bar) or increasing concentrations of FL $\alpha_1$AT Pitts C232S (grey bars) or FL $\alpha_1$AT Pitts C232S P2KP1'K (white bars). aPTT reagent was added and the samples incubated for 5 min at 37° C. Coagulation was then initiated by the addition of $CaCl_2$ and the time until clot formation measured. Bars show averages of at least three measurements, error bars show the standard deviation. The assay was stopped at 300 s. Samples shown at 300 s did not clot within the time of the experiment and are marked with asterisks.
Figure 5B:
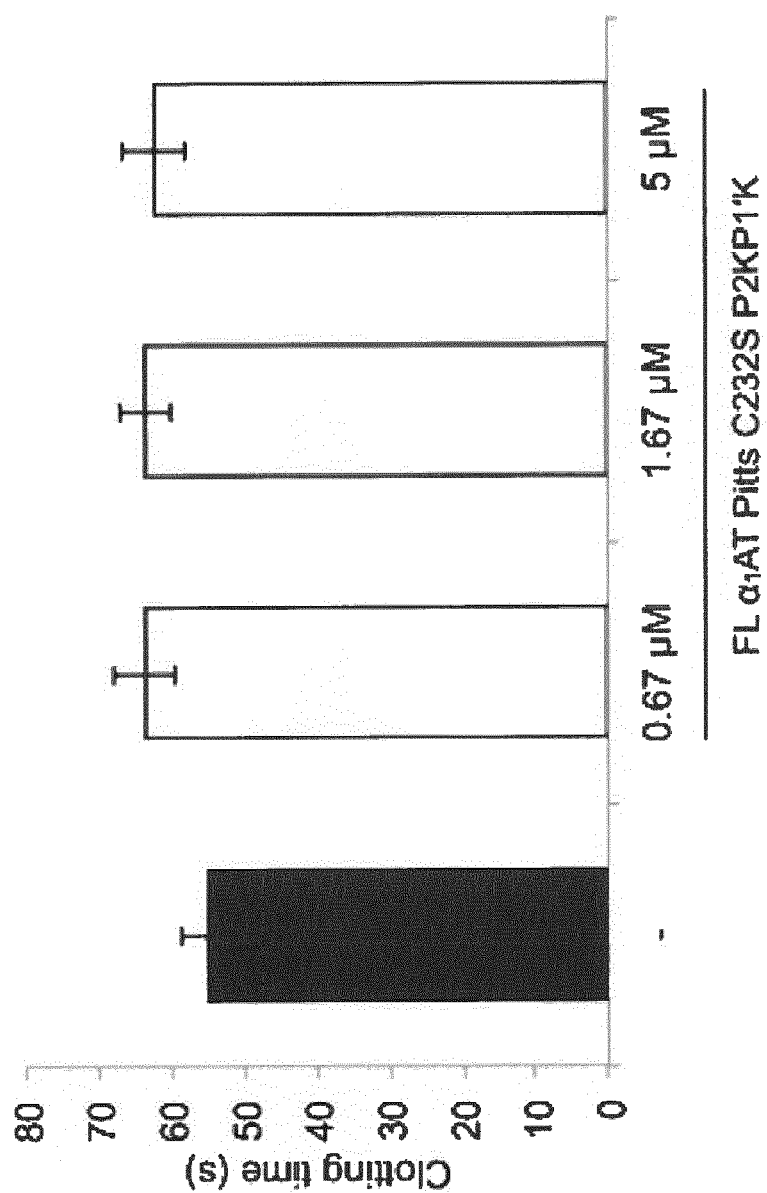
FIG. 5B shows the data from A without FL $\alpha_1$AT Pitts C232S samples to show a small effect on the clotting time by FL $\alpha_1$AT Pitts C232S P2KP1'K. However, this effect does not increase dose-dependently.
Figure 6A:
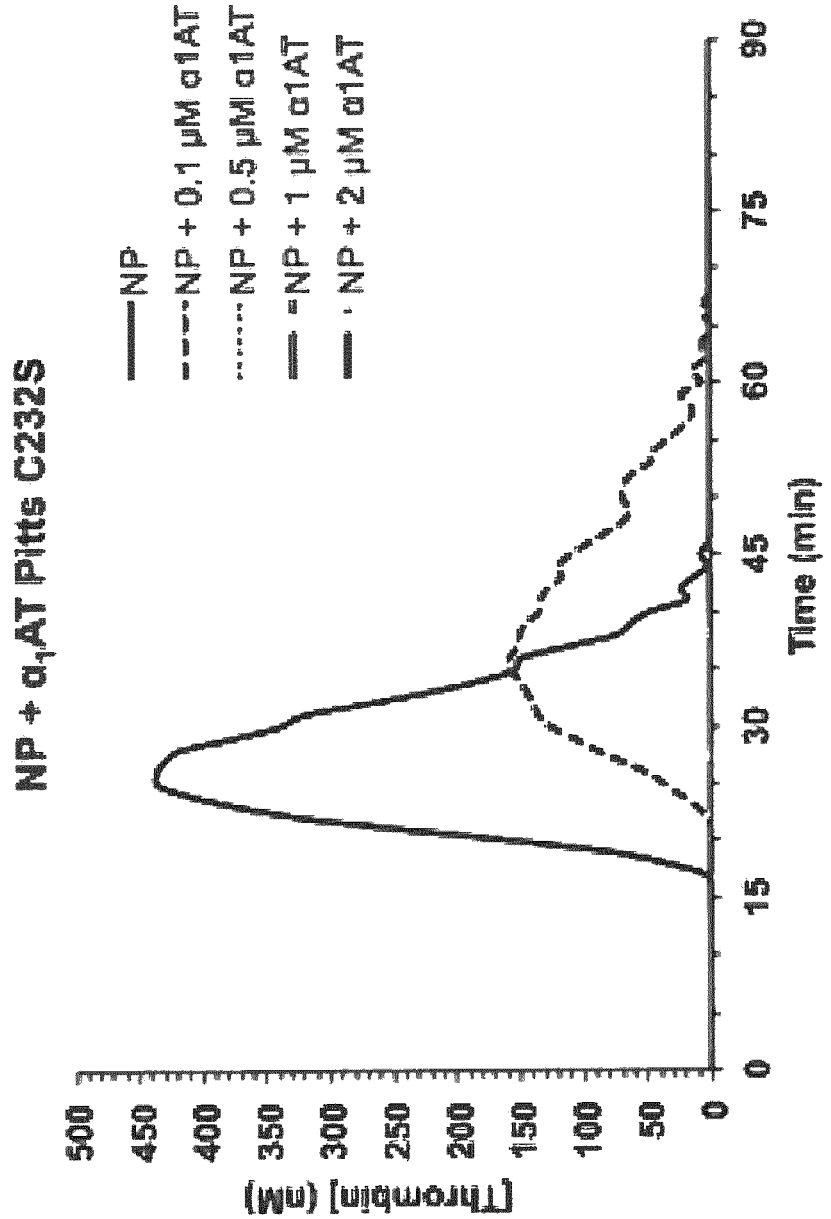
FIG. 6 shows that FL $\alpha_1$AT Pitts C232S inhibits thrombin generation in normal human plasma (NP). Figs A-C show representative thrombin generation curves for reactions containing increasing concentrations of FL $\alpha_1$AT Pitts C232S in the presence of (A) no thrombomodulin (TM) (B) 1.25 nM thrombomodulin (TM) (C) 10 nM thrombomodulin (TM). Curves show an average of duplicates. All assays were performed in pooled normal human plasma (NP) from George King Biomedical. Coagulation was initiated by the addition of $CaCl_2$ and TF/phospholipid (RB low TF and phospholipid reagent #5006210, Technoclone GmbH) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone).
FIG. 6D shows mean ETPs (endogenous thrombin potentials), representing the total amount of thrombin generated during the reactions. Bars show the mean of two independent experiments performed in duplicate. Error bars represent the standard deviation. The thrombomodulin (TM) used was recombinantly produced from HEK-EBNA cells and consists of the extracellular domain of TM.
Figure 6B:
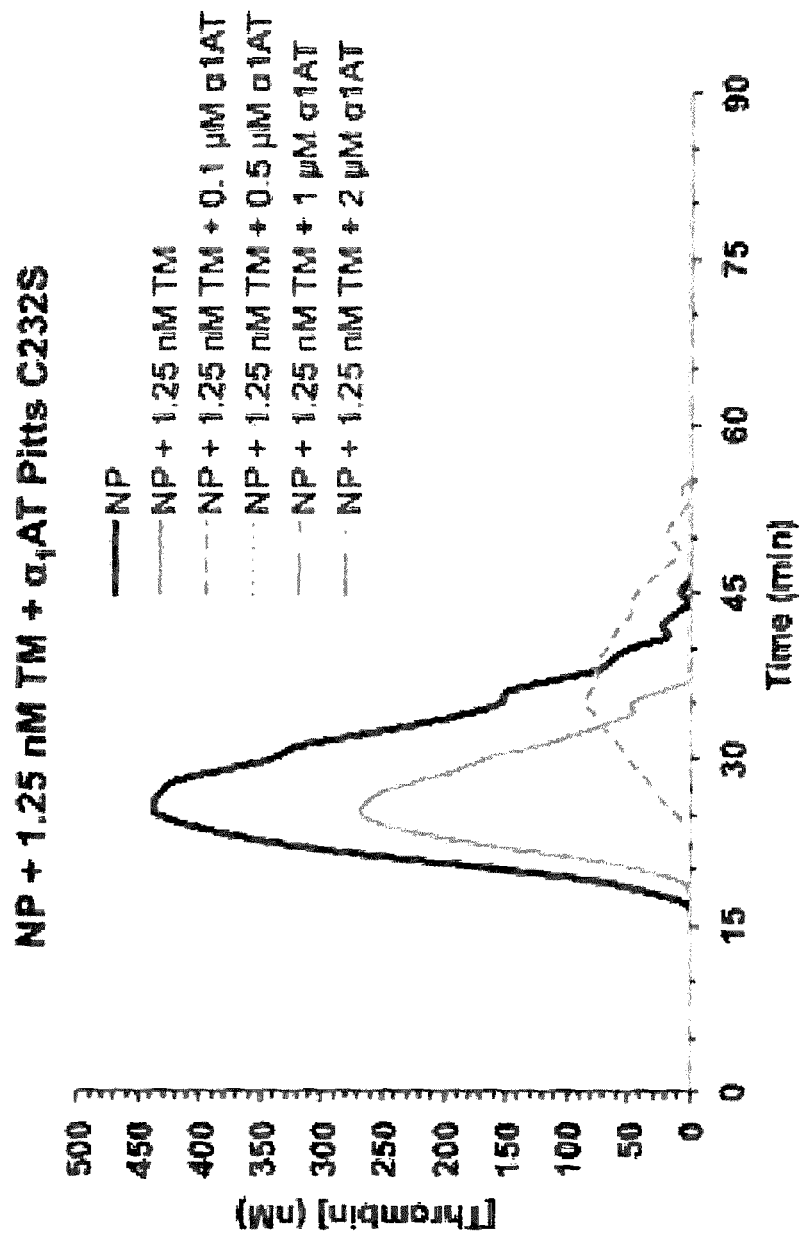
Figure 6C:
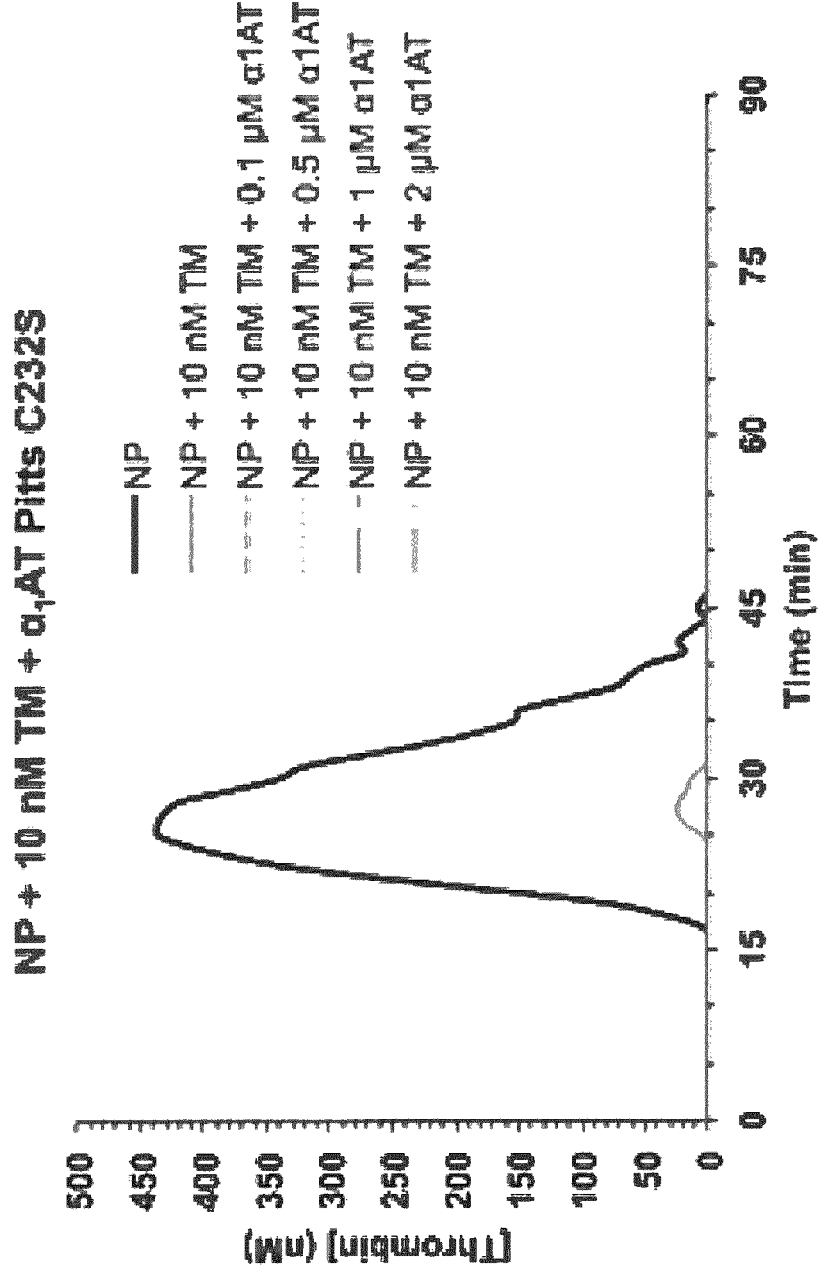
Figure 6D:
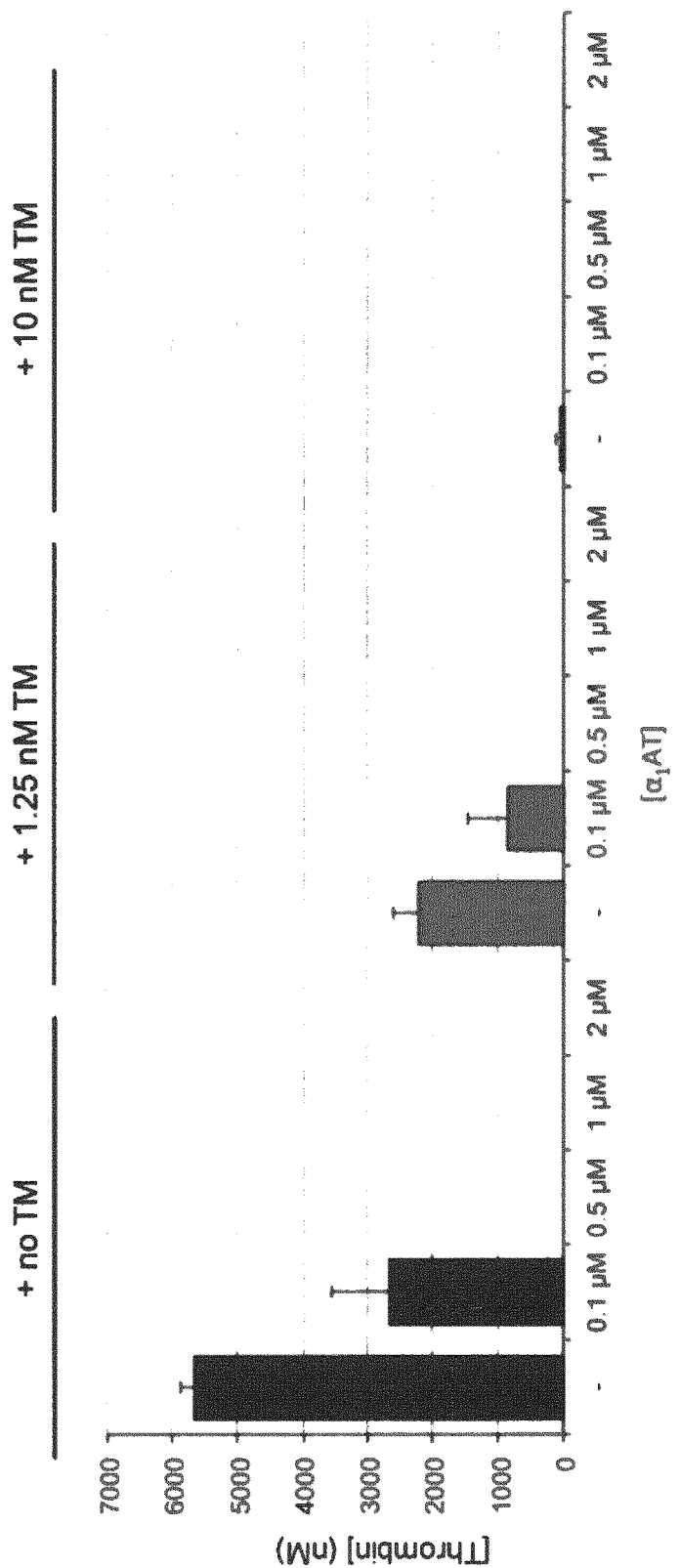

The assay was calibrated using the most specific PCI mutant generated from the rational mutagenesis combined with the testing for specificity outlined above; A22 P2KP1'K PCI. WT PCI was used as an additional control. The negative selection against inhibition of thrombin was achieved by incubating bacterial lysates for a time period such that A22 WT PCI showed complete inhibition and the incubation period extended from that timepoint on to also select against minor inhibition. Positive selection for APC inhibition was calibrated such that both WT and P2KP1'K PCI fell into the intermediate range of APC inhibitory activity so we would be able to determine both increases as well as decreases in inhibition.

In an initial assay, 88 variants were screened for thrombin and APC inhibitory activity. Cultures were grown, induced and protein expressed in 96-well plates. Cells were lysed by the addition of a lysis buffer and the lysates assayed for inhibitory activity against thrombin and APC by incubating the lysate with the protease for 1 h for thrombin and 30 min for APC. Residual protease activity was then read by addition of a chromogenic substrate to the protease. A22 WT PCI and A22 P2KP1'K PCI were used as controls. Any lysate with higher or equivalent residual thrombin activity and lower or equivalent residual APC activity compared to P2KP1'K PCI was considered to be a promising APC-specific candidate. These sequences are shown in Table 7. P4, P2 and P1' positions are shown in bold.

The mutant with the greatest APC inhibitory activity from this set of experiments (D8; P4QP2RP1'N) was characterized in a preliminary fashion and was shown to be more specific for the inhibition of APC than thrombin, whilst utilizing different mutations than P2KP1'K (Table 5). This indicated that it would be possible to make additional mutations in the serpin RCL, which would have equivalent effects to the mutations already described.

To generate a larger dataset, a further 460 mutants were screened in both the positive and negative selection assays. Cultures were grown, induced and protein expressed in five 96-well plates. Cells were lysed by the addition of a lysis buffer and the lysates assayed for inhibitory activity against thrombin and APC by incubating the lysate with the protease for 1 h for thrombin and 30 min for APC. Residual protease activity was then read by addition of a chromogenic substrate to the protease (S2238 for thrombin, S2366 for APC). A22 WT PCI and A22 P2KP1'K PCI were used as controls. Any lysate with higher or equivalent residual thrombin activity and lower or equivalent residual APC activity compared to P2KP1'K PCI was considered to be a promising APC-specific candidate. From this dataset, colonies were picked and sequenced for serpins that showed better inhibition of APC and worse or equivalent inhibition of thrombin than P2KP1'K and these were retested in triplicate in the same assay to verify that these were indeed true hits and not false positives. From this retest a set of 15 out of the 17 mutants found in the initial screen was determined to be better or equivalent at inhibiting APC than P2KP1'K and worse or equivalent at inhibiting thrombin (Table 8). Sequences of variants that were positive after retesting are shown in Table 8. Interestingly, the random mutagenesis confirmed the beneficial effects of positively charged residues in the P2 and P1' positions. However alternative RCL compositions were also found.

Preliminary second-order rate constants for the inhibition of thrombin and APC by random mutagenesis PCI variants were measured under pseudo first-order conditions using an excess of serpin over protease. Serpin and protease were incubated together for varying lengths of time and the residual activity determined by adding an excess of chromogenic substrate for the protease. Plots of residual protease activity over time gave the observed rate constant $k_{obs}$. The second-order rate constant, $k_2$, is the slope of the plot of $k_{obs}$ versus serpin concentration (fitted using a linear regression model). WT and P2KP1'K are shown for comparison. Rate constants are shown in Table 5. The error shown is the standard error of the slope.

Preliminary characterization of some of the selected mutants from the random mutagenesis assay showed that the selected mutants were at least functionally equivalent to P2KP1'K PCI, and some had a slightly improved rate of APC inhibition (Table 5). These experiments strongly suggest that P2KP1'K is not the only composition which could be utilized to generate APC-specific serpins.

The main lead compound based on $\alpha_1$AT Pitts from the rate constants shown in Tables 1 and 3 was FL $\alpha_1$AT Pitts C232S P2KP1'K. This mutant was shown not to inhibit thrombin and only slowly inhibited fXa, but retained APC inhibition (Tables 1 and 3).

To investigate the properties of this mutant in a more complex plasma system and to rule out any negative effects on the procoagulant proteases, a prothrombin time assay (PT) was performed. This assay measures the time until clot formation after coagulation is initiated via the extrinsic pathway. As expected, the anticoagulant $\alpha_1$AT Pitts showed an increase in clotting time, due to its inhibition of thrombin and fXa (FIG. 4). In contrast, the P2KP1'K mutant of $\alpha_1$AT Pitts showed no increase in clotting time and therefore did not interfere with normal coagulation in this assay.

The data so far indicated that the P2KP1'K mutant of $\alpha_1$AT Pitts did not interfere with procoagulant proteases in either the extrinsic (tissue factor) pathway or the common pathway of coagulation. In addition we wanted to determine whether FL $\alpha_1$AT Pitts C232S P2KP1'K affected the intrinsic (contact activation) pathway. Second-order rate constants of inhibition of fXIa by FL $\alpha_1$AT Pitts C232S and the P2KP1'K variant were measured under pseudo first-order conditions using an excess of serpin over protease. Serpin and protease were incubated together for varying lengths of time and the residual activity determined by adding an excess of chromogenic substrate for the protease (S2366). Plots of residual protease activity over time gave the observed rate constant $k_{obs}$. The second-order rate constant, $k_2$, is the slope of the plot of $k_{obs}$ versus serpin concentration (fitted using a linear regression model). Standard errors of the slope are given.

fXI is activated during the contact activation pathway and it feeds into the common pathway of coagulation by activating fIX. In addition, fXI is activated once coagulation is initiated by thrombin. fXIa was inhibited to a significant degree by FL $\alpha_1$AT Pitts C232S, however this inhibition was greatly reduced for FL $\alpha_1$AT Pitts C232S P2KP1'K (Table 6).

Because a small degree of inhibition of fXIa by the P2KP1'K mutant of $\alpha_1$AT Pitts was detected and to determine any potential negative effect on fXIIa, we additionally performed an aPTT assay. This assay is similar to the PT assay except that it measures coagulation initiated via the intrinsic pathway of coagulation. The aPTT could therefore be used to detect any negative effect on fXIa and the contact activation pathway of coagulation. In this assay, plasma incubated with FL $\alpha_1$AT Pitts C232S did not clot within the time of the assay except for one reaction with 0.67 µM serpin (FIG. 5A). FL $\alpha_1$AT Pitts C232S P2KP1'K showed a small increase in clotting time, but there was no dose-dependent increase (FIG. 5B). This indicates that the fXIa inhibitory activity of FL $\alpha_1$AT Pitts C232S P2KP1'K is likely too slow to significantly affect the contact activation pathway. In addition, the contact activation pathway activates the coagulation cascade via activation of fIXa. Since hemophiliacs lack either fIX or its essential cofactor fVIII, the role of a small degree of inhibition of the contact activation pathway in hemophiliacs is likely to be minimal.

To investigate whether the P2KP1'K mutant of $\alpha_1$AT Pitts was able to inhibit APC in a plasma system, we used a modified thrombin generation assay (TGA). Thrombin generation was measured in human pooled normal plasma (NP) in the presence and absence of recombinant soluble thrombomodulin (TM). This TM was expressed and purified from a HEK-EBNA expression system and comprises the soluble extracellular domain. TM is not normally present in the TGA because physiologically it is a transmembrane protein, present on the endothelial membrane and largely absent from plasma. Therefore, there is no activation of the PC pathway in a normal TGA or other coagulation assays utilizing plasma, such as the PT and aPTT assays. Adding TM to the assay allows PC activation and thereby might give a more realistic picture of thrombin generation in vivo. Assays shown in FIGS. 6 and 7 were performed in pooled normal human plasma (NP) from George King Biomedical. Coagulation was initiated by the addition of $CaCl_2$ and TF/phospholipid (RB low TF and phospholipid reagent, Technoclone) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone).

Addition of TM to pooled normal plasma reduced thrombin generation in a concentration-dependent manner. From this experiment we chose two concentrations of TM to knock down thrombin generation to either intermediate levels (1.25 nM TM final assay concentration) or to low levels (10 nM TM final assay concentration). These concentrations were used in subsequent assays to evaluate the ability of FL $\alpha_1$AT Pitts C232S P2KP1'K to inhibit APC in plasma.

Figure 7A:
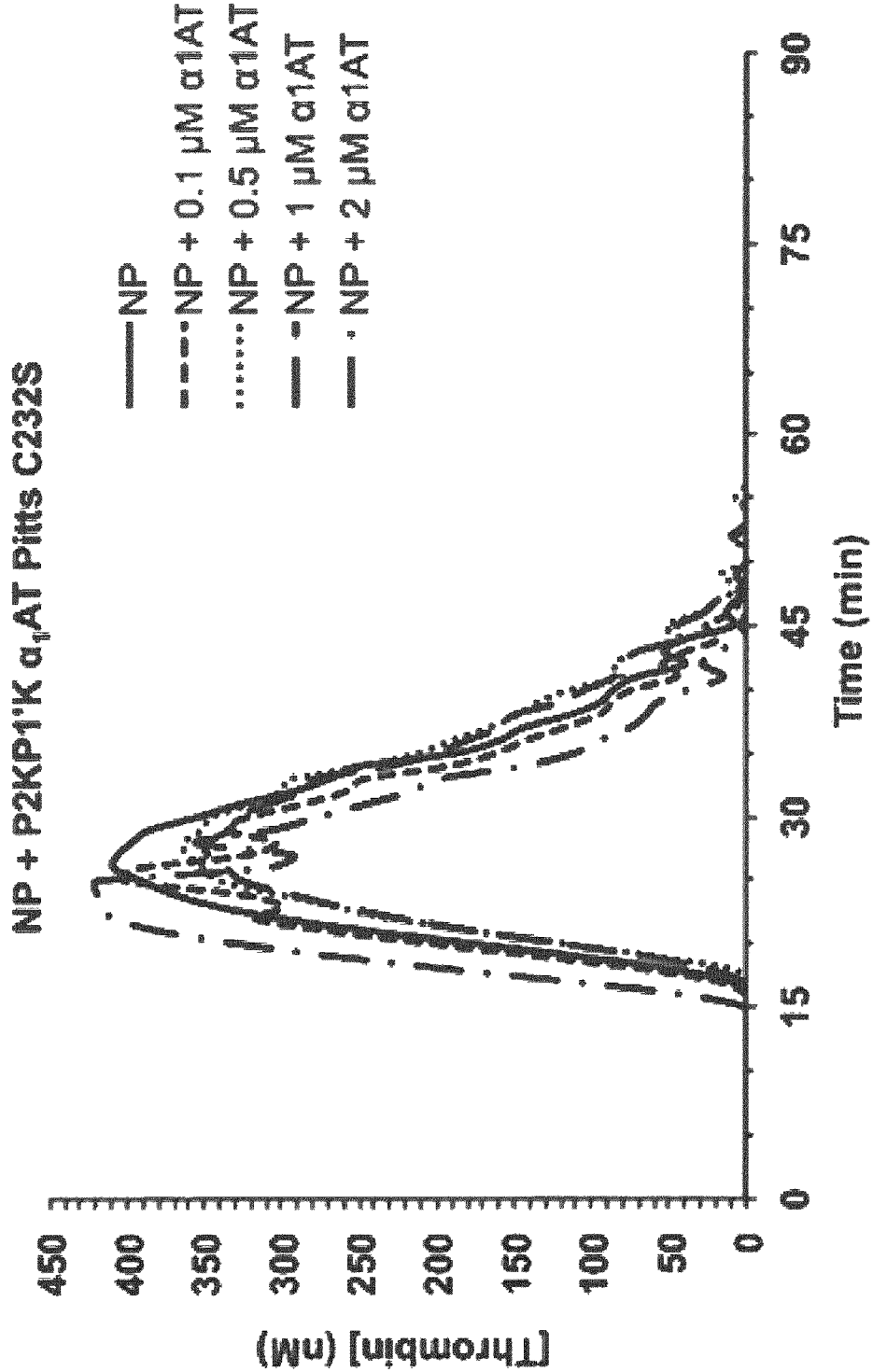
FIG. 7A-C show representative thrombin generation curves for reactions containing increasing concentrations of FL $\alpha_1$AT Pitts C232S P2KP1'K in the presence of (A) no TM (B) 1.25 nM TM (C) 10 nM TM. Curves show an average of duplicates. All assays were performed in pooled normal human plasma (NP) from George King Biomedical. Coagulation was initiated by the addition of $CaCl_2$ and TF/phospholipid (RB low TF and phospholipid reagent #5006210 Technoclone GmbH) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone GmbH).
Figure 7B:
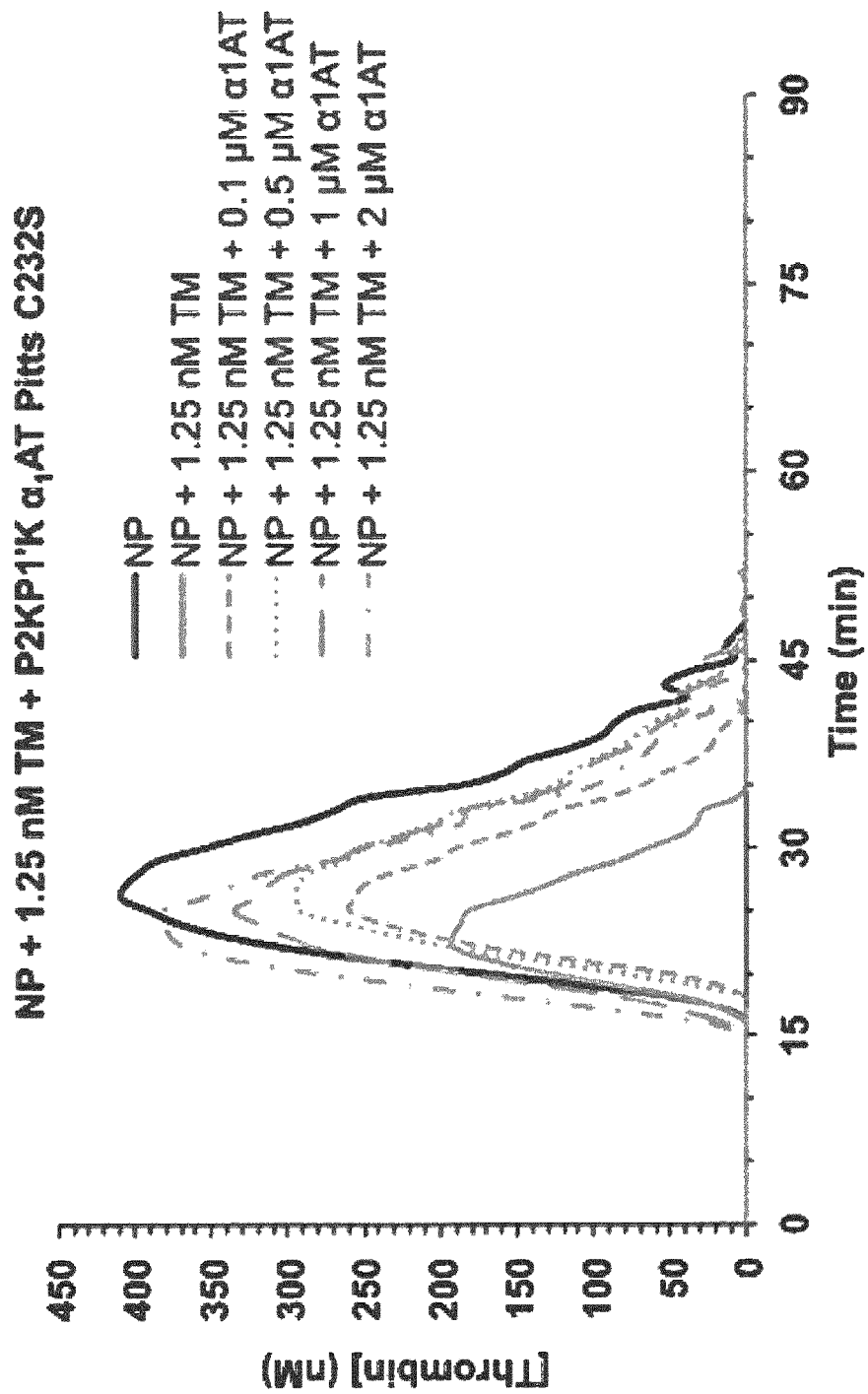
Figure 7C:
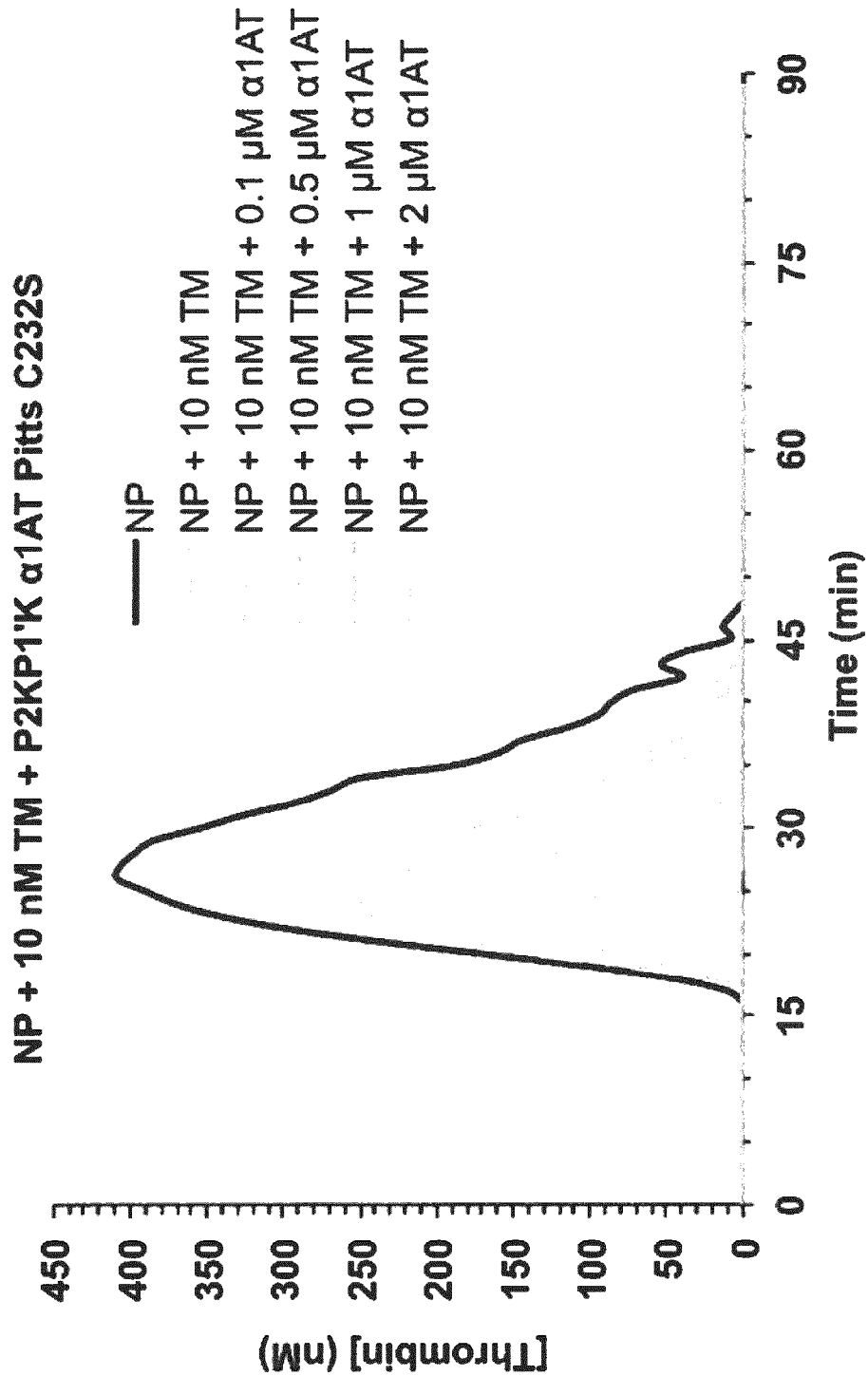
Figure 7D:
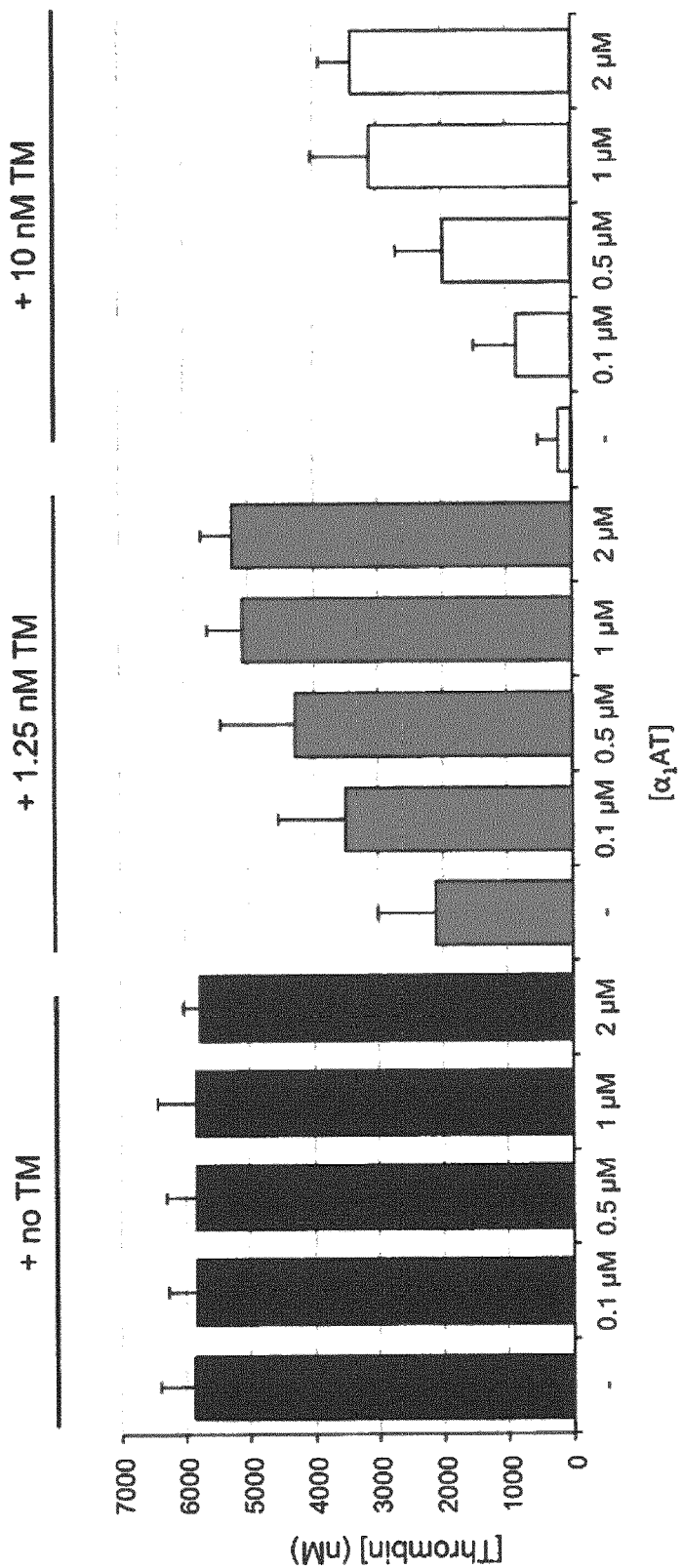
FIG. 7D shows mean ETPs (endogenous thrombin potentials), representing the total amount of thrombin generated during the reactions. Bars show the mean of three independent experiments performed in duplicate. Error bars represent the standard deviation.

Addition of FL $\alpha_1$AT Pitts C232S to normal human plasma (NP) reduced thrombin generation at all concentrations used, likely due to the inhibition of thrombin as well as fXa (FIG. 6). In contrast, FL $\alpha_1$AT Pitts C232S P2KP1'K had no effect on NP in the absence of TM (FIG. 7A). However in the presence of TM, FL $\alpha_1$AT Pitts C232S P2KP1'K dose-dependently rescued thrombin generation (FIG. 7B-D). This effect is the result of specific inhibition of APC by FL $\alpha_1$AT Pitts C232S P2KP1'K.

In order to perform the same experiments in fVIII- or fIX-deficient plasma, it was necessary to increase the amount of tissue factor (TF) used to initiate the assay because at the baseline conditions (RB trigger only), there was no detectable thrombin generation in factor deficient plasma. To demonstrate the effect of an increase in TF on thrombin generation, the reactions were spiked with different dilutions of TF reagent (Dade Innovin, Siemens) in addition to the RB reagent used to trigger the assay at baseline conditions. The concentration of TF in the Innovin reagent is not disclosed by the manufacturer, however previous measurements have shown it to be around 7.36 nM (Duckers et al, 2010). Increasing the TF trigger shortened lag-time and increased both peak thrombin and endogenous thrombin potential (ETP) in human NP, fVIII-deficient (HA) and fIX-deficient (HB) plasma. From these experiments we chose an Innovin dilution of 1:4,000 in the final reaction to initiate thrombin generation. RB reagent, which contains both phospholipids and TF was added because of the need to add phospholipids to the assay.

Because the use of factor-deficient plasma required modification of the assay parameters, we repeated the TM titration experiment for human normal pooled plasma in human HA plasma with the addition of 1:4,000 Innovin. The assay was performed in human fVIII-deficient plasma (less than 1% fVIII activity) from George King Biomedical. Coagulation was initiated by the addition of $CaCl_2$ and/or TF/phospholipid (RB low TF and phospholipid reagent, Technoclone) with 1:4,000 final dilution of Dade Innovin (Siemens) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone). Thrombomodulin (TM) was found to reduce thrombin generation in the thrombin generation assay (TGA) in fVIII-deficient plasma (HA).

From this experiment, 1.25 nM and 5 nM TM were selected for subsequent experiments. The high TM concentration used was lower than for NP, mainly because the total thrombin generation in HA plasma in the assay conditions used was lower.

Figure 8:
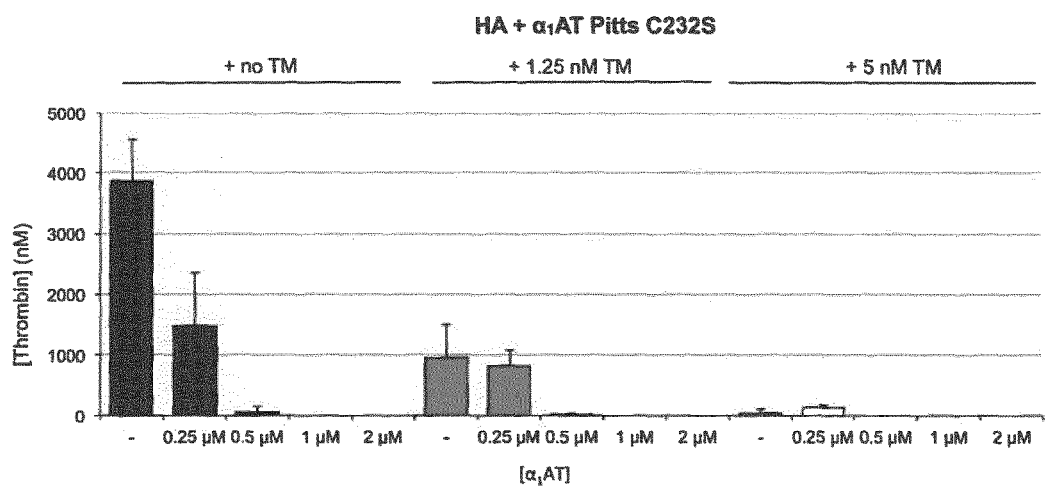
FIG. 8 shows that FL $\alpha_1$AT Pitts C232S abolishes thrombin generation in human hemophilia A plasma (HA, fVIII-deficient), and human hemophilia B plasma (HB, fIX-deficient). Graphs show the mean ETPs from thrombin generation experiments spiked with increasing concentrations of FL $\alpha_1$AT Pitts C232S in either (A) fVIII-deficient plasma (less than 1% fVIII activity) or (B) fIX-deficient plasma (less than 1% fIX activity) with the indicated amounts of added thrombomodulin (TM). All plasmas were from George King Biomedical. Reactions were initiated by adding $CaCl_2$ and TF/phospholipid (RB low TF and phospholipid reagent #5006210 Technoclone GmbH) with 1:4,000 final dilution of Dade Innovin (Siemens) to activate coagulation through the extrinsic pathway. Thrombin generation was measured through the cleavage of a fluorogenic substrate (Z-Gly-Gly-Arg-AMC). Fluorescence units were converted to thrombin concentration by calibrating fluorescence units against known concentrations of thrombin, using the Technothrombin calibration kit (Technoclone).
Figure 8:
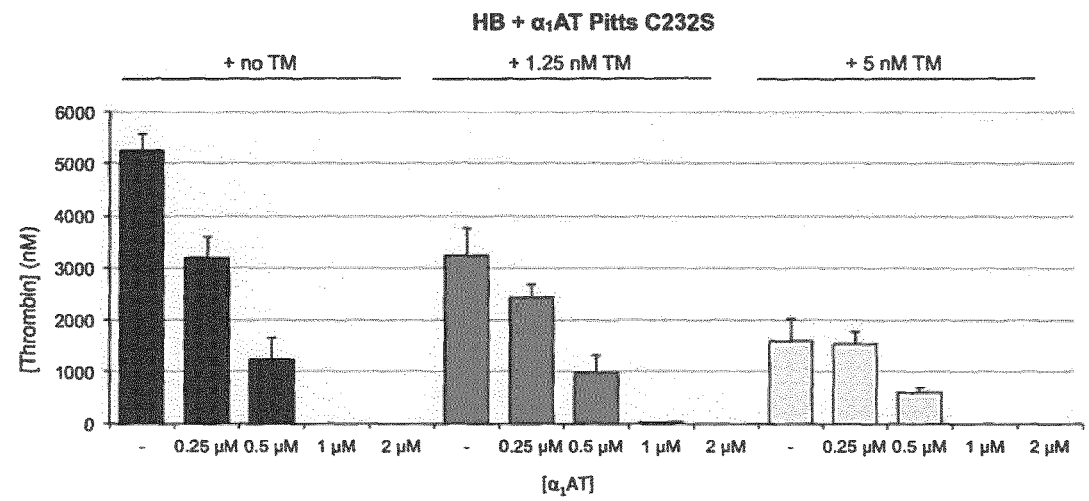
Figure 9A:
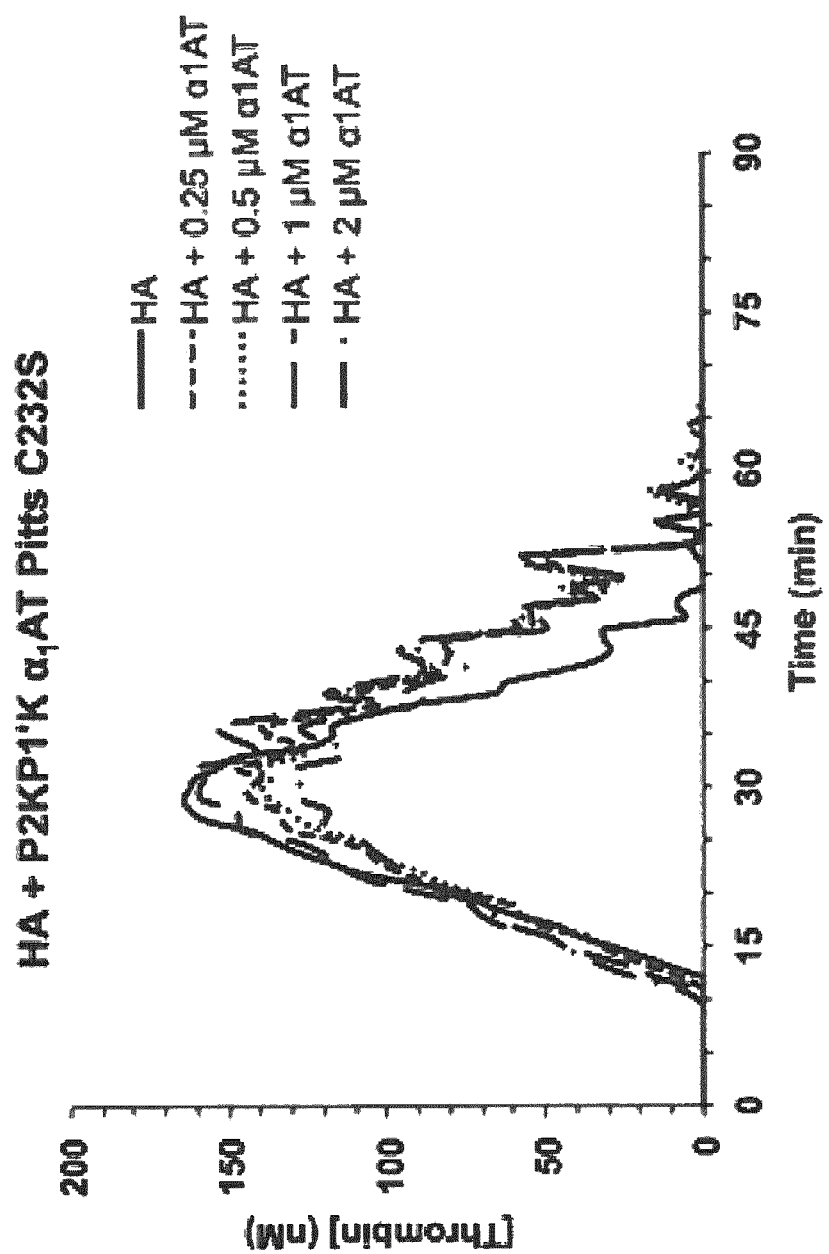
Figure 9B:
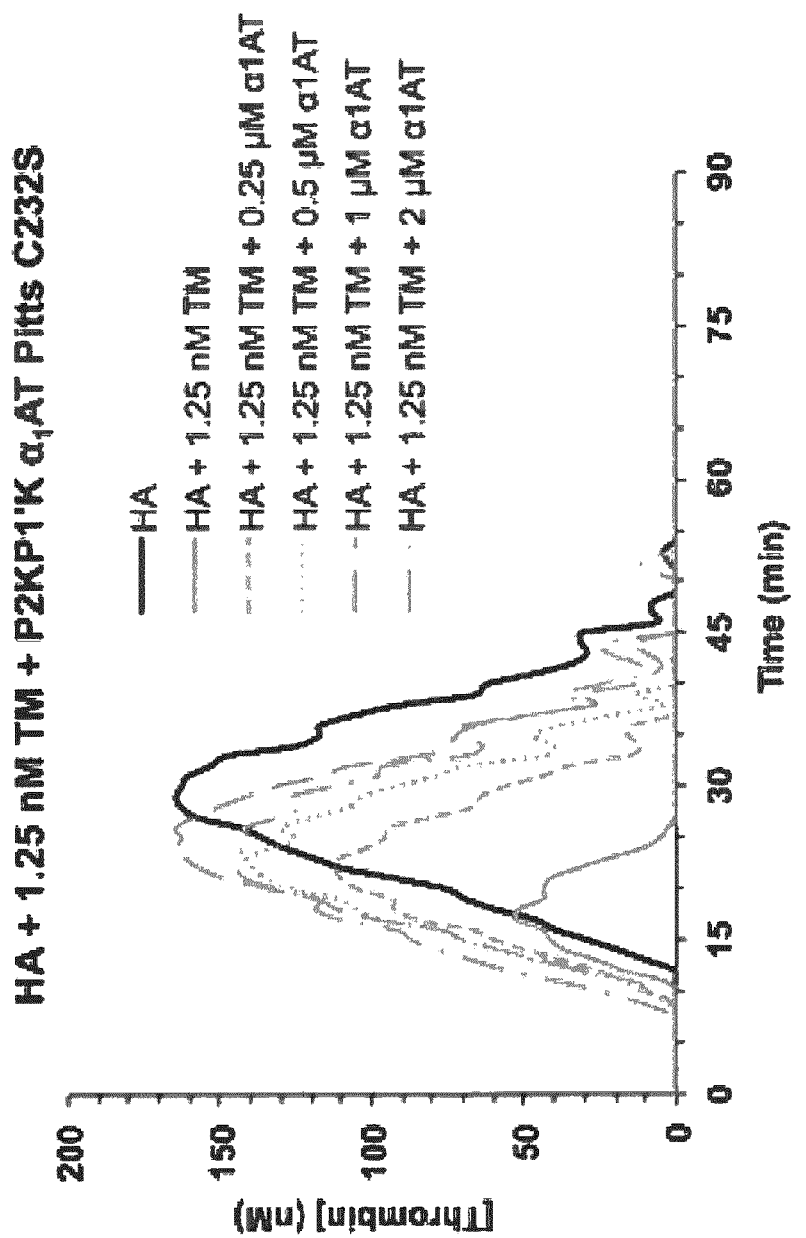
Figure 9C:
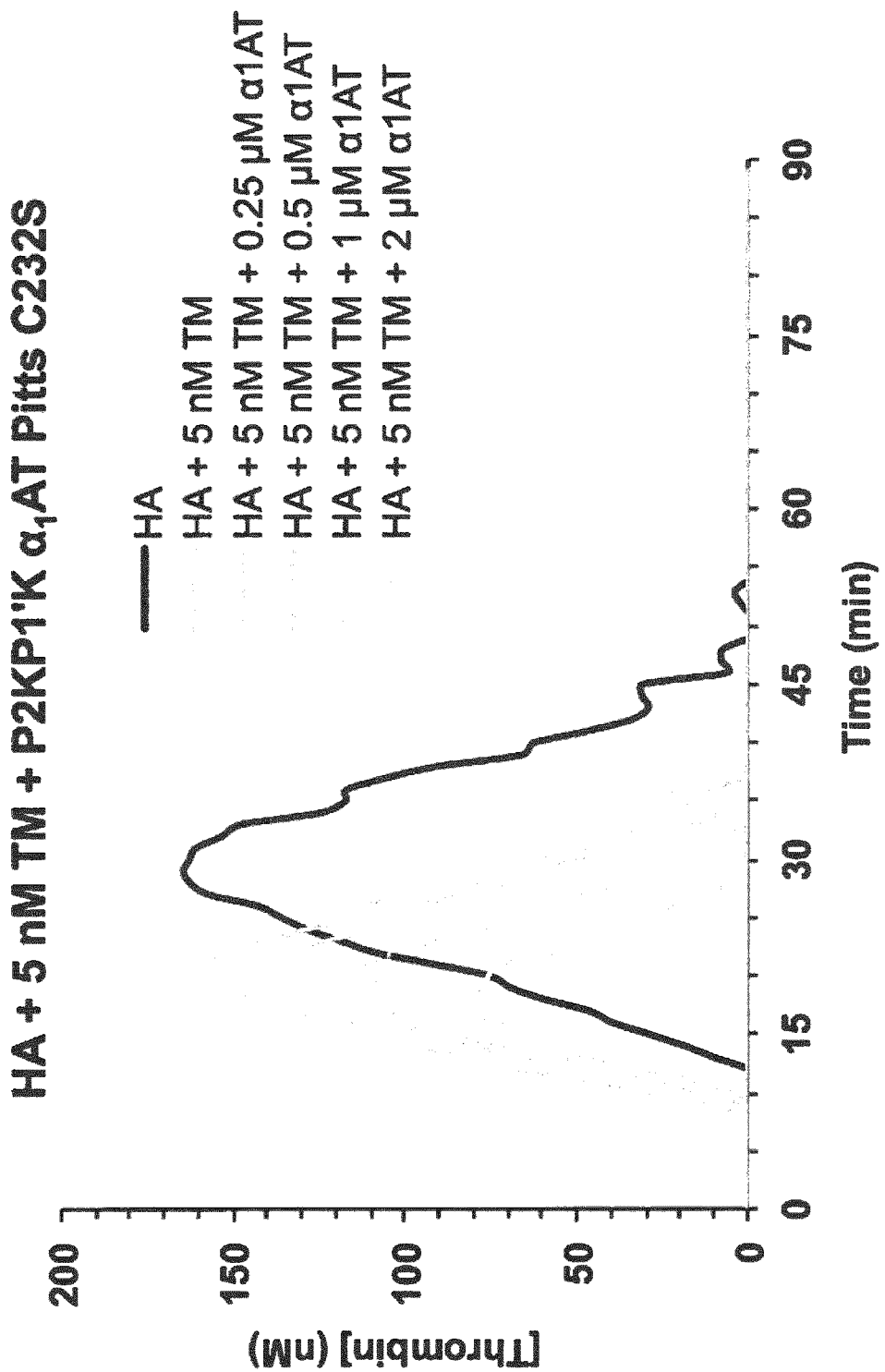
Figure 9D:
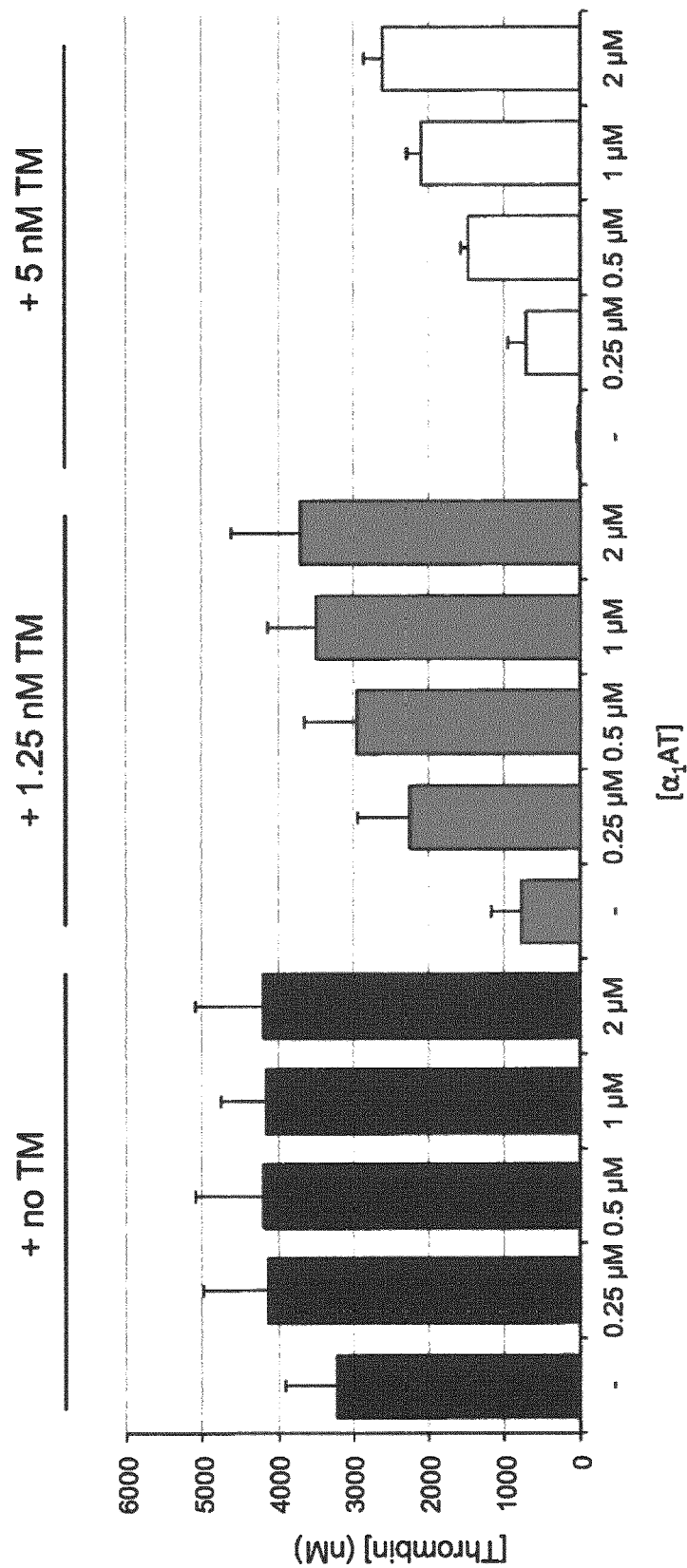
Figure 10A:
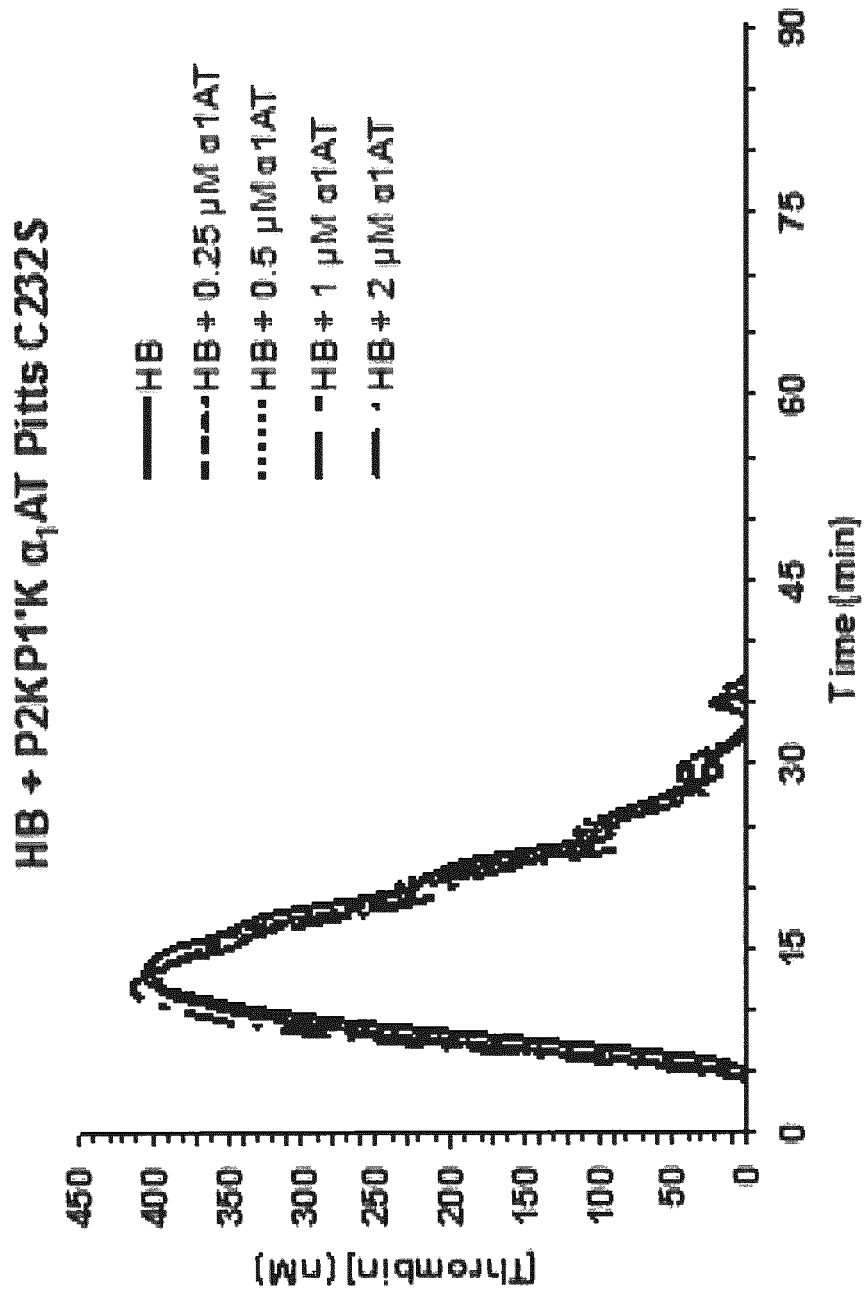
Figure 10B:
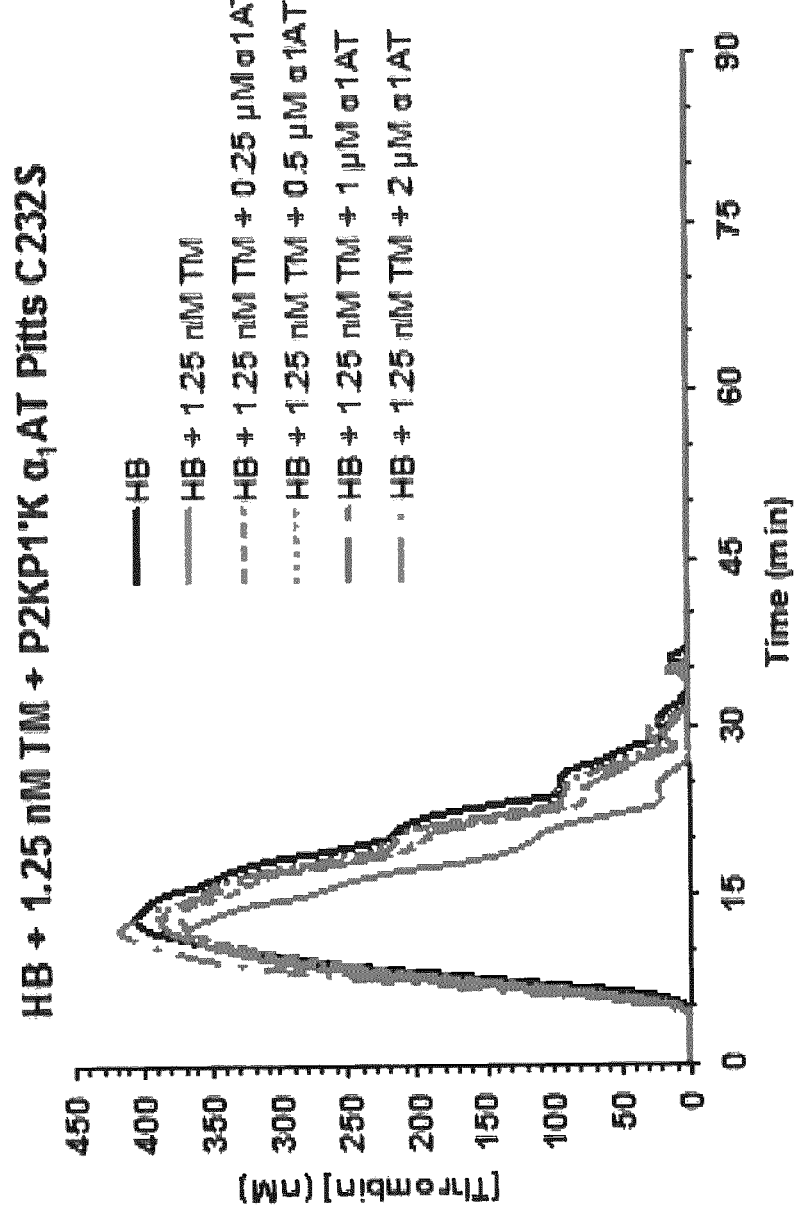
Figure 10C:
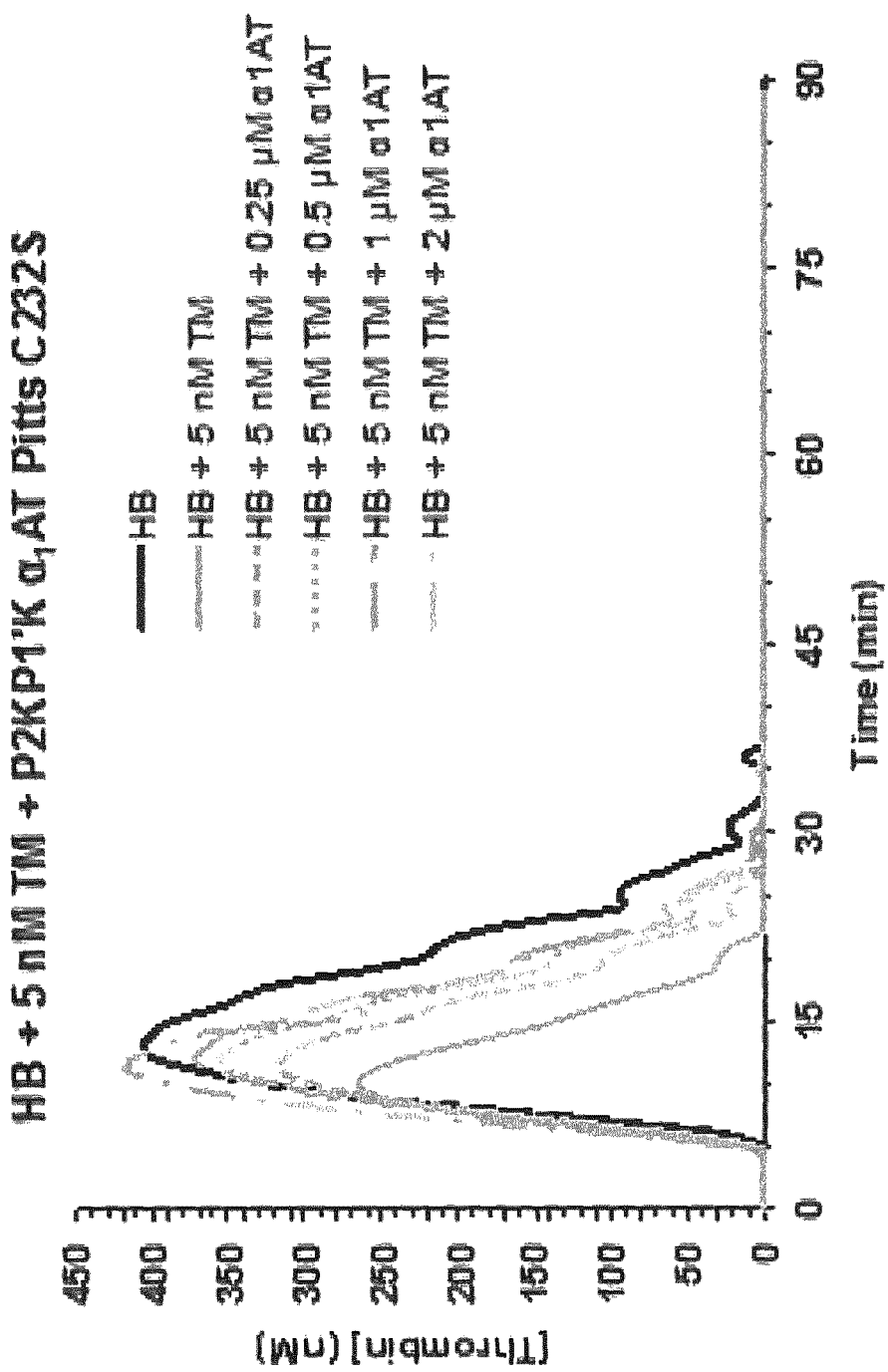
Figure 10D:
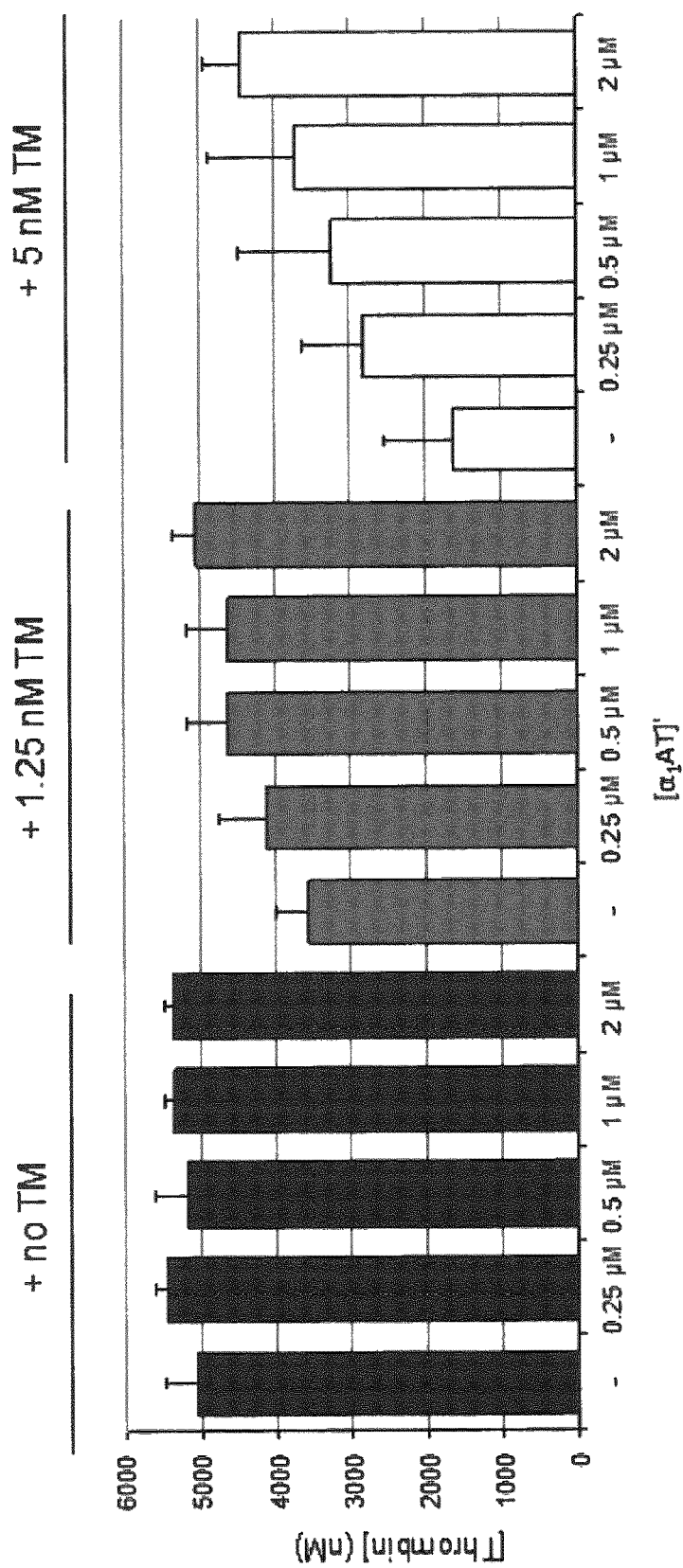

The effects of both FL $\alpha_1$AT Pitts C232S and FL $\alpha_1$AT Pitts C232S P2KP1'K on HA and HB plasma were comparable to the results from pooled NP. FL $\alpha_1$AT Pitts inhibited thrombin generation in the presence and absence of TM in both HA (fVIII-deficient) and HB plasma (fIX-deficient) (FIG. 8). FL $\alpha_1$AT Pitts C232S P2KP1'K could rescue the effect of TM on thrombin generation in both fVIII- and fIX-deficient plasma and had no effect in the absence of TM (FIGS. 9 and 10). This indicates that FL $\alpha_1$AT Pitts C232S P2KP1'K can inhibit APC and have a procoagulant effect in factor-deficient plasma. This means it could potentially promote clot formation and reduce bleeding in hemophilia patients. The magnitude of this procoagulant effect will be determined by the relative contribution of the protein C system to the reduction in thrombin generation in vivo. The in vitro experiments shown here cannot be used to predict the likely efficacy of this mutant in vivo, however they do show that in complex plasma systems FL $\alpha_1$AT Pitts C232S P2KP1'K can inhibit APC and does not interfere with the procoagulant pathways, and that these effects are independent of the presence or absence of fIX and fVIII.

In order to verify our in vitro data we wanted to use in vivo mouse models of hemophilia. However, to verify that the effect of human $\alpha_1$AT on mouse plasma would be comparable to the effect seen in human plasma we first performed a TGA in mouse plasma. This was done using a modified TGA protocol (Bunce et al, 2011; Ivanciu et al, 2011). These modifications were necessary because of the increased concentrations of inhibitory proteins in mouse plasma that preclude TGA assays under standard conditions (Tchaikovski et al, 2007; Bunce et al, 2011; Ivanciu et al, 2011). Comparable to the human system, there was no thrombin generation in HB mouse plasma under the baseline conditions of the assay. Therefore, we performed a titration spiking in different concentrations of Innovin. A concentration of 1:12,000 Innovin was chosen for subsequent assays.

Because no murine TM was available, we used soluble human TM as used in the human plasma TGAs to promote APC formation in the mouse TGA assay. The concentration required to see any effect of human TM in HB mouse plasma was ~100-fold higher than seen in human plasma. This could be explained by the observation that human TM knock-in mice show reduced ability to activate murine PC (Raife et al, 2011). This indicated that human TM is less potent at promoting murine PC activation than murine TM. A concentration of 750 nM human TM was used in subsequent experiments.

Different concentrations of both FL $\alpha_1$AT Pitts C232S and FL $\alpha_1$AT Pitts C232S P2KP1'K were then added to the determined conditions in mouse HB plasma both in the absence and presence of TM to compare the effect of these mutants in mouse plasma to the previous TGA results in human plasma.

Figure 11A:
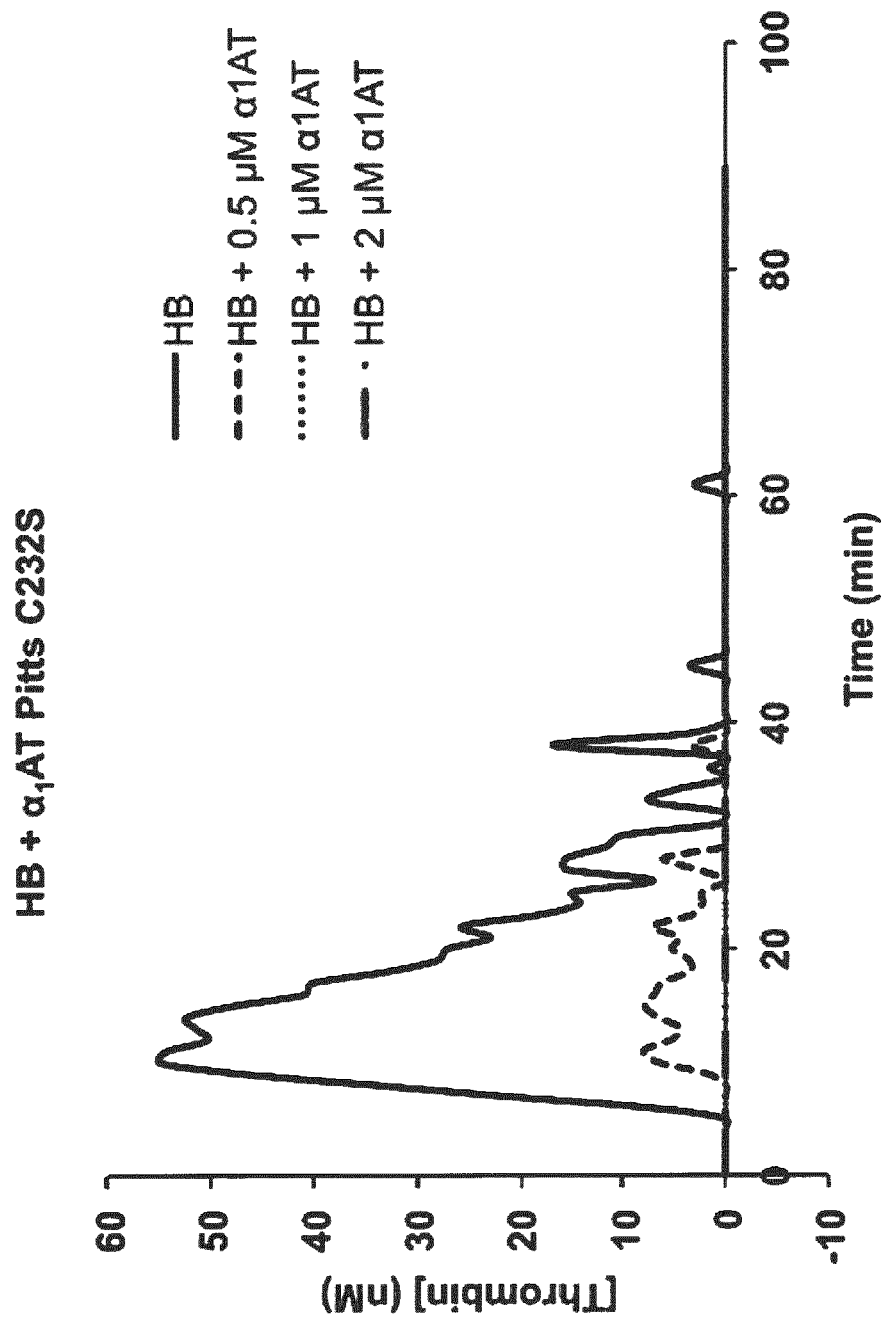
Figure 11B:
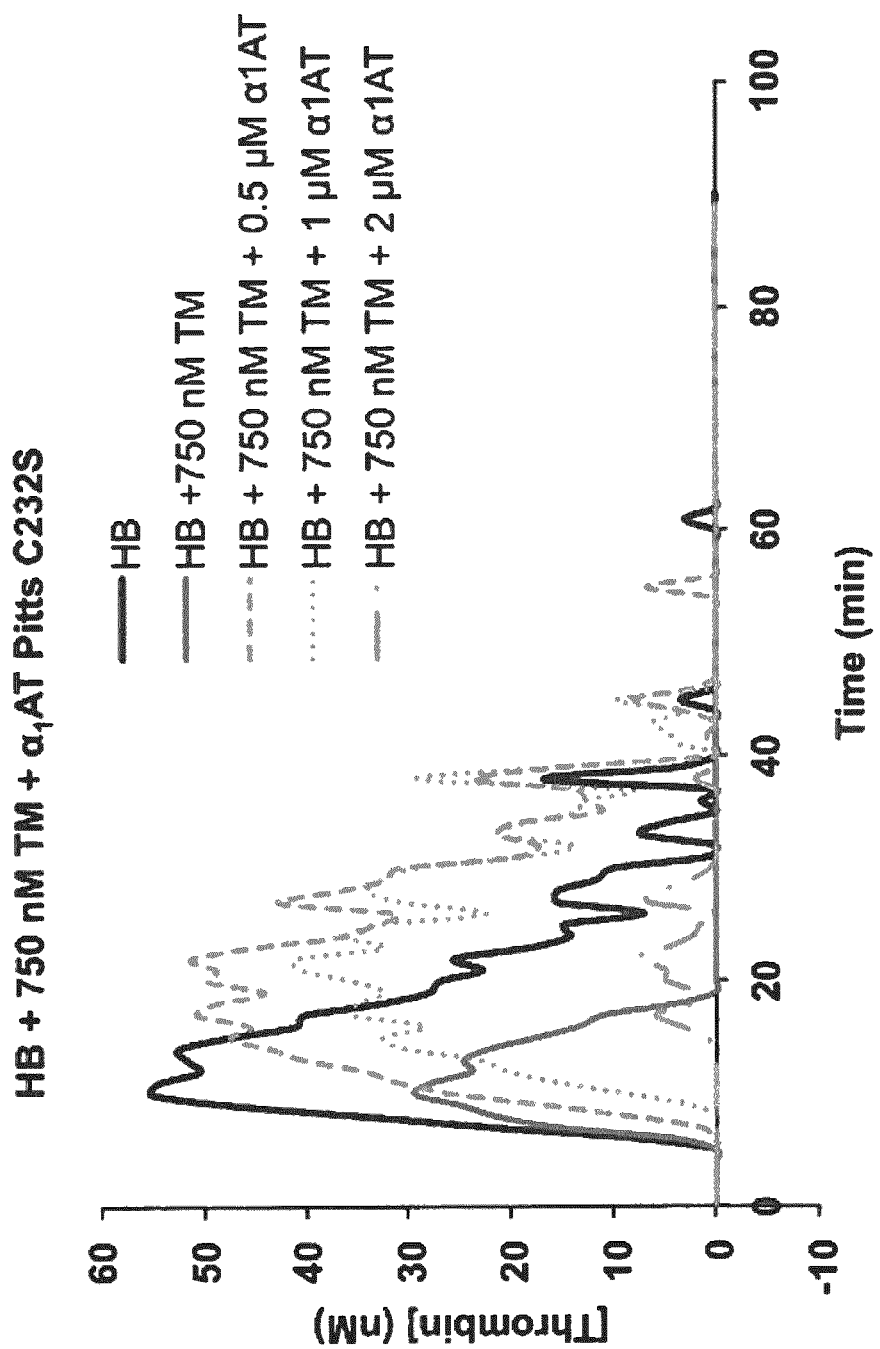
Figure 11C:
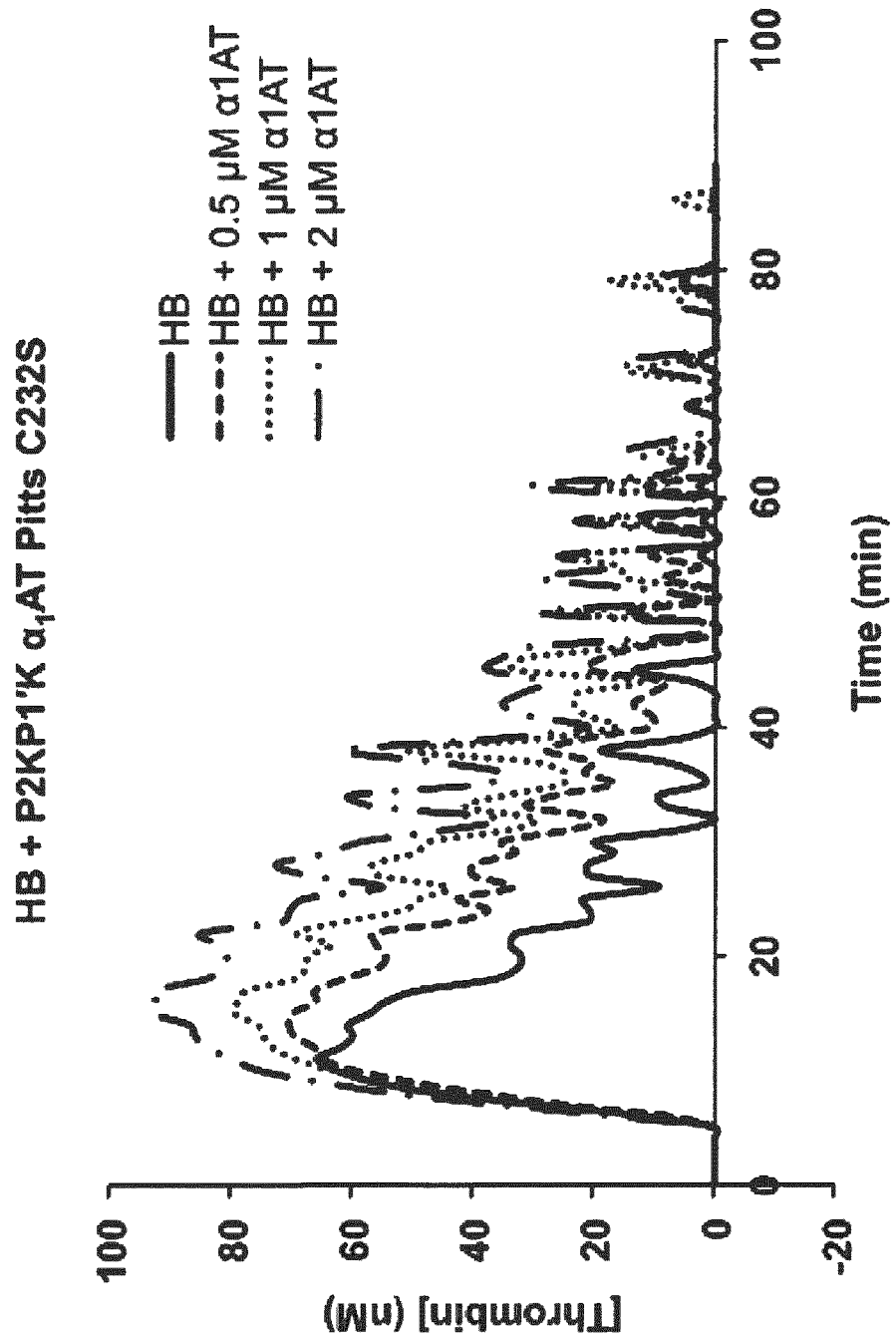
Figure 11D:
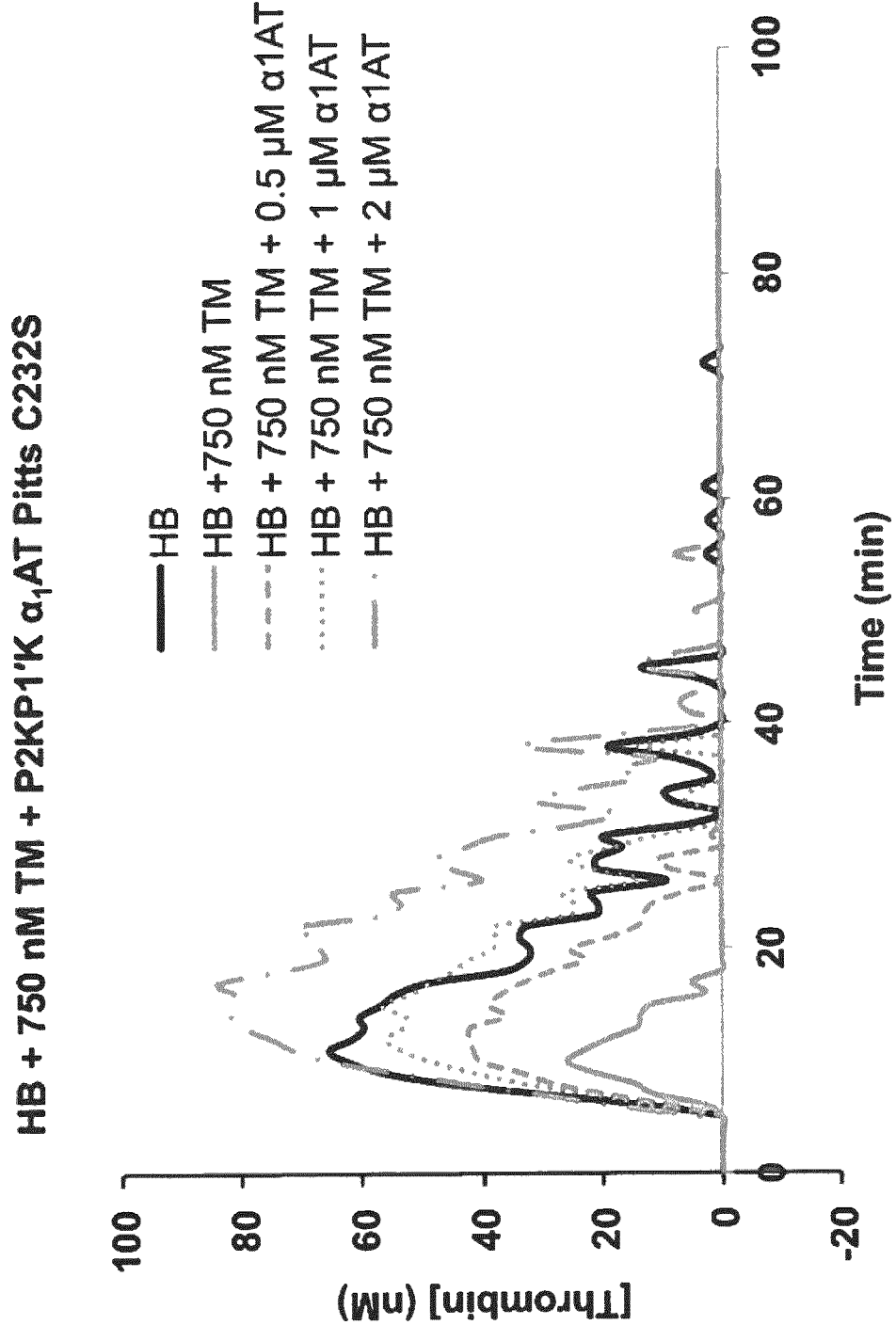
Figure 11E:
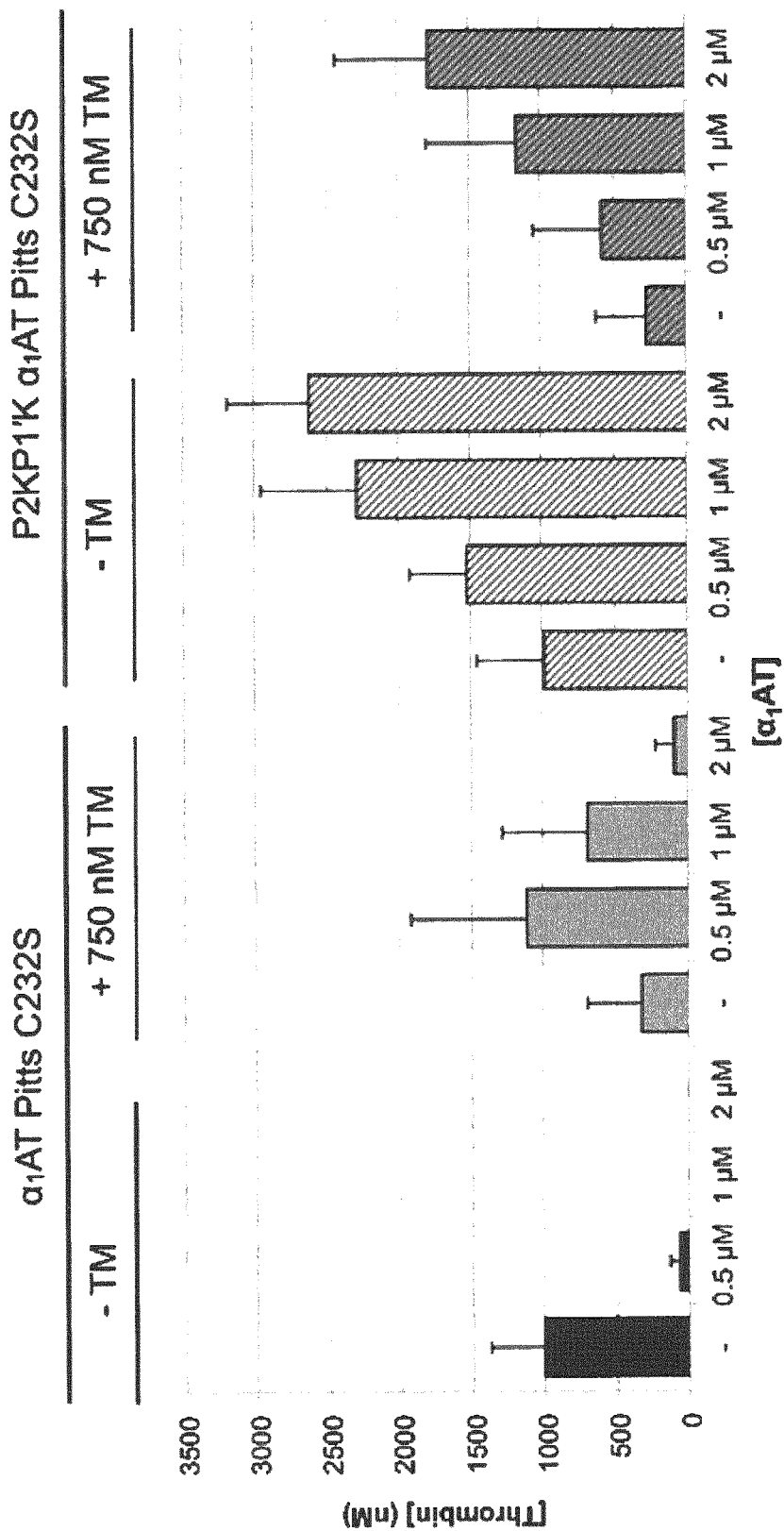

FL $\alpha_1$AT Pitts C232S reduced thrombin generation in mouse HB plasma in the absence of TM as seen in human plasma (FIG. 11A). However in the presence of TM, at the lowest $\alpha_1$AT concentration, there was a partial rescue of thrombin generation (FIG. 11B). This may potentially be due to a difference in the relative rates of inhibition for murine thrombin and murine APC by FL $\alpha_1$AT Pitts compared to the rates seen in humans, such that the generated APC is inhibited prior to thrombin inhibition. When the concentration of FL $\alpha_1$AT Pitts C232S is increased to such levels that all APC has been inhibited, thrombin is also inhibited. This could explain the results seen in FIG. 11B, but was not further investigated. FL $\alpha_1$AT Pitts C232S P2KP1'K rescued thrombin generation knocked-down by TM addition in HB mouse plasma as it did in human plasma (FIG. 11D). However, when FL $\alpha_1$AT Pitts C232S P2KP1'K was added to HB mouse plasma in the absence of TM, an increase in thrombin generation was also observed (FIG. 11C). It is possible that this effect relates to the method of blood collection employed for these experiments. To collect plasma, the tail was transected and blood collected into citrate. This was then spun down and the plasma removed and frozen. The injury inflicted for blood collection leads to activation of the coagulation system and may cause generation of APC in the plasma prior to the experiment. Additionally, mice do not have PCI in their plasma (Zechmeister-Machhart et al, 1996), which may increase the circulating half-life of APC, such that it is not inactivated prior to the TGA assay. An alternative explanation, which cannot be ruled out at present would be an off-target procoagulant effect in mouse plasma. However, since this effect is not seen in human plasma, this would involve the inhibition of a mouse-specific anticoagulant protease.

To investigate a potential in vivo effect of FL $\alpha_1$AT Pitts C232S P2KP1'K and to determine if it could potentially be useful as either a prophylactic agent or a treatment for hemophilia we used two in vivo mouse assays; tail clip and a cremaster arteriole laser injury model. The mice used were male, fIX knockout mice on the BALB/c background (Lin et al, 1997; Ivanciu et al, 2011).

Figure 12:
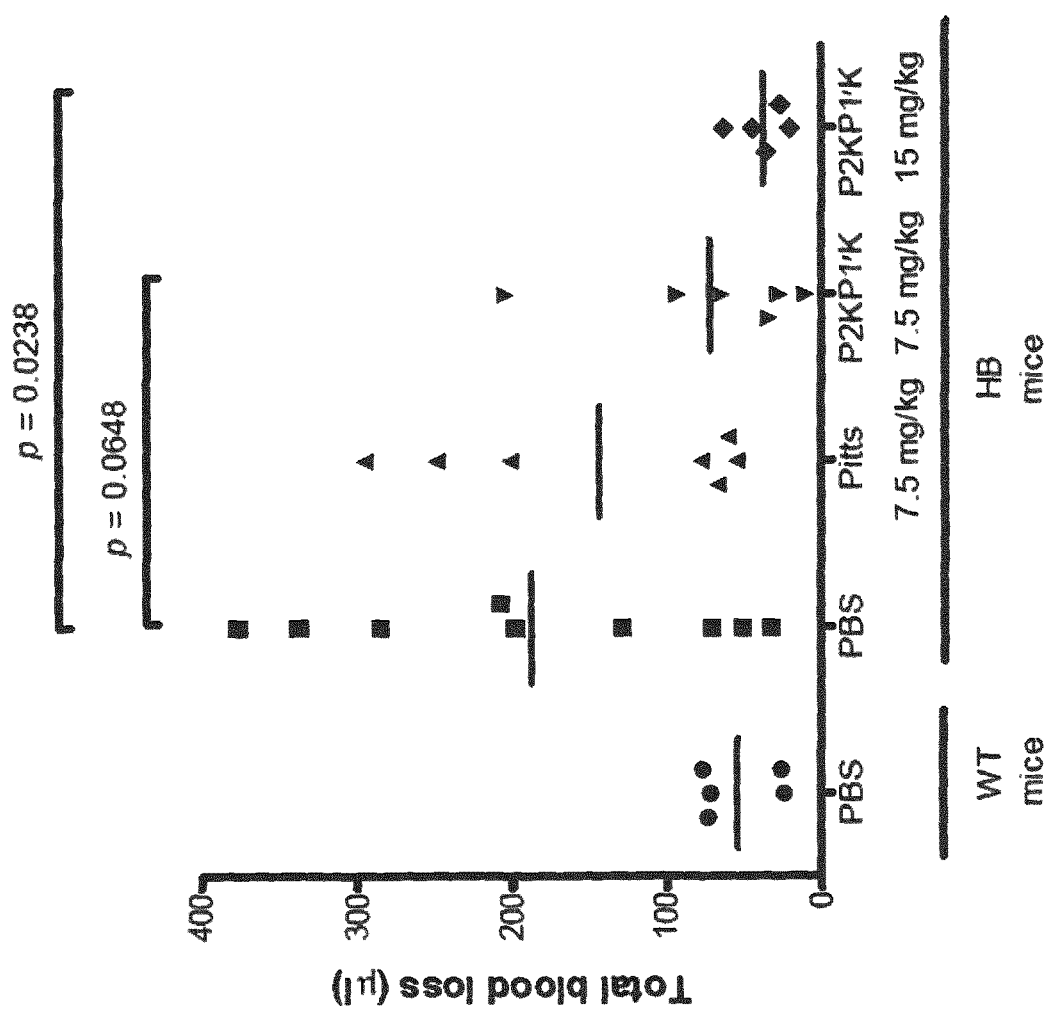

In the tail clip assay, protein or buffer was injected through the tail vein and after a 5 min incubation period, the tail was transected at a diameter of 3 mm and placed in 14 ml 37° C. saline solution in a 37° C. water bath. Blood was collected for 10 min and the resulting blood loss was quantified by measuring total hemoglobin after red cell lysis by measuring absorbance at 575 nm (Ivanciu et al, 2011). The volume blood loss was calculated by making a standard curve where known volumes of blood collected by tail transection were processed in a similar manner to the tail clip samples. After red cell lysis, the absorbance at 575 nm was determined and plotted against the volume blood loss to generate the standard curve. Tail clip assays showed a potent procoagulant effect of FL $\alpha_1$AT Pitts C232S P2KP1'K (FIG. 12). At the dose of 15 mg/kg, blood loss of the HB mice was restored to the level of WT mice injected with PBS (FIG. 12). Lower dose FL $\alpha_1$AT Pitts C232S P2KP1'K also showed a trend to reduction of bleeding with respect to HB mice although this was not statistically significant. FL $\alpha_1$AT Pitts C232S showed no significant effect on blood loss at 7.5 mg/kg.

Another in vivo model used for evaluating procoagulant agents is the intravital cremaster arteriole laser-induced injury model (Falati et al, 2002). In this system, a cannula is inserted into the mouse jugular vein to allow infusion of the therapeutic protein as well as fluorescently-tagged antibodies to fibrin and platelets. The cremaster muscle is then spread out for imaging. Clot formation after laser-induced injury to the arterioles is imaged and quantified using fluorescence microscopy.

Figure 13:
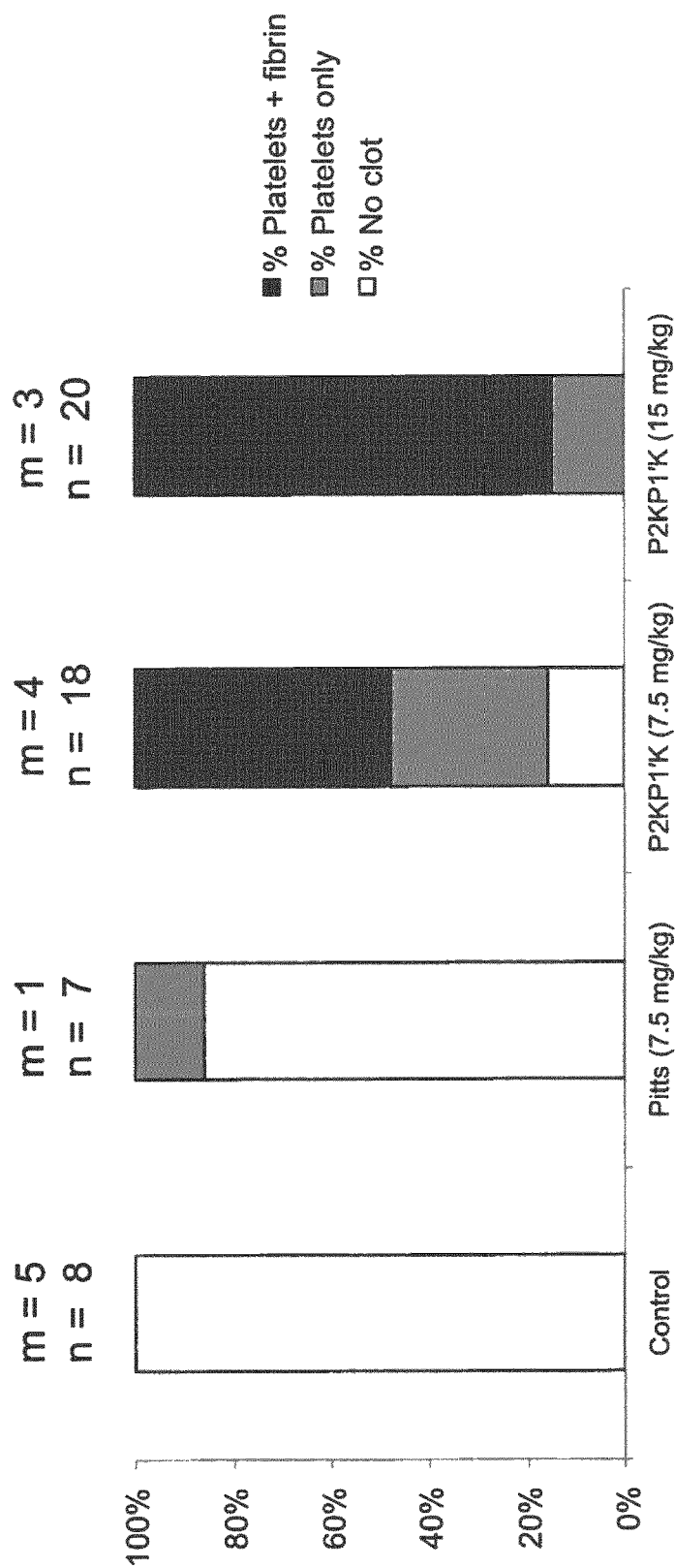
Figure 14:
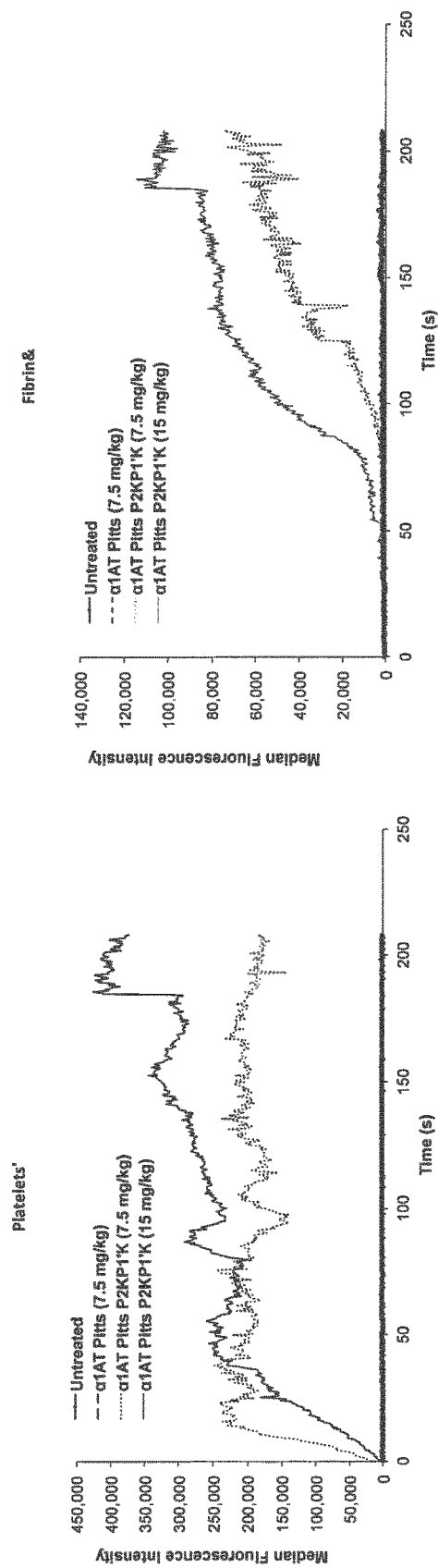
Figure 15:
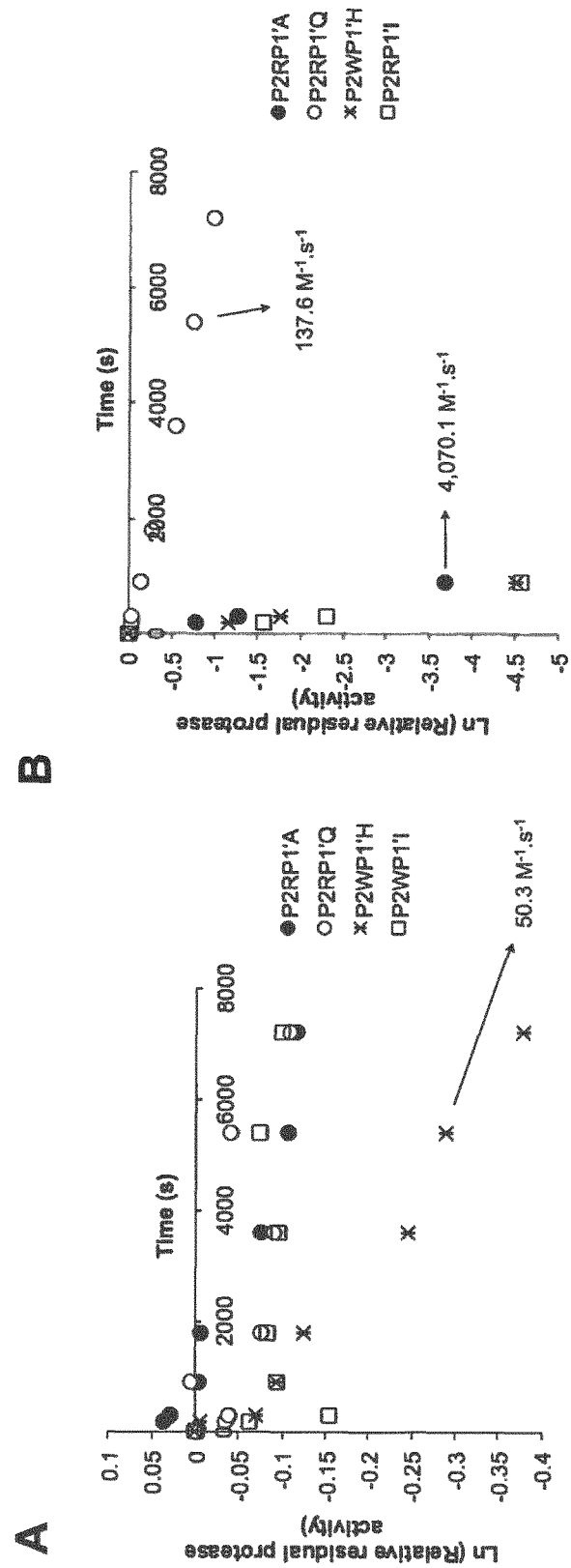

For an overall qualitative assessment, injuries were sorted into three categories: no clot (no fluorescence detected), platelet clot (only platelets visible, these clots were generally unstable and dissolved over the course of the imaging) and platelets+fibrin (both platelet and fibrin fluorescence visible and clot remained stable over the course of the imaging). This showed that there was a dose-dependent increase in stable platelet and fibrin clot formation with increasing concentration of FL $\alpha_1$AT Pitts C232S P2KP1'K (FIG. 13). All images were quantified for platelet and fibrin fluorescence. The median value for each timepoint was calculated and the results plotted in FIG. 14. These data included the quantification from all images, regardless of their category assigned for FIG. 13. The plots of the median show that control or FL $\alpha_1$AT Pitts C232S infused mice exhibit no clot formation, whereas both high and low dose FL $\alpha_1$AT Pitts C232S P2KP1'K showed platelet aggregation and fibrin deposition at the site of the injury. No difference could be detected between the two doses in terms of platelet aggregation. For fibrin, there was a dose-dependent increase in fibrin deposition for FL $\alpha_1$AT Pitts C232S P2KP1'K and no fibrin for either control or FL $\alpha_1$AT Pitts C232S infused mice (FIG. 14).

Taken together, these results show that FL $\alpha_1$AT Pitts C232S P2KP1'K has a procoagulant effect in both in vitro assays and in vivo models of hemophilia. The in vivo experiments were all done in mouse models of hemophilia B, however TGA results in human plasma (FIGS. 9 and 10) and the proposed mechanism of action of FL $\alpha_1$AT Pitts C232S P2KP1'K indicate that its procoagulant effect should be independent of fIX or fVIII deficiency and could therefore be used in both hemophilia A and B. The procoagulant effect seen in vivo was sufficient to reduce bleeding to the same levels as seen for WT mice (FIG. 12) indicating that serpins that inhibit APC can be used for treatment of bleeding disorders and not only as a prophylactic or an adjuvant to existing treatments.

A targeted random mutagenesis strategy was also employed on the $\alpha_1$AT scaffold in order to explore potential additional APC specific mutants on the $\alpha_1$AT scaffold.

Three different α₁AT variant libraries were generated on the FL α₁AT Pitts C232S background: one randomised at P2, one randomised at P1' and a third library randomised at both P2 and P1'. The resulting plasmid libraries were transformed into the Rosetta2(DE3)pLysS expression strain and protein expressed in 96-well plates. Bacteria were lysed and the lysates assayed for thrombin and APC inhibition.

For the single variant libraries, 88 colonies were assayed per library. For the double (P2P1') variant library, 460 colonies were assayed. FL $\alpha_1$AT Pitts and FL $\alpha_1$AT Pitts P2KP1'K (the lead APC specific variants) were expressed on all assay plates as a reference. Variants with higher or equal APC inhibitory activity (lower or equal residual APC activity) and lower or equal thrombin inhibitory activity (higher or equal residual thrombin activity) compared to P2KP1'K $\alpha_1$AT were deemed candidates for variants specific for APC over thrombin. A subset of candidate variants was picked and re-assayed in the same setup to verify the results from the first screen. Mutants showing similar properties in both assays were then sequenced. The resulting sequences are shown in Table 9. To verify the ability of this assay to pick out variants, which were specific for APC over thrombin, nine variants identified in Table 9 were expressed on a larger scale in *E. coli* and purified. The second-order rate constant of inhibition with respect to thrombin and APC was then determined for each mutant. The results are shown in Table 10. These results confirmed that all variants tested had a higher specificity for APC than for thrombin unlike the FL $\alpha_1$AT Pitts C232S variant.

Certain types of residues were favored in the $\alpha_1$AT Pitts scaffold at both P2 and P1' positions (Table 9). Specificity was primarily conferred by the presence of bulky polar (Q, N, Y) bulky hydrophobic (W) or positively charged residues (R, H, K) at P2 and P1'. Other residues seen at these positions included C, A, T, S and V. These medium to small residues were accompanied in the double variant library by a complementing large positively charged residue (R, K) or large polar residue (Y, N, Q) at the other position, which likely has a larger influence on the specificity swap. However, there may be a cooperative effect of these mutations as well, especially where the P1' is R. P1'R showed variable results in the single variant library screen and may have some residual thrombin inhibitory activity. The P2 P is known to be important for thrombin cleavage of substrates (Gallwitz et al, 2012). Simple removal of this residue coupled to a specificity swapping mutation at P1' may be sufficient to generate an APC specific inhibitor with little residual thrombin inhibitory activity. Especially T at P2 might have some effect on its own as, out of its partnering residues at P1' (Q, N, Y, R), only R was identified in the single residue P1' variant library as being sufficient to cause a specificity swap by itself.

Interestingly, non-specific mutants that clustered around the $\alpha_1$AT Pitts control were shown to be largely $\alpha_1$AT Pitts. All retained the P2 P, showing its importance in maintaining thrombin inhibitory activity. The P1' was more variable, consistent with the distribution of mutants in the P1' variant library. Comparing the spread of variants in the P2 and P1' libraries, thrombin seemed to be more tolerant to P1' than to P2 mutations. However, the appearance of favorable residues in the double variant libraries that were not present in the single variant libraries indicate that the effects of these residues on specificity may be cooperative and double mutations may be more effective than single mutations at increasing specificity.

The random mutagenesis results presented above showed that it was possible to generate mutants that showed specificity for APC over thrombin other than the lysine mutants already identified. So far, the random mutagenesis strategy was used, assuming that once specificity over thrombin was obtained, these mutants would also show some degree of specificity for APC over other procoagulant proteases. To test this, the PT and aPTTs of the random mutants in Table 10 were tested. These results are displayed in Table 11. None of the mutants had a significant effect on the PT, unlike previously shown for FL α1AT Pitts C232S (FIG. 4). This provides indication, that the mutants have largely lost their inhibitory activity towards procoagulant proteases. However, aPTTs are more sensitive to the presence of inhibitors. Therefore, the measure of the aPTT might give a more accurate representation of smaller residual inhibition. Previous experiments (FIG. 5) showed that FL α1AT Pitts C232S rendered plasma unclottable in the aPTT assay. In contrast, only one of the mutants evaluated here showed this effect (P2TP1'N). Some mutants, such as P2KP1'H and P2KP1'N showed only a relatively small prolongation of the aPTT and were therefore potentially interesting.

From these results, we selected four mutants, P2R, P2QP1'K, P2KP1'H and P2KP1'N (all on the Pitts, P1R background). These showed either a high inhibition of APC over thrombin (Table 10) and for some also a low prolongation of the aPTT (P2KP1'H and P2KP1'N). Because they did not prolong the PT, it is unlikely that they inhibit TF:fVIIa. The most likely candidates for prolongation of the aPTT would be inhibition of fXIa or fXa. Of these, fXa inhibition would most inhibit the initial stages of coagulation and was therefore considered to be a more significant barrier for a successful inhibitor. Inhibition constants for the inhibition of fXa by these four mutants were therefore determined as described above (Table 12). P2R showed significant inhibition of fXa, which may be the reason for its prolongation of the aPTT. The other three mutants showed lower fXa inhibition, but none of the mutants were as specific as the previously identified P2KP1'K mutant. Nevertheless, P2KP1'N, P2QP1'K and P2KP1'H represent additional promising candidates for further development as they show specificity for APC over thrombin and fXa. In addition, their inhibition of APC is roughly 2-fold increased with respect to the P2KP1'K mutant described earlier. This faster inhibition might in part compensate for the slightly reduced specificity.

However, these results indicated that selecting for specificity for APC over thrombin is not completely sufficient to design an inhibitor which also shows specificity over fXa and other procoagulant proteases. Therefore, the random mutagenesis strategy was extended further. Mutants, which previously had been selected for specificity for APC over thrombin, were rescreened against fXa and mutants selected, which had reduced fXa inhibition, while maintaining low thrombin inhibition and APC inhibition.

Four additional mutants were identified from this additional screen. These all had the P1R mutation and in addition had either P2RP1'A, P2RP1'Q, P2WP1'I or P2WP1'H. To verify the specificity of these mutants, an initial experiment was performed, using only one concentration of serpin and testing its inhibition of thrombin and fXa. APC inhibition was not considered at this stage, because mutants were selected based on their low inhibition of thrombin and fXa. Serpin and protease were incubated for different times and at the indicated timepoints, the reaction was stopped by addition of an excess of chromogenic substrate. Residual protease activity was divided by the initial protease activity and the natural log of this value plotted against time (FIG. 15). The slope of this line divided by the serpin concentration gives an estimate of the second-order rate constant of inhibition. These assays showed that while all mutants hardly inhibited thrombin, with the fastest inhibitor, P2WP1'H having a second-order rate constant of ~50.3 $M^{-1} \cdot s^{-1}$ (compare to the inhibition constant of FL $\alpha_1$AT Pitts C232S, 2.928×10$^5$ $M^{-1} \cdot s^{-1}$). However, P2RP1'A, P2WP1'I and P2WP1'H showed significant inhibition of fXa. The second-order rate constant was only ~10-fold reduced for these mutants compared to FL $\alpha_1$AT Pitts C232S (4,070.1 $M^{-1} \cdot s^{-1}$ for P2RP1'A compared to 4.13×10$^4$ $M^{-1} \cdot s^{-1}$ for FL $\alpha_1$AT Pitts C232S). P2RP1'A, P2WP1'I and P2WP1'H showed similar fXa inhibition to each other.

Only one mutant showed significant selectivity against both thrombin and fXa. This mutant had a P2RP1'Q in addition to the Pitts (P1R) mutation. Because of its selectivity, it was interesting for more thorough investigation. Previous results from both the random and rational mutagenesis studies indicated that R and K residues perform reasonably similarly. We therefore also generated a P2KP1'Q mutant on the P1R background as it was expected from the results shown here to have similar properties. The results from measurements of inhibition constants and aPTTs (experiments performed as described before) for both mutants are shown in Table 13. The P2KP1'K mutant is shown for comparison. Both P2KP1'Q and P2RP1'Q showed very low inhibition of thrombin and fXa. In addition, there was also hardly any effect on the aPTT. APC inhibition was significant, being only slightly reduced in comparison to P2KP1'K. Therefore, these two mutants would be expected to perform similarly to P2KP1'K and may represent other potentially promising alternative molecules for further development.

We evaluated inhibition of murine thrombin and APC by FL $\alpha_1$AT Pitts C232S P2KP1'K. Thrombin and APC were obtained from recombinant sources. The proteases used are truncated with respect to the plasma version, including only the EGF2-protease domains for APC (Gla-domainless APC) and the protease domain for thrombin. Therefore, we also tested the human versions of these proteases to ensure that any differences were due to a species difference, rather than a construct difference. Human and murine thrombin showed none or very little reactivity with FL $\alpha_1$AT Pitts C232S P2KP1'K by SDS-PAGE, indicating that in this respect, results from model systems would be relevant to the human system. Second-order rate constants of inhibition were (8.14±0.58)×10$^3$ $M^{-1} \cdot s^{-1}$, for human Gla-domainless APC, (3.80±0.37)×10$^3$ $M^{-1} \cdot s^{-1}$ for murine Gla-domainless APC, compared to (14.88±1.87)×10$^3$ $M^{-1} \cdot s^{-1}$ for human plasma APC. These results provided indication that while the reactivity of the mutant in mouse models would likely be lower than in humans, i.e. the relative dose for the same effect might need to be higher, the effect in terms of protease inhibition is likely to be similar.

The data presented show as a proof-of-principle that the serpin scaffold can be used to generate specific APC inhibitors, using only very few mutations, that these inhibitors can have procoagulant activities both in vitro and in vivo and as such show promise as procoagulant agents for treatment and prophylaxis of bleeding disorders such as hemophilia.

REFERENCES

Berntorp E (2009) *Haemophilia* 15: 3-10
Bertina R M, et al (1994) *Nature* 369: 64-67
Bohn R L et al (2004) *Haemophilia* 10: 63-68
Bolton-Maggs P H B & Pasi K J (2003) *Lancet* 361: 1801-1809
Brettler D B (1996) *Baillieres Clin. Haematol.* 9: 319-329
Brummel-Ziedins K E et al (2011) *J. Thromb. Haemost.* 9: 2262-2267
Bunce M W et al (2011). *Blood* 117: 290-298
Butenas S et al (2006) *J. Thromb. Haemost.* 4: 2411-2416
Carrell R et al (1985) *Trends in Biochemical Sciences* 10: 20-24
Chuansumrit A et al (2000) *Haemophilia* 6: 61-65
De Nanteuil G et al (2006) *J. Med. Chem.* 49: 5047-5050
Di Minno M N D et al (2010) *Haemophilia* 16: e190-201
DiMichele D (2007) *J. Haematol.* 138: 305-315
Duckers C et al (2010) *Blood* 115: 879-886
Elisen M G L M et al (1998) *Blood* 91: 1542-1547
Escobar M A (2010) *Haemophilia* 16 Suppl 3: 29-34
Escobar M & Sallah S et al (2013) *J. Thromb. Haemost.* 11, 1449-1453.
Falati S et al (2002) *Nat. Med.* 8: 1175-1181
Fortenberry Y M et al (2011) *J. Thromb. Haemost.* 9: 861-863
Franchini M & Lippi G (2010) *Thrombosis Research* 125: 119-123
Fukudome K et al (1996) *J. Biol. Chem.* 271: 17491-17498
Gallwitz et al (2012) *PLoS ONE* 7(2): e31756
Gettins P G W (2002) *Chem. Rev.* 102: 4751-4803
Gringeri A et al (2003) *Blood* 102: 2358-2363
Haya S et al (2007) *Haemophilia* 13 Suppl 5: 52-60
Heeb M J & Griffin J H (1988) *J. Biol. Chem.* 263: 11613-11616
Heeb M J et al (1990) *J. Biol. Chem.* 265: 2365-2369
Hopkins et al (1993) Biochemistry 32; 7650-7657
Hua B et al (2009) *Haematologica* 94: 881-884
Huntington J A et al (2000) *Nature* 407: 923-926
Irving et al (2000) *Genome Res.* 10; 1845-1864
Ivanciu L et al (2011) *Nat. Biotechnol.* 29: 1028-1033
Kalsheker N (1989) *Biosci. Rep.* 9: 129-138
Laurell C B et al (1977) *Clin Sci Mol Med* 52: 457-461
Laurell M et al (1990) *Blood* 76: 2290-2295
Lee M et al (2006) *Haemophilia* 12 Suppl 3: 1-7
Li W & Huntington J A (2008) *J. Biol. Chem.* 283: 36039-36045
Li W et al (2008) *Proc. Natl. Acad. Sci. U.S.A.* 105: 4661-4666
Lin H F et al 1997) *Blood* 90: 3962-3966
Lowe, G. D. & Ludlam, C. A. (2008) *J. Thromb. Haemost.* 6, 1982-1983.
Lu D et al (1996) *Blood* 87: 4708-4717
Mannucci P M (2003) *J. Thromb. Haemost.* 1: 1349-1355
Mannucci P M (2008) *Haemophilia* 14 Suppl 3: 10-18
Mather T et al (1996) *EMBO J* 15: 6822-6831
Meijers J C et al 1988) *Biochemistry* 27: 4231-4237
Mosnier L O et al (2001) *Thromb. Haemost.* 86: 1057-1064
Nagel K. et al (2011) *Haemophilia,* 17, 872-874.
Negrier C et al (2006) *Haemophilia* 12 Suppl 6: 48-52—discussion 52-3
Owen M C et al (1983) *N. Engl. J. Med.* 309: 694-698
Pratt C W & Church F C (1992) *J. Biol. Chem.* 267: 8789-8794
Pratt C W et al (1992) *J. Biol. Chem.* 267: 8795-8801
Raife T J et al (2011) *Arterioscler. Thromb. Vasc. Biol.* 31: 2509-2517
Schechter I et al (1967) *Biochem Biophys Res Comm* 27: 157-162
Stearns-Kurosawa D J et al (1996) *PNAS. U.S.A.* 93: 10212-10216
Suzuki K et al (1983) *J. Biol. Chem.* 258: 163-168
Suzuki K et al (1984) *Journal of Biochemistry* 95: 187-195
Tagariello, G et al (2009) *Blood,* 114, 779-784.

Tchaikovski S N et al (2007) *J. Thromb. Haemost.* 5: 2079-2086
Teitel J M (1999) *Haemophilia* 5 Suppl 3: 43-49
Teitel, J M & Sholzberg, M (2013) *Blood Reviews* 27 103-109
Turecek P L, et al (2004) *Haemophilia* 10 Suppl 2: 3-9
Ullman M et al (2006) *Haemophilia* 12 Suppl 6: 74-9; discussion 79-80
World Federation of Hemophilia (2011) 2010 WFH Global Survey Report
Yamasaki M et al (2011) *EMBO Rep.* 12: 1011-1017
Zechmeister-Machhart M et al (1996) *Immunopharmacology* 32: 96-98

TABLE 1

| Variant | Second-order rate constants of inhibition (mM$^{-1}$·s$^{-1}$) | | Fold inhibition |
|---|---|---|---|
| | Thrombin | APC | APC/thrombin |
| A22 WT PCI | 28.21 ± 1.51 | 0.68 ± 0.032 | 0.02 |
| A22 P1'K PCI | 0.022 ± 0.0024 | 0.88 ± 0.074 | 40 |
| A22 P2KP1'K PCI | ~0.03* | 0.28 ± 0.013 | 9.3 |
| FL α$_1$AT Pitts C232S | 292.76 ± 17.60 | 108.16 ± 7.086 | 0.4 |
| FL α$_1$AT Pitts C232S P2K | 0.051 ± 0.0028 | 64.82 ± 7.14 | 1,271 |
| FL α$_1$AT Pitts C232S P1'K | 0.17 ± 0.017 | 95.66 ± 13.70 | 563 |
| FL α$_1$AT Pitts C232S P2KP1'K | no inhibition after 4 h | 15.14 ± 1.68 | no thrombin inhibition |

TABLE 2

| Variant | Second-order rate constants of inhibition (mM$^{-1}$·s$^{-1}$) | | Fold inhibition |
|---|---|---|---|
| | Thrombin + heparin | APC + heparin | APC/Thrombin |
| A22 WT PCI | 1310.32 ± 218.72 | 564.47 ± 71.29 | 0.4 |
| A22 P1'K PCI | 0.017 ± 0.0019 | 321.54 ± 31.94 | 18914 |
| A22 P2KP1'K PCI | 0.11 ± 0.040* | 146.38 ± 18.85 | 1331.7 |

TABLE 3

| Variant | Second-order rate constants of inhibition (mM$^{-1}$·s$^{-1}$) | Fold inhibition |
|---|---|---|
| | fXa | APC/fXa |
| A22 WT PCI | 10.31 ± 0.73 | 0.07 |
| A22 P1'K PCI | 0.52 ± 0.079 | 1.7 |
| A22 P2KP1'K PCI | no detectable inhibition | no fXa inhibition |
| FL α$_1$AT Pitts C232S | 41.33 ± 2.36 | 2.6 |
| FL α$_1$AT Pitts C232S P2K | 3.93 ± 0.31 | 16.5 |
| FL α$_1$AT Pitts C232S P1'K | 4.89 ± 0.16 | 19.6 |
| FL α$_1$AT Pitts C232S P2KP1'K | 0.12 ± 0.010 | 126.2 |

TABLE 4

| Variant | Second-order rate constants of inhibition (mM$^{-1}$·s$^{-1}$) | | Inhibition of |
|---|---|---|---|
| | fXIa | APC | APC/fXIa |
| A22 WT PCI | 8.59 ± 0.43 | 0.68 ± 0.032 | 0.08 |
| A22 P2KP1'K PCI | 0.023 ± 0.0052 | 0.28 ± 0.013 | 12.2 |

TABLE 5

| Variant | Second-order rate constants of inhibition (mM$^{-1}$·s$^{-1}$) | | Inhibition of |
|---|---|---|---|
| | Thrombin | APC | APC/Thrombin |
| A22 WT PCI | 28.21 ± 1.51 | 0.68 ± 0.032 | 0.02 |
| A22 P2KP1'K PCI | ~0.03* | 0.28 ± 0.013 | 9.3 |
| A22 D8 PCI (P4QP2RP1'N) | 0.084 ± 0.0016 | 1.00 ± 0.15 | 11.9 |
| A22 4.H11 PCI (P4KP2RP1'H) | 0.021 ± 0.0012 | 0.45 ± 0.15 | 21.4 |
| A22 2.B10 PCI (P4SP2LP1'K) | 0.016 ± 0.00090 | 0.43 ± 0.0086 | 26.9 |
| A22 5.E12 PCI (P4HP2RP1'V) | 0.023 ± 0.0021 | 0.26 ± 0.035 | 11.3 |

TABLE 6

| Variant | Second-order rate constants of inhibition (mM$^{-1}$·s$^{-1}$) | | Inhibition of |
|---|---|---|---|
| | fXIa | APC | APC/fXIa |
| FL α$_1$AT Pitts C232S | 398.88 ± 13.012 | 108.16 ± 7.086 | 0.3 |
| FL α$_1$AT Pitts C232S P2KP1'K | 0.47 ± 0.037 | 15.14 ± 1.68 | 32.2 |

TABLE 7

| | P6 | P5 | P4 | P3 | P2 | P1 | P1• | P2• | P3• | P4• |
|---|---|---|---|---|---|---|---|---|---|---|
| WT | T | I | F | T | F | R | S | A | R | L |
| P2KP1•K | T | I | F | T | K | R | K | A | R | L |
| E7 | T | I | S | T | H | R | R | A | R | L |
| E10 | T | I | R | T | Q | R | V | A | R | L |
| E11 | T | I | T | T | L | R | Y | A | R | L |
| D8 | T | I | Q | T | R | R | N | A | R | L |
| H11 | T | I | A | T | Q | R | Y | A | R | L |

TABLE 8

| | P6 | P5 | P4 | P3 | P2 | P1 | P1• | P2• | P3• | P4• |
|---|---|---|---|---|---|---|---|---|---|---|
| WT | T | I | F | T | F | R | S | A | R | L |
| P2KP1•K | T | I | F | T | K | R | K | A | R | L |
| 2.B10 | T | I | S | T | L | R | K | A | R | L |
| 3.B11 | T | I | F | T | F | R | R | A | R | L |
| 3.C3 | T | I | V | T | R | R | I | A | R | L |
| 3.E8 | T | I | F | T | R | R | K | A | R | L |
| 3.G10 | T | I | C | T | L | R | K | A | R | L |
| 3.G11 | T | I | W | T | W | R | N | A | R | L |
| 3.H11 | T | I | W | T | W | R | N | A | R | L |
| 4.E4 | T | I | K | T | D | R | M | A | R | L |
| 4.F7 | T | I | F | T | V | R | K | A | R | L |
| 4.F10 | T | I | R | T | R | R | I | A | R | L |
| 4.H7 | T | I | G | T | I | R | R | A | R | L |
| 4.H11 | T | I | K | T | R | R | H | A | R | L |
| 5.D2 | T | I | T | T | R | R | V | A | R | L |
| 5.E7 | T | I | L | T | R | R | I | A | R | L |
| 5.E12 | T | I | H | T | R | R | V | A | R | L |

TABLE 9

| | P6 | P5 | P4 | P3 | P2 | P1 | P1• | P2• | P3• | P4• |
|---|---|---|---|---|---|---|---|---|---|---|
| α₁AT WT | L | E | A | I | P | M | S | I | P | P |
| α₁AT Pitts | L | E | A | I | P | R | S | I | P | P |
| P2.G11 | L | E | A | I | K | R | S | I | P | P |
| P2.F10 | L | E | A | I | R | R | S | I | P | P |
| P2.D8 | L | E | A | I | K | R | S | I | P | P |
| P2.G8 | L | E | A | I | R | R | S | I | P | P |
| P2.E7 | L | E | A | I | R | R | S | I | P | P |
| P2.D10 | L | E | A | I | R | R | S | I | P | P |
| P2.G4 | L | E | A | I | R | R | S | I | P | P |
| P2.F4 | L | E | A | I | R | R | S | I | P | P |
| P1'.H8 | L | E | A | I | P | R | E | I | P | P |
| P1'.A11 | L | E | A | I | P | R | R | I | P | P |
| P1'.F10 | L | E | A | I | P | R | E | I | P | P |
| P1'.F9 | L | E | A | I | P | R | K | I | P | P |
| P1'.F4 | L | E | A | I | P | R | E | I | P | P |
| 4.G9 | L | E | A | I | T | R | N | I | P | P |
| 4.G4 | L | E | A | I | Q | R | K | I | P | P |
| 3.E5 | L | E | A | I | R | R | A | I | P | P |
| 3.B6 | L | E | A | I | S | R | R | I | P | P |
| 3.B2 | L | E | A | I | K | R | N | I | P | P |
| 3.A10 | L | E | A | I | T | R | Y | I | P | P |
| 2.H1 | L | E | A | I | R | R | H | I | P | P |
| 2.C6 | L | E | A | I | T | R | R | I | P | P |
| 1.H10 | L | E | A | I | V | R | R | I | P | P |
| 1.B11 | L | E | A | I | R | R | C | I | P | P |
| 1.A12 | L | E | A | I | K | R | H | I | P | P |
| 2.E5 | L | E | A | I | T | R | R | I | P | P |
| 3.G9 | L | E | A | I | Y | R | R | I | P | P |
| 3.F4 | L | E | A | I | A | R | R | I | P | P |
| 3.C9 | L | E | A | I | C | R | K | I | P | p |
| 2.H5 | L | E | A | I | K | R | N | I | P | P |
| 2.E7 | L | E | A | I | W | R | N | I | P | P |
| 1.B2 | L | E | A | I | S | R | R | I | P | P |
| 5.C12 | L | E | A | I | H | R | N | I | P | P |
| 5.A6 | L | E | A | I | R | R | N | I | P | P |
| 4.E1 | L | E | A | I | P | R | K | I | P | P |
| 4.C12 | L | E | A | I | N | R | N | I | P | P |
| 3.F8 | L | E | A | I | T | R | M | I | P | P |
| 3.C10 | L | E | A | I | T | R | H | I | P | P |
| 2.E8 | L | E | A | I | K | R | S | I | P | P |
| 1.H9 | L | E | A | I | T | R | Q | I | P | P |

TABLE 10

| Variant | Second-order rate constants of inhibition (mM⁻¹·s⁻¹) | | Inhibition of APC/thrombin |
|---|---|---|---|
| | Thrombin | APC | |
| FL α₁AT Pitts C232S | 292.76 ± 17.60 | 108.16 ± 7.086 | 0.4 |
| FL α₁AT Pitts C232S P2KP1'K | no inhibition after 4 h | 15.14 ± 1.68 | No thrombin inhibition |
| FL α₁AT Pitts C232S P2R | 0.042 ± 0.0024 | 61.12 ± 6.26 | 1455.2 |
| FL α₁AT Pitts C232S P1'R | 0.68 ± 0.068 | 131.57 ± 13.32 | 193.5 |
| FL α₁AT Pitts C232S P1'E | 0.15 ± 0.015 | 2.99 ± 0.29 | 19.9 |
| FL α₁AT Pitts C232S P2TP1'N | 0.27 ± 0.047 | 62.37 ± 2.46 | 231.0 |
| FL α₁AT Pitts C232S P2TP1'Y | 0.023 ± 0.0014 | 5.70 ± 0.83 | 247.8 |
| FL α₁AT Pitts C232S P2QP1'K | 0.0038 ± 0.0013 | 33.41 ± 6.36 | 8792.1 |
| FL α₁AT Pitts C232S P2KP1'H | no inhibition after 2 h | 28.84 ± 3.05 | No thrombin inhibition |
| FL α₁AT Pitts C232S P2KP1'N | 0.015 ± 0.0026 | 37.80 ± 2.48 | 2520.0 |
| FL α₁AT Pitts C232S P2RP1'C | 0.034 ± 0.0094 | 24.55 ± 2.15 | 722.1 |

TABLE 11

| Variant | PT (s) | aPTT (s) |
|---|---|---|
| Plasma | 27.2 ± 0.8 | 60.3 |
| FL α₁AT Pitts C232S P2K | 27.0 ± 0.5 | 107.2 |
| FL α₁AT Pitts C232S P1'K | 27.1 ± 0.4 | 228.1 |
| FL α₁AT Pitts C232S P2R | 27.8 ± 0.4 | 111.6 |
| FL α₁AT Pitts C232S P1'R | 28.1 ± 0.5 | 287 |
| FL α₁AT Pitts C232S P1'E | 27.2 ± 0.4 | 84 |
| FL α₁AT Pitts C232S P2TP1'N | 29.5 ± 0.9 | >300 |
| FL α₁AT Pitts C232S P2TP1'Y | 28.3 ± 0.8 | 185.4 |
| FL α₁AT Pitts C232S P2QP1'K | 27.9 ± 0.3 | 111.5 |
| FL α₁AT Pitts C232S P2KP1'H | 27.4 ± 0.9 | 77.8 |
| FL α₁AT Pitts C232S P2KP1'N | 27.8 ± 0.3 | 81.9 |
| FL α₁AT Pitts C232S P2RP1'C | 28.5 ± 0.6 | ND |

TABLE 12

| Variant | Second-order rate constants of inhibition (mM⁻¹·s⁻¹) fXa | Inhibition of APC/fXa |
|---|---|---|
| FL α₁AT Pitts C232S | 41.33 ± 2.36 | 2.6 |
| FL α₁AT Pitts C232S P2KP1'K | 0.12 ± 0.010 | 126.2 |
| FL α₁AT Pitts C232S P2R | 4.79 ± 0.58 | 12.8 |
| FL α₁AT Pitts C232S P2QP1'K | 1.082 ± 0.15 | 30.9 |
| FL α₁AT Pitts C232S P2KP1'H | 0.62 ± 0.040 | 46.5 |
| FL α₁AT Pitts C232S P2KP1'N | 0.91 ± 0.13 | 41.5 |

TABLE 13

| Variant | Second-order rate constants of inhibition (mM⁻¹·s⁻¹) | | | aPTT (s) |
|---|---|---|---|---|
| | Thrombin | APC | fXa | |
| FL α₁AT Pitts C232S | 292.76 ± 17.60 | 108.16 ± 7.086 | 41.33 ± 2.36 | >300 (55.0 ± 3.8) |
| FL α₁AT Pitts C232S P2KP1'K | no inhibition after 4 h | 15.14 ± 1.87 | 0.12 ± 0.010 | 62.1 ± 4.2 (55.0 ± 3.8) |
| FL α₁AT Pitts C232S P2RP1'Q | 0.0054 ± 0.0011 | 8.30 ± 1.11 | 0.13 ± 0.0067 | 55.1 ± 2.8 (49.3 ± 2.5) |
| FL α₁AT Pitts C232S P2KP1'Q | 0.0029 ± 0.0015 | 9.00 ± 0.67 | 0.17 ± 0.010 | 53.9 ± 3.0 (49.3 ± 2.5) |

Sequences

SEQ ID NO: 1 Protein C inhibitor (PCI)
SEQ ID NO: 1
```
  1 mqlflllclv llspqgaslh rhhpremkkr vedlhvgatv apssrrdftf dlyralasaa
 61 psqniffspv sismslamls lgagsstkmq ileglglnlq kssekelhrg fqqllqelnq
121 prdgfqlslg nalftdlvvd lqdtfvsamk tlyladtfpt nfrdsagamk qindyvakqt
181 kgkivdllkn ldsnavvimv nyiffkakwe tsfnhkgtqe qdfyvtsetv vrvpmmsred
241 qyhylldrnl scrvvgvpyq gnatalfilp segkmqqven glsektlrkw lkmfkkrqle
301 lylpkfsieg syqlekvlps lgisnvftsh adlsgisnhs niqvsemvhk avvevdesgt
361 raaaatgtif tfrsarlnsq rlvfnrpflm fivdnnilfl gkvnrp
```
Mature protein, including the propeptide, corresponds to residues 20 to 406. Signal sequence corresponds to residues 1-19. Propeptide corresponds to residues 20-25. Residues P4, P2, P1 and P1' of the RCL bold and underlined.

SEQ ID NO: 2 Alpha-1-antichymotrypsin
SEQ ID NO: 2
```
  1 mermlpllal gllaagfcpa vlchpnspld eenltqenqd rgthvdlgla sanvdfafsl
 61 ykqlvlkapd knvifsplsi stalaflslg ahnttlteil kglkfnltet seaeihqsfq
121 hllrtlnqss delqlsmgna mfvkeqlsll drftedakrl ygseafatdf qdsaaakkli
181 ndyvkngtrg kitdlikdld sqtmmvlvny iffkakwemp fdpqdthqsr fylskkkvvm
241 vpmmslhhlt ipyfrdeels ctvvelkytg nasalfilpd qdkmeeveam llpetlkrwr
301 dslefreige lylpkfsisr dynlndillq lgieeaaftsk adlsgitgar nlavsqvvhk
361 avldvfeegt easaatavki tllsalvetr tivrfnrpfl miivptdtqn iffmskvtnp
421 kqa
```
Mature protein corresponds to residues 26 to 423. Residues P4, P2, P1 and P1' of the RCL bold and underlined SEQ ID NO: 3 C1-esterase inhibitor
SEQ ID NO: 3
```
  1 masrltlltl lllllagdra ssnpnatsss sqdpeslqdr gegkvattvi skmlfvepil
 61 evssplpttns ttnsatkita ntttdepttqp tteptttqpti qptqpttqlp tdsptqpttg
121 sfcpgpvtlc sdleshstea vlgdalvdfs lklyhafsam kkvetnmafs pfsiaslltq
181 vllgagentk tnlesilsyp kdftcvhqal kgfttkgvts vsgithspdl airdtfvnas
241 rtlyssspry lsnnsdanle lintwvaknt nnkisrllds lpsdtrlvll naiylsakwk
301 ttfdpkktrm epfhfknsvi kvpmmnskky pvahfidqtl kakvgqlqls hnlslvilvp
361 qnlkhrledm egalspsvfk aimeklemsk fqptlltlpr ikvttsqdml simekleffd
421 fsydlnlcgl tedpdlqvsa mqhqtylelt etgveaaaas aisvartllv fevqqpflfv
481 lwdqqhkfpv fmgrvydpra
```
Mature protein corresponds to residues 23-500. Residues P4, P2, P1 and P1' of the RCL bold and underlined SEQ ID NO: 4 α₂-Antiplasmin
SEQ ID NO: 4
```
  1 mallwgllvl swsclqgpcs vfspvsamep lgrqltsgpn gegvspltll klgngepggq
 61 talksppgvc srdptpegth rlarammaft adlfslvaqt stcpnlilsp lsvalalshl
121 algagnntlq rlqqvlhags gpclphllsr lcqdlgpgaf rlaarmylqk gfpikedfle
181 qseqlfgakp vsltgkqedd laningwvke ategkigefl sglpedtvll llnaihfqgf
241 wrnkfdpslt qrdsfhldeq ftvpvemmqa rtyplrwfll eqpeiqvahf pfknnmsfvv
301 lvpthfewnv sqvlanlswd tlhpplvwer ptkvrlpkly lkhqmdlvat lsqlglgelf
361 qapdlrgise qslvvsgvqh qstlelsevg veaaaatsiamsrmslssfs vnrpflffif
421 edttglplfv gsvrnpnpsa prelkeqqds pgnkdflqsl kgfprgdklf gpdlklvppm
481 eedypqfgsp k
```
Mature protein corresponds to residues 28-491. Residues P4, P2, P1 and P1' of the RCL for inhibition of chymotrypsin in bold, residues for the inhibition of plasmin underlined.

SEQ ID NO: 5 Antithrombin (ATIII)
SEQ ID NO: 5
```
  1 mysnvigtvt sgkrkvylls llligfwdcv tchgspvdic takprdipmn pmciyrspek
 61 katedegseq kipeatnrry welskansrf attfyqhlad skndndnifl splsistafa
121 mtklgacndt lqqlmevfkf dtisektsdq ihfffaklnc rlyrkankss klvsanrlfg
181 dksltfnety qdiselvyga klqpldfken aegsraaink wvsnktegri tdvipseain
241 eltvlvlvnt iyfkglwksk fspentrkel fykadgescs asmmyqegkf ryrrvaegtq
301 vlelpfkgdd itmvlilpkp ekslakveke ltpevlgewl deleemmlvv hmprfriedg
361 fslkeqlgdm glvdlfspek sklpgivaeg rddlyvsdaf hkaflevnee gseaaastav
421 viagrslnpn rvtfkanrpf lvfirevpin tiifmgrvan pcvk
```
Mature protein corresponds to residues 33-464. Residues P4, P2, P1 and P1' of the RCL bold and underlined SEQ ID NO: 6 Heparin cofactor II
SEQ ID NO: 6
```
  1 mkhslnalli fliitsawgg skgpldqlek ggetaqsadp qweglnnknl smplipadfh
 61 kentvtndwi pegeedddyl dlekifsedd dyidivdsls vsptdsdvsa gnilqlfhgk
121 sriqrlniln akfafnlyry lkdqvntfdn ifiapvgist amgmislglk getheqvhsi
181 lhfkdfvnas skyeittihn lfrklthrlf rrnfgytlrs vndlyiqkqf pilldfktkv
241 reyyfaeaqi adfsdpafis ktnnhimklt kglikdalen idpatqmmil nciyfkgswv
301 nkfpvemthn hnfrinerev vkvsmmqtkg nflaandgel dcdilqleyv ggismlivvp
361 hkmsgmktle aqltprvver wqksmtnrtr evllpkfkle knynlveslk lmgirmlfdk
421 ngnmagisdq riaidlfkhq gtitvneegt qattvttvgf mplstqvrft vdrpflfliy
```

```
481 ehrtscllfm grvanpsrs
Mature protein corresponds to residues 20-499. Residues P4, P2, P1
and P1' of the RCL bold and underlined
```

SEQ ID NO: 7 α₁-antitrypsin (α₁AT)

```
                                                          SEQ ID NO: 7
  1 mpssyswgil llaglcclvp vslaedpqgd aaqktdtshn dqdhptfnki tpnlaefafs
 61 lyrdlahqsn stniffspvs iatafamlsl gtkadthdei leglnfnite ipeaqihegf
121 gellrtlnqp dsqlqlttgn gifiseglkl vdkfledvkk lyhseaftvn fgdteeakkq
181 indyvekgtq gkivdlvkel drdtvfalvn yiffkgkwer pfevkdteee dfhvdqvttv
241 kvpmmkrlgm fniqhckkls swvllmkylg nataifflpd egklqhlene lthdiitkfl
301 enedrrsasl hlpklsitgt ydlksvlgql gitkvfsnga dlsgvteeap lklskavhka
361 vltidekgte aagamfleai pmsippevkf nkpfvflmie qntksplfmg kvvnptqk
Mature protein corresponds to residues 25-418. Residues P4, P2, P1
and P1' of the RCL bold and underlined
```

SEQ ID NO: 8 Kallistatin

```
                                                          SEQ ID NO: 8
  1 mhlidyllll lvgllalshg qlhvehdges csnsshqqil etgegspslk iapanadfaf
 61 rfyyliaset pgkniffspl sisaayamls lgacshsrsq ileglgfnit elsesdvhrg
121 fghllhtlnl pghgletrvg salflshnlk flakflndtm avyeaklfht nfydtvgtiq
181 lindhvkket rgkivdlvse lkkdvlmvlv nyiyfkalwe kpfissrttp kdfyvdentt
241 vrvpmmlqdq ehhwylhdry lpcsvlrmdy kgdatvffil pnqgkmreie evltpemlmr
301 wnnllrkrnf ykklelhlpk fsisgsyvld qilprlgftd lfskwadlsg itkqqkleas
361 ksfhkatldv deagteaaaa tsfaikffsa qtnrhilrfn rpflvvifst stqsvlflgk
421 vvdptkp
Mature protein corresponds to residues 21-427. Residues P4, P2, P1
and P1' of the RCL bold and underlined
```

SEQ ID NO: 9 Plasminogen activator inhibitor

```
                                                          SEQ ID NO: 9
  1 mqmspaltcl vlglalvfge gsavhhppsy vahlasdfgv rvfqqvagas kdrnvvfspy
 61 gvasvlamlq lttggetqqq iqaamgfkid dkgmapalrh lykelmgpwn kdeisttdai
121 fvqrdlklvq gfmphffrlf rstvkqvdfs everarfiin dwvkthtkgm isnllgkgav
181 dqltrlylvn alyfngqwkt pfpdssthrr lfhksdgstv svpmmaqtnk fnytefttpd
241 ghyydilelp yhgdtlsmfi aapyekevpl saltnilsaq lishwkgnmt rlprllvlpk
301 fsletevdlr kplenlgmtd mfrqfqadft sisdgeplhv agalqkvkie vnesgtvass
361 stavivsarm apeeiimdrp flfvvrhnpt qtvlfmgqvm ep
Mature protein corresponds to residues 24-402. Residues P4, P2, P1
and P1' of the RCL bold and underlined
```

SEQ ID NO: 10 Protein Z dependent inhibitor

```
                                                          SEQ ID NO: 10
  1 mkvvpsllls vllaqvwlvp glapspgspe tpapqncits rvvqapkeee degeaseeka
 61 seeekawlma srgglakets nfgfsllrki smrhdgnmvf spfgmslamt glmlgatgpt
121 etgikrglhl galkptkpgl lpslfkglre tlsrnlelgl tqgsfafihk dfdvketffn
181 lskryfdtec vpmnfrnasq akrlmnhyin ketrgkipkl fdeinpetkl ilvdyilfkg
241 kwltpfdpvf tevdtfhldk yktikvpmmy gagkfastfd knfrchvlkl pyggnatmlv
301 vlmekmgdhl aledylttdl vetwlrnmkt rnmevffpkf kldqkyemhe llrgmgirri
361 fspfadlsel satgrnlqvs rvlgrtviev dergteavag ilseitaysm ppvikvdrpf
421 hfmiyeetsg mllflgrvvn ptll
Mature protein corresponds to residues 22-444. Residues P4, P2, P1
and P1' of the RCL bold and underlined
```

SEQ ID NO: 11 Protease nexin 1

```
                                                          SEQ ID NO: 11
  1 mnwhlplfil asvtlpsics hfnplsleel gsntgiqvfn qivksrphdn ivisphgias
 61 vlgmlqlgad grtkkglamv mrygvngvgk ilkkinkaiv skknkdivtv anavfvknas
121 eievpfvtrn kdvfqcevrn vnfedpasac dsinawvkne trdmidnlls pdlidgvltr
181 lvlvnavyfk glwksrfqpe ntkkrtfvaa dgksyqvpml aglsvfrags tsapndlwyn
241 fielpyhges ismlialpte sstplsaiip histktidsw msimvpkrvq vilpkftava
301 qtdlkeplkv lgitdmfdss kanfakittg senlhvshil qkakievsed gtkasaatta
361 iliarssppw fivdrpflff irhnptgavl fmgqinkp
Mature protein corresponds to residues 20-398-isoform a.
Residues P4, P2, P1 and P1' of the RCL bold and underlined
```

SEQ ID NO: 12 Modified Serpin in α₁AT scaffold

```
                                                          SEQ ID NO: 12
  1 mpssyswgil llaglcclvp vslaedpqgd aaqktdtshh dqdhptfnki tpnlaefafs
 61 lyrqlahqsn stniffspvs iatafamlsl gtkadthdei leglnfnlte ipeaqihegf
121 qellrtlnqp dsqlqlttgn glflseglkl vdkfledvkk lyhseaftvn fgdteeakkq
181 indyvekgtq gkivdlvkel drdtvfalvn yiffkgkwer pfevkdteee dfhvdqvttv
241 kvpmmkrlgm fniqhckkls swvllmkylg nataifflpd egkighlene lthdiitkfl
301 enedrrsasl hlpklsitgt ydlksvlgql gitkvfsnga dlsgvteeap lklskavhka
```

US 9,982,035 B2

-continued

| Sequences |
|---|
| 361 vltidekgte aagamfleai krkippevkf nkpfvflmie qntksplfmg kvvnptqk<br>Mature protein corresponds to residues 25-418. Residues P4, P2, P1<br>and P1' of the RCL bold and underlined |

The invention claimed is:

1. A serpin comprising the amino acid sequence of residues 25-418 of SEQ ID NO: 12.

2. A pharmaceutical composition comprising the serpin according to claim 1 and a pharmaceutically acceptable excipient.

3. A method of treatment of bleeding or promotion of hemostasis comprising administering the serpin according to claim 1 to an individual in need thereof.

4. A method according to claim 3, wherein the individual has a bleeding disorder.

5. A method according to claim 4, wherein the bleeding disorder is hemophilia.

6. A method according to claim 3 wherein the individual is a trauma patient.

7. A serpin comprising the amino acid sequence of residues 25-418 of SEQ ID NO: 12 with residue E25 substituted for S.

8. A pharmaceutical composition comprising the serpin according to claim 7 and a pharmaceutically acceptable excipient.

9. A method of treatment of bleeding or promotion of hemostasis comprising administering the serpin according to claim 7 to an individual in need thereof.

10. A method according to claim 9, wherein the individual has a bleeding disorder.

11. A method according to claim 10, wherein the bleeding disorder is hemophilia.

12. A method according to claim 9 wherein the individual is a trauma patient.

13. A serpin comprising the amino acid sequence of residues 25-418 of SEQ ID NO: 12 with residue C256 substituted for S.

14. A pharmaceutical composition comprising the serpin according to claim 13 and a pharmaceutically acceptable excipient.

15. A method of treatment of bleeding or promotion of hemostasis comprising administering the serpin according to claim 13 to an individual in need thereof.

16. A method according to claim 15, wherein the individual has a bleeding disorder.

17. A method according to claim 16, wherein the bleeding disorder is hemophilia.

18. A method according to claim 15 wherein the individual is a trauma patient.

19. A serpin comprising the amino acid sequence of residues 25-418 of SEQ ID NO: 12 with residue C256 substituted for S and residue E25 substituted for S.

20. A pharmaceutical composition comprising the serpin according to claim 19 and a pharmaceutically acceptable excipient.

21. A method of treatment of bleeding or promotion of hemostasis comprising administering the serpin according to claim 20 to an individual in need thereof.

22. A method according to claim 21, wherein the individual has a bleeding disorder.

23. A method according to claim 22, wherein the bleeding disorder is hemophilia.

24. A method according to claim 21 wherein the individual is a trauma patient.

* * * * *

SEQUENCE LISTING

<160> NUMBER OF SEQ ID NOS: 93

<210> SEQ ID NO 1
<211> LENGTH: 406
<212> TYPE: PRT
<213> ORGANISM: Homo sapiens

<400> SEQUENCE: 1

```
Met Gln Leu Phe Leu Leu Leu Cys Leu Val Leu Leu Ser Pro Gln Gly
1               5                   10                  15

Ala Ser Leu His Arg His Pro Arg Glu Met Lys Lys Arg Val Glu
            20                  25                  30

Asp Leu His Val Gly Ala Thr Val Ala Pro Ser Ser Arg Arg Asp Phe
        35                  40                  45

Thr Phe Asp Leu Tyr Arg Ala Leu Ala Ser Ala Ala Pro Ser Gln Asn
    50                  55                  60

Ile Phe Phe Ser Pro Val Ser Ile Ser Met Ser Leu Ala Met Leu Ser
65                  70                  75                  80

Leu Gly Ala Gly Ser Ser Thr Lys Met Gln Ile Leu Glu Gly Leu Gly
                85                  90                  95

Leu Asn Leu Gln Lys Ser Ser Glu Lys Glu Leu His Arg Gly Phe Gln
            100                 105                 110

Gln Leu Leu Gln Glu Leu Asn Gln Pro Arg Asp Gly Phe Gln Leu Ser
        115                 120                 125

Leu Gly Asn Ala Leu Phe Thr Asp Leu Val Val Asp Leu Gln Asp Thr
    130                 135                 140

Phe Val Ser Ala Met Lys Thr Leu Tyr Leu Ala Asp Thr Phe Pro Thr
145                 150                 155                 160

Asn Phe Arg Asp Ser Ala Gly Ala Met Lys Gln Ile Asn Asp Tyr Val
                165                 170                 175

Ala Lys Gln Thr Lys Gly Lys Ile Val Asp Leu Leu Lys Asn Leu Asp
            180                 185                 190

Ser Asn Ala Val Val Ile Met Val Asn Tyr Ile Phe Phe Lys Ala Lys
        195                 200                 205

Trp Glu Thr Ser Phe Asn His Lys Gly Thr Gln Glu Gln Asp Phe Tyr
    210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
                245                 250                 255

Val Pro Tyr Gln Gly Asn Ala Thr Ala Leu Phe Ile Leu Pro Ser Glu
            260                 265                 270

Gly Lys Met Gln Gln Val Glu Asn Gly Leu Ser Glu Lys Thr Leu Arg
        275                 280                 285

Lys Trp Leu Lys Met Phe Lys Lys Arg Gln Leu Glu Leu Tyr Leu Pro
    290                 295                 300

Lys Phe Ser Ile Glu Gly Ser Tyr Gln Leu Glu Lys Val Leu Pro Ser
```

```
              305                 310                 315                 320
Leu Gly Ile Ser Asn Val Phe Thr Ser His Ala Asp Leu Ser Gly Ile
                    325                 330                 335

Ser Asn His Ser Asn Ile Gln Val Ser Glu Met Val His Lys Ala Val
                    340                 345                 350

Val Glu Val Asp Glu Ser Gly Thr Arg Ala Ala Ala Thr Gly Thr
                    355                 360                 365

Ile Phe Thr Phe Arg Ser Ala Arg Leu Asn Ser Gln Arg Leu Val Phe
                    370                 375                 380

Asn Arg Pro Phe Leu Met Phe Ile Val Asp Asn Asn Ile Leu Phe Leu
385                 390                 395                 400

Gly Lys Val Asn Arg Pro
                    405

<210> SEQ ID NO 2
<211> LENGTH: 423
<212> TYPE: PRT
<213> ORGANISM: Homo sapiens

<400> SEQUENCE: 2

Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
                100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
        130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
                180                 185                 190

Thr Asp Leu Ile Lys Asp Leu Asp Ser Gln Thr Met Met Val Leu Val
            195                 200                 205

Asn Tyr Ile Phe Phe Lys Ala Lys Trp Glu Met Pro Phe Asp Pro Gln
        210                 215                 220

Asp Thr His Gln Ser Arg Phe Tyr Leu Ser Lys Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
                260                 265                 270
```

```
Ser Ala Leu Phe Ile Leu Pro Asp Gln Asp Lys Met Glu Glu Val Glu
            275                 280                 285

Ala Met Leu Leu Pro Glu Thr Leu Lys Arg Trp Arg Asp Ser Leu Glu
290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
                340                 345                 350

Ala Val Ser Gln Val Val His Lys Ala Val Leu Asp Val Phe Glu Glu
            355                 360                 365

Gly Thr Glu Ala Ser Ala Ala Thr Ala Val Lys Ile Thr Leu Leu Ser
370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
            420

<210> SEQ ID NO 3
<211> LENGTH: 500
<212> TYPE: PRT
<213> ORGANISM: Homo sapiens

<400> SEQUENCE: 3

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220
```

-continued

```
Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
            245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
            275                 280                 285

Leu Leu Asn Ala Ile Tyr Leu Ser Ala Lys Trp Lys Thr Thr Phe Asp
290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
                340                 345                 350

Leu Ser Leu Val Ile Leu Val Pro Gln Asn Leu Lys His Arg Leu Glu
            355                 360                 365

Asp Met Glu Gln Ala Leu Ser Pro Ser Val Phe Lys Ala Ile Met Glu
370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
            435                 440                 445

Leu Thr Glu Thr Gly Val Glu Ala Ala Ala Ser Ala Ile Ser Val
450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 4
<211> LENGTH: 491
<212> TYPE: PRT
<213> ORGANISM: Homo sapiens

<400> SEQUENCE: 4

Met Ala Leu Leu Trp Gly Leu Val Leu Ser Trp Ser Cys Leu Gln
1               5                   10                  15

Gly Pro Cys Ser Val Phe Ser Pro Val Ser Ala Met Glu Pro Leu Gly
            20                  25                  30

Arg Gln Leu Thr Ser Gly Pro Asn Gln Glu Gln Val Ser Pro Leu Thr
            35                  40                  45

Leu Leu Lys Leu Gly Asn Gln Glu Pro Gly Gly Gln Thr Ala Leu Lys
        50                  55                  60

Ser Pro Pro Gly Val Cys Ser Arg Asp Pro Thr Pro Glu Gln Thr His
65                  70                  75                  80

Arg Leu Ala Arg Ala Met Met Ala Phe Thr Ala Asp Leu Phe Ser Leu
```

```
            85                  90                  95
Val Ala Gln Thr Ser Thr Cys Pro Asn Leu Ile Leu Ser Pro Leu Ser
                100                 105                 110

Val Ala Leu Ala Leu Ser His Leu Ala Leu Gly Ala Gln Asn His Thr
                115                 120                 125

Leu Gln Arg Leu Gln Gln Val Leu His Ala Gly Ser Gly Pro Cys Leu
        130                 135                 140

Pro His Leu Leu Ser Arg Leu Cys Gln Asp Leu Gly Pro Gly Ala Phe
145                 150                 155                 160

Arg Leu Ala Ala Arg Met Tyr Leu Gln Lys Gly Phe Pro Ile Lys Glu
                165                 170                 175

Asp Phe Leu Glu Gln Ser Glu Gln Leu Phe Gly Ala Lys Pro Val Ser
                180                 185                 190

Leu Thr Gly Lys Gln Glu Asp Asp Leu Ala Asn Ile Asn Gln Trp Val
            195                 200                 205

Lys Glu Ala Thr Glu Gly Lys Ile Gln Glu Phe Leu Ser Gly Leu Pro
210                 215                 220

Glu Asp Thr Val Leu Leu Leu Asn Ala Ile His Phe Gln Gly Phe
225                 230                 235                 240

Trp Arg Asn Lys Phe Asp Pro Ser Leu Thr Gln Arg Asp Ser Phe His
                245                 250                 255

Leu Asp Glu Gln Phe Thr Val Pro Val Glu Met Met Gln Ala Arg Thr
                260                 265                 270

Tyr Pro Leu Arg Trp Phe Leu Leu Glu Gln Pro Glu Ile Gln Val Ala
            275                 280                 285

His Phe Pro Phe Lys Asn Asn Met Ser Phe Val Val Leu Val Pro Thr
290                 295                 300

His Phe Glu Trp Asn Val Ser Gln Val Leu Ala Asn Leu Ser Trp Asp
305                 310                 315                 320

Thr Leu His Pro Pro Leu Val Trp Glu Arg Pro Thr Lys Val Arg Leu
                325                 330                 335

Pro Lys Leu Tyr Leu Lys His Gln Met Asp Leu Val Ala Thr Leu Ser
                340                 345                 350

Gln Leu Gly Leu Gln Glu Leu Phe Gln Ala Pro Asp Leu Arg Gly Ile
            355                 360                 365

Ser Glu Gln Ser Leu Val Val Ser Gly Val Gln His Gln Ser Thr Leu
        370                 375                 380

Glu Leu Ser Glu Val Gly Val Glu Ala Ala Ala Thr Ser Ile Ala
385                 390                 395                 400

Met Ser Arg Met Ser Leu Ser Ser Phe Ser Val Asn Arg Pro Phe Leu
                405                 410                 415

Phe Phe Ile Phe Glu Asp Thr Thr Gly Leu Pro Leu Phe Val Gly Ser
            420                 425                 430

Val Arg Asn Pro Asn Pro Ser Ala Pro Arg Glu Leu Lys Glu Gln Gln
        435                 440                 445

Asp Ser Pro Gly Asn Lys Asp Phe Leu Gln Ser Leu Lys Gly Phe Pro
    450                 455                 460

Arg Gly Asp Lys Leu Phe Gly Pro Asp Leu Lys Leu Val Pro Pro Met
465                 470                 475                 480

Glu Glu Asp Tyr Pro Gln Phe Gly Ser Pro Lys
                485                 490

<210> SEQ ID NO 5
```

<211> LENGTH: 464
<212> TYPE: PRT
<213> ORGANISM: Homo sapiens

<400> SEQUENCE: 5

```
Met Tyr Ser Asn Val Ile Gly Thr Val Thr Ser Gly Lys Arg Lys Val
1               5                   10                  15

Tyr Leu Leu Ser Leu Leu Ile Gly Phe Trp Asp Cys Val Thr Cys
            20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
            115                 120                 125

Asp Thr Leu Gln Gln Leu Met Glu Val Phe Lys Phe Asp Thr Ile Ser
130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
            195                 200                 205

Glu Asn Ala Glu Gln Ser Arg Ala Ala Ile Asn Lys Trp Val Ser Asn
            210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
            290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
```

```
                385                 390                 395                 400
            His Lys Ala Phe Leu Glu Val Asn Glu Glu Gly Ser Glu Ala Ala Ala
                            405                 410                 415

Ser Thr Ala Val Val Ile Ala Gly Arg Ser Leu Asn Pro Asn Arg Val
                            420                 425                 430

Thr Phe Lys Ala Asn Arg Pro Phe Leu Val Phe Ile Arg Glu Val Pro
                            435                 440                 445

Leu Asn Thr Ile Ile Phe Met Gly Arg Val Ala Asn Pro Cys Val Lys
                            450                 455                 460

<210> SEQ ID NO 6
<211> LENGTH: 499
<212> TYPE: PRT
<213> ORGANISM: Homo sapiens

<400> SEQUENCE: 6

Met Lys His Ser Leu Asn Ala Leu Leu Ile Phe Leu Ile Ile Thr Ser
1               5                   10                  15

Ala Trp Gly Gly Ser Lys Gly Pro Leu Asp Gln Leu Glu Lys Gly Gly
                20                  25                  30

Glu Thr Ala Gln Ser Ala Asp Pro Gln Trp Glu Gln Leu Asn Asn Lys
            35                  40                  45

Asn Leu Ser Met Pro Leu Leu Pro Ala Asp Phe His Lys Glu Asn Thr
        50                  55                  60

Val Thr Asn Asp Trp Ile Pro Glu Gly Glu Glu Asp Asp Asp Tyr Leu
65                  70                  75                  80

Asp Leu Glu Lys Ile Phe Ser Glu Asp Asp Tyr Ile Asp Ile Val
                85                  90                  95

Asp Ser Leu Ser Val Ser Pro Thr Asp Ser Asp Val Ser Ala Gly Asn
                100                 105                 110

Ile Leu Gln Leu Phe His Gly Lys Ser Arg Ile Gln Arg Leu Asn Ile
            115                 120                 125

Leu Asn Ala Lys Phe Ala Phe Asn Leu Tyr Arg Val Leu Lys Asp Gln
        130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
        195                 200                 205

Leu Phe Arg Arg Asn Phe Gly Tyr Thr Leu Arg Ser Val Asn Asp Leu
    210                 215                 220

Tyr Ile Gln Lys Gln Phe Pro Ile Leu Leu Asp Phe Lys Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
        275                 280                 285

Ile Leu Asn Cys Ile Tyr Phe Lys Gly Ser Trp Val Asn Lys Phe Pro
    290                 295                 300
```

```
Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
            325                 330                 335

Asp Gln Glu Leu Asp Cys Asp Ile Leu Gln Leu Glu Tyr Val Gly Gly
        340                 345                 350

Ile Ser Met Leu Ile Val Val Pro His Lys Met Ser Gly Met Lys Thr
    355                 360                 365

Leu Glu Ala Gln Leu Thr Pro Arg Val Val Glu Arg Trp Gln Lys Ser
370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
            405                 410                 415

Leu Phe Asp Lys Asn Gly Asn Met Ala Gly Ile Ser Asp Gln Arg Ile
        420                 425                 430

Ala Ile Asp Leu Phe Lys His Gln Gly Thr Ile Thr Val Asn Glu Glu
    435                 440                 445

Gly Thr Gln Ala Thr Thr Val Thr Thr Val Gly Phe Met Pro Leu Ser
450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
            485                 490                 495

Ser Arg Ser

<210> SEQ ID NO 7
<211> LENGTH: 418
<212> TYPE: PRT
<213> ORGANISM: Homo sapiens

<400> SEQUENCE: 7

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
            85                  90                  95

His Asp Glu Ile Leu Glu Gly Leu Asn Phe Asn Leu Thr Glu Ile Pro
        100                 105                 110

Glu Ala Gln Ile His Glu Gly Phe Gln Glu Leu Leu Arg Thr Leu Asn
    115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
            165                 170                 175
```

```
Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
            210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
            245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
            325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys

<210> SEQ ID NO 8
<211> LENGTH: 427
<212> TYPE: PRT
<213> ORGANISM: Homo sapiens

<400> SEQUENCE: 8

Met His Leu Ile Asp Tyr Leu Leu Leu Leu Val Gly Leu Leu Ala
1               5                   10                  15

Leu Ser His Gly Gln Leu His Val Glu His Asp Gly Glu Ser Cys Ser
            20                  25                  30

Asn Ser Ser His Gln Gln Ile Leu Glu Thr Gly Glu Gly Ser Pro Ser
            35                  40                  45

Leu Lys Ile Ala Pro Ala Asn Ala Asp Phe Ala Phe Arg Phe Tyr Tyr
50                  55                  60

Leu Ile Ala Ser Glu Thr Pro Gly Lys Asn Ile Phe Phe Ser Pro Leu
65                  70                  75                  80

Ser Ile Ser Ala Ala Tyr Ala Met Leu Ser Leu Gly Ala Cys Ser His
            85                  90                  95

Ser Arg Ser Gln Ile Leu Glu Gly Leu Gly Phe Asn Leu Thr Glu Leu
            100                 105                 110

Ser Glu Ser Asp Val His Arg Gly Phe Gln His Leu Leu His Thr Leu
            115                 120                 125
```

Asn Leu Pro Gly His Gly Leu Glu Thr Arg Val Gly Ser Ala Leu Phe
130                 135                 140

Leu Ser His Asn Leu Lys Phe Leu Ala Lys Phe Leu Asn Asp Thr Met
145                 150                 155                 160

Ala Val Tyr Glu Ala Lys Leu Phe His Thr Asn Phe Tyr Asp Thr Val
                165                 170                 175

Gly Thr Ile Gln Leu Ile Asn Asp His Val Lys Lys Glu Thr Arg Gly
                180                 185                 190

Lys Ile Val Asp Leu Val Ser Glu Leu Lys Lys Asp Val Leu Met Val
                195                 200                 205

Leu Val Asn Tyr Ile Tyr Phe Lys Ala Leu Trp Glu Lys Pro Phe Ile
210                 215                 220

Ser Ser Arg Thr Thr Pro Lys Asp Phe Tyr Val Asp Glu Asn Thr Thr
225                 230                 235                 240

Val Arg Val Pro Met Met Leu Gln Asp Gln Glu His His Trp Tyr Leu
                245                 250                 255

His Asp Arg Tyr Leu Pro Cys Ser Val Leu Arg Met Asp Tyr Lys Gly
                260                 265                 270

Asp Ala Thr Val Phe Phe Ile Leu Pro Asn Gln Gly Lys Met Arg Glu
                275                 280                 285

Ile Glu Glu Val Leu Thr Pro Glu Met Leu Met Arg Trp Asn Asn Leu
290                 295                 300

Leu Arg Lys Arg Asn Phe Tyr Lys Lys Leu Glu Leu His Leu Pro Lys
305                 310                 315                 320

Phe Ser Ile Ser Gly Ser Tyr Val Leu Asp Gln Ile Leu Pro Arg Leu
                325                 330                 335

Gly Phe Thr Asp Leu Phe Ser Lys Trp Ala Asp Leu Ser Gly Ile Thr
                340                 345                 350

Lys Gln Gln Lys Leu Glu Ala Ser Lys Ser Phe His Lys Ala Thr Leu
                355                 360                 365

Asp Val Asp Glu Ala Gly Thr Glu Ala Ala Ala Thr Ser Phe Ala
370                 375                 380

Ile Lys Phe Phe Ser Ala Gln Thr Asn Arg His Ile Leu Arg Phe Asn
385                 390                 395                 400

Arg Pro Phe Leu Val Val Ile Phe Ser Thr Ser Thr Gln Ser Val Leu
                405                 410                 415

Phe Leu Gly Lys Val Val Asp Pro Thr Lys Pro
                420                 425

<210> SEQ ID NO 9
<211> LENGTH: 402
<212> TYPE: PRT
<213> ORGANISM: Homo sapiens

<400> SEQUENCE: 9

Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
                20                  25                  30

His Leu Ala Ser Asp Phe Gly Val Arg Val Phe Gln Gln Val Ala Gln
                35                  40                  45

Ala Ser Lys Asp Arg Asn Val Val Phe Ser Pro Tyr Gly Val Ala Ser
            50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 10
<211> LENGTH: 444
<212> TYPE: PRT
<213> ORGANISM: Homo sapiens

<400> SEQUENCE: 10

Met Lys Val Val Pro Ser Leu Leu Leu Ser Val Leu Leu Ala Gln Val
1               5                   10                  15

Trp Leu Val Pro Gly Leu Ala Pro Ser Pro Gln Ser Pro Glu Thr Pro
            20                  25                  30

Ala Pro Gln Asn Gln Thr Ser Arg Val Val Gln Ala Pro Lys Glu Glu
        35                  40                  45

Glu Asp Glu Gln Glu Ala Ser Glu Glu Lys Ala Ser Glu Glu Glu
50                  55                  60

Lys Ala Trp Leu Met Ala Ser Arg Gln Gln Leu Ala Lys Glu Thr Ser
65                  70                  75                  80

Asn Phe Gly Phe Ser Leu Leu Arg Lys Ile Ser Met Arg His Asp Gly
                85                  90                  95

Asn Met Val Phe Ser Pro Phe Gly Met Ser Leu Ala Met Thr Gly Leu
            100                 105                 110

Met Leu Gly Ala Thr Gly Pro Thr Glu Thr Gln Ile Lys Arg Gly Leu
        115                 120                 125

His Leu Gln Ala Leu Lys Pro Thr Lys Pro Gly Leu Leu Pro Ser Leu
    130                 135                 140

Phe Lys Gly Leu Arg Glu Thr Leu Ser Arg Asn Leu Glu Leu Gly Leu
145                 150                 155                 160

Thr Gln Gly Ser Phe Ala Phe Ile His Lys Asp Phe Asp Val Lys Glu
                165                 170                 175

Thr Phe Phe Asn Leu Ser Lys Arg Tyr Phe Asp Thr Glu Cys Val Pro
            180                 185                 190

Met Asn Phe Arg Asn Ala Ser Gln Ala Lys Arg Leu Met Asn His Tyr
        195                 200                 205

Ile Asn Lys Glu Thr Arg Gly Lys Ile Pro Lys Leu Phe Asp Glu Ile
    210                 215                 220

Asn Pro Glu Thr Lys Leu Ile Leu Val Asp Tyr Ile Leu Phe Lys Gly
225                 230                 235                 240

Lys Trp Leu Thr Pro Phe Asp Pro Val Phe Thr Glu Val Asp Thr Phe
                245                 250                 255

His Leu Asp Lys Tyr Lys Thr Ile Lys Val Pro Met Met Tyr Gly Ala
            260                 265                 270

Gly Lys Phe Ala Ser Thr Phe Asp Lys Asn Phe Arg Cys His Val Leu
        275                 280                 285

Lys Leu Pro Tyr Gln Gly Asn Ala Thr Met Leu Val Val Leu Met Glu
    290                 295                 300

Lys Met Gly Asp His Leu Ala Leu Glu Asp Tyr Leu Thr Thr Asp Leu
305                 310                 315                 320

Val Glu Thr Trp Leu Arg Asn Met Lys Thr Arg Asn Met Glu Val Phe
                325                 330                 335

Phe Pro Lys Phe Lys Leu Asp Gln Lys Tyr Glu Met His Glu Leu Leu
            340                 345                 350

Arg Gln Met Gly Ile Arg Arg Ile Phe Ser Pro Phe Ala Asp Leu Ser
        355                 360                 365

Glu Leu Ser Ala Thr Gly Arg Asn Leu Gln Val Ser Arg Val Leu Gln
    370                 375                 380

Arg Thr Val Ile Glu Val Asp Glu Arg Gly Thr Glu Ala Val Ala Gly
385                 390                 395                 400

Ile Leu Ser Glu Ile Thr Ala Tyr Ser Met Pro Val Ile Lys Val
                405                 410                 415

Asp Arg Pro Phe His Phe Met Ile Tyr Glu Glu Thr Ser Gly Met Leu
            420                 425                 430

Leu Phe Leu Gly Arg Val Val Asn Pro Thr Leu Leu
        435                 440

<210> SEQ ID NO 11
<211> LENGTH: 398

<212> TYPE: PRT
<213> ORGANISM: Homo sapiens

<400> SEQUENCE: 11

```
Met Asn Trp His Leu Pro Leu Phe Leu Leu Ala Ser Val Thr Leu Pro
1               5                   10                  15

Ser Ile Cys Ser His Phe Asn Pro Leu Ser Leu Glu Glu Leu Gly Ser
            20                  25                  30

Asn Thr Gly Ile Gln Val Phe Asn Gln Ile Val Lys Ser Arg Pro His
        35                  40                  45

Asp Asn Ile Val Ile Ser Pro His Gly Ile Ala Ser Val Leu Gly Met
    50                  55                  60

Leu Gln Leu Gly Ala Asp Gly Arg Thr Lys Lys Gln Leu Ala Met Val
65                  70                  75                  80

Met Arg Tyr Gly Val Asn Gly Val Gly Lys Ile Leu Lys Lys Ile Asn
                85                  90                  95

Lys Ala Ile Val Ser Lys Lys Asn Lys Asp Ile Val Thr Val Ala Asn
            100                 105                 110

Ala Val Phe Val Lys Asn Ala Ser Glu Ile Glu Val Pro Phe Val Thr
        115                 120                 125

Arg Asn Lys Asp Val Phe Gln Cys Glu Val Arg Asn Val Asn Phe Glu
    130                 135                 140

Asp Pro Ala Ser Ala Cys Asp Ser Ile Asn Ala Trp Val Lys Asn Glu
145                 150                 155                 160

Thr Arg Asp Met Ile Asp Asn Leu Leu Ser Pro Asp Leu Ile Asp Gly
                165                 170                 175

Val Leu Thr Arg Leu Val Leu Val Asn Ala Val Tyr Phe Lys Gly Leu
            180                 185                 190

Trp Lys Ser Arg Phe Gln Pro Glu Asn Thr Lys Lys Arg Thr Phe Val
        195                 200                 205

Ala Ala Asp Gly Lys Ser Tyr Gln Val Pro Met Leu Ala Gln Leu Ser
    210                 215                 220

Val Phe Arg Cys Gly Ser Thr Ser Ala Pro Asn Asp Leu Trp Tyr Asn
225                 230                 235                 240

Phe Ile Glu Leu Pro Tyr His Gly Glu Ser Ile Ser Met Leu Ile Ala
                245                 250                 255

Leu Pro Thr Glu Ser Ser Thr Pro Leu Ser Ala Ile Ile Pro His Ile
            260                 265                 270

Ser Thr Lys Thr Ile Asp Ser Trp Met Ser Ile Met Val Pro Lys Arg
        275                 280                 285

Val Gln Val Ile Leu Pro Lys Phe Thr Ala Val Ala Gln Thr Asp Leu
    290                 295                 300

Lys Glu Pro Leu Lys Val Leu Gly Ile Thr Asp Met Phe Asp Ser Ser
305                 310                 315                 320

Lys Ala Asn Phe Ala Lys Ile Thr Thr Gly Ser Glu Asn Leu His Val
                325                 330                 335

Ser His Ile Leu Gln Lys Ala Lys Ile Glu Val Ser Glu Asp Gly Thr
            340                 345                 350

Lys Ala Ser Ala Ala Thr Thr Ala Ile Leu Ile Ala Arg Ser Ser Pro
        355                 360                 365

Pro Trp Phe Ile Val Asp Arg Pro Phe Leu Phe Ile Arg His Asn
    370                 375                 380

Pro Thr Gly Ala Val Leu Phe Met Gly Gln Ile Asn Lys Pro
385                 390                 395
```

<210> SEQ ID NO 12
<211> LENGTH: 418
<212> TYPE: PRT
<213> ORGANISM: Artificial sequence
<220> FEATURE:
<223> OTHER INFORMATION: Synthetic sequence: Modified Serpin in alpha1AT scaffold

<400> SEQUENCE: 12

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
```

```
                355                 360                 365

Thr Glu Ala Ala Gly Ala Met Phe Leu Glu Ala Ile Lys Arg Lys Ile
        370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 13
<211> LENGTH: 10
<212> TYPE: PRT
<213> ORGANISM: Artificial sequence
<220> FEATURE:
<223> OTHER INFORMATION: Synthetic Affinity Tag

<400> SEQUENCE: 13

Met Arg Gly Ser His His His His His His
1               5                   10

<210> SEQ ID NO 14
<211> LENGTH: 8
<212> TYPE: PRT
<213> ORGANISM: Artificial sequence
<220> FEATURE:
<223> OTHER INFORMATION: Synthetic Affinity Tag

<400> SEQUENCE: 14

Asp Tyr Lys Asp Asp Asp Asp Lys
1               5

<210> SEQ ID NO 15
<211> LENGTH: 15
<212> TYPE: PRT
<213> ORGANISM: Artificial sequence
<220> FEATURE:
<223> OTHER INFORMATION: Synthetic Affinity Tag

<400> SEQUENCE: 15

Lys Glu Thr Ala Ala Ala Lys Phe Glu Arg Gln His Met Asp Ser
1               5                   10                  15

<210> SEQ ID NO 16
<211> LENGTH: 5
<212> TYPE: PRT
<213> ORGANISM: Artificial sequence
<220> FEATURE:
<223> OTHER INFORMATION: Synthetic Affinity Tag

<400> SEQUENCE: 16

Arg Arg Arg Arg Arg
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic Affinity Tag

<400> SEQUENCE: 17

Arg Arg Arg Arg Arg Arg
1               5
```

```
<210> SEQ ID NO 18
<211> LENGTH: 4
<212> TYPE: PRT
<213> ORGANISM: Artificial sequence
<220> FEATURE:
<223> OTHER INFORMATION: Synthetic Affinity Tag

<400> SEQUENCE: 18

His His His His
1

<210> SEQ ID NO 19
<211> LENGTH: 5
<212> TYPE: PRT
<213> ORGANISM: Artificial sequence
<220> FEATURE:
<223> OTHER INFORMATION: Synthetic Affinity Tag

<400> SEQUENCE: 19

His His His His His
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic Affinity Tag

<400> SEQUENCE: 20

His His His His His His
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic Affinity Tag

<400> SEQUENCE: 21

His His His His His His His
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic Affinity Tag

<400> SEQUENCE: 22

His His His His His His His His
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic Affinity Tag

<400> SEQUENCE: 23

His His His His His His His His His
1               5

<210> SEQ ID NO 24
```

```
<211> LENGTH: 10
<212> TYPE: PRT
<213> ORGANISM: Artificial sequence
<220> FEATURE:
<223> OTHER INFORMATION: Synthetic Affinity Tag

<400> SEQUENCE: 24

His His His His His His His His His His
1               5                   10

<210> SEQ ID NO 25
<211> LENGTH: 4
<212> TYPE: PRT
<213> ORGANISM: Artificial sequence
<220> FEATURE:
<223> OTHER INFORMATION: Synthetic Affinity Tag

<400> SEQUENCE: 25

Cys Cys Cys Cys
1

<210> SEQ ID NO 26
<211> LENGTH: 11
<212> TYPE: PRT
<213> ORGANISM: Artificial sequence
<220> FEATURE:
<223> OTHER INFORMATION: Synthetic Affinity Tag

<400> SEQUENCE: 26

Phe Phe Phe Phe Phe Phe Phe Phe Phe Phe Phe
1               5                   10

<210> SEQ ID NO 27
<211> LENGTH: 5
<212> TYPE: PRT
<213> ORGANISM: Artificial sequence
<220> FEATURE:
<223> OTHER INFORMATION: Synthetic Affinity Tag

<400> SEQUENCE: 27

Asp Asp Asp Asp Asp
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic Affinity Tag

<400> SEQUENCE: 28

Asp Asp Asp Asp Asp Asp
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic Affinity Tag

<400> SEQUENCE: 29

Asp Asp Asp Asp Asp Asp Asp
1               5

<210> SEQ ID NO 30
<211> LENGTH: 8
```

```
<212> TYPE: PRT
<213> ORGANISM: Artificial sequence
<220> FEATURE:
<223> OTHER INFORMATION: Synthetic Affinity Tag

<400> SEQUENCE: 30

Asp Asp Asp Asp Asp Asp Asp Asp
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic Affinity Tag

<400> SEQUENCE: 31

Asp Asp Asp Asp Asp Asp Asp Asp Asp
1               5

<210> SEQ ID NO 32
<211> LENGTH: 10
<212> TYPE: PRT
<213> ORGANISM: Artificial sequence
<220> FEATURE:
<223> OTHER INFORMATION: Synthetic Affinity Tag

<400> SEQUENCE: 32

Asp Asp Asp Asp Asp Asp Asp Asp Asp Asp
1               5                   10

<210> SEQ ID NO 33
<211> LENGTH: 11
<212> TYPE: PRT
<213> ORGANISM: Artificial sequence
<220> FEATURE:
<223> OTHER INFORMATION: Synthetic Affinity Tag

<400> SEQUENCE: 33

Asp Asp Asp Asp Asp Asp Asp Asp Asp Asp Asp
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic Affinity Tag

<400> SEQUENCE: 34

Asp Asp Asp Asp Asp Asp Asp Asp Asp Asp Asp Asp
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic Affinity Tag

<400> SEQUENCE: 35

Asp Asp Asp Asp Asp Asp Asp Asp Asp Asp Asp Asp Asp
1               5                   10

<210> SEQ ID NO 36
<211> LENGTH: 14
<212> TYPE: PRT
```

<213> ORGANISM: Artificial sequence
<220> FEATURE:
<223> OTHER INFORMATION: Synthetic Affinity Tag

<400> SEQUENCE: 36

Asp Asp Asp Asp Asp Asp Asp Asp Asp Asp Asp Asp Asp
1               5                   10

<210> SEQ ID NO 37
<211> LENGTH: 15
<212> TYPE: PRT
<213> ORGANISM: Artificial sequence
<220> FEATURE:
<223> OTHER INFORMATION: Synthetic Affinity Tag

<400> SEQUENCE: 37

Asp Asp Asp Asp Asp Asp Asp Asp Asp Asp Asp Asp Asp Asp Asp
1               5                   10                  15

<210> SEQ ID NO 38
<211> LENGTH: 16
<212> TYPE: PRT
<213> ORGANISM: Artificial sequence
<220> FEATURE:
<223> OTHER INFORMATION: Synthetic Affinity Tag

<400> SEQUENCE: 38

Asp Asp Asp Asp Asp Asp Asp Asp Asp Asp Asp Asp Asp Asp Asp Asp
1               5                   10                  15

<210> SEQ ID NO 39
<211> LENGTH: 8
<212> TYPE: PRT
<213> ORGANISM: Artificial sequence
<220> FEATURE:
<223> OTHER INFORMATION: Synthetic Affinity Tag

<400> SEQUENCE: 39

Trp Ser His Pro Gln Phe Glu Lys
1               5

<210> SEQ ID NO 40
<211> LENGTH: 10
<212> TYPE: PRT
<213> ORGANISM: Artificial sequence
<220> FEATURE:
<223> OTHER INFORMATION: Synthetic Affinity Tag

<400> SEQUENCE: 40

Glu Gln Lys Leu Ile Ser Glu Glu Asp Leu
1               5                   10

<210> SEQ ID NO 41
<211> LENGTH: 12
<212> TYPE: PRT
<213> ORGANISM: Artificial sequence
<220> FEATURE:
<223> OTHER INFORMATION: Synthetic Affinity Tag

<400> SEQUENCE: 41

Met Lys Ala Glu Phe Arg Arg Gln Glu Ser Asp Arg
1               5                   10

<210> SEQ ID NO 42
<211> LENGTH: 12
<212> TYPE: PRT
<213> ORGANISM: Artificial sequence

```
<220> FEATURE:
<223> OTHER INFORMATION: Synthetic Affinity Tag

<400> SEQUENCE: 42

Met Arg Asp Ala Leu Asp Arg Leu Asp Arg Leu Ala
1               5                   10

<210> SEQ ID NO 43
<211> LENGTH: 10
<212> TYPE: PRT
<213> ORGANISM: Homo sapiens

<400> SEQUENCE: 43

Thr Ile Phe Thr Phe Arg Ser Ala Arg Leu
1               5                   10

<210> SEQ ID NO 44
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 44

Thr Ile Phe Thr Lys Arg Lys Ala Arg Leu
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 45

Thr Ile Ser Thr His Arg Arg Ala Arg Leu
1               5                   10

<210> SEQ ID NO 46
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 46

Thr Ile Arg Thr Gln Arg Val Ala Arg Leu
1               5                   10

<210> SEQ ID NO 47
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 47

Thr Ile Thr Thr Leu Arg Tyr Ala Arg Leu
1               5                   10

<210> SEQ ID NO 48
<211> LENGTH: 10
<212> TYPE: PRT
<213> ORGANISM: Artificial sequence
<220> FEATURE:
<223> OTHER INFORMATION: Synthetic sequence: RCL sequence of PCI variant
```

```
<400> SEQUENCE: 48

Thr Ile Gln Thr Arg Arg Asn Ala Arg Leu
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 49

Thr Ile Ala Thr Gln Arg Tyr Ala Arg Leu
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 50

Thr Ile Ser Thr Leu Arg Lys Ala Arg Leu
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 51

Thr Ile Phe Thr Phe Arg Arg Ala Arg Leu
1               5                   10

<210> SEQ ID NO 52
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 52

Thr Ile Val Thr Arg Arg Ile Ala Arg Leu
1               5                   10

<210> SEQ ID NO 53
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 53

Thr Ile Phe Thr Arg Arg Lys Ala Arg Leu
1               5                   10

<210> SEQ ID NO 54
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 54
```

Thr Ile Cys Thr Leu Arg Lys Ala Arg Leu
1 5 10

<210> SEQ ID NO 55
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 55

Thr Ile Trp Thr Trp Arg Asn Ala Arg Leu
1 5 10

<210> SEQ ID NO 56
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 56

Thr Ile Lys Thr Asp Arg Met Ala Arg Leu
1 5 10

<210> SEQ ID NO 57
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 57

Thr Ile Phe Thr Val Arg Lys Ala Arg Leu
1 5 10

<210> SEQ ID NO 58
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 58

Thr Ile Arg Thr Arg Arg Ile Ala Arg Leu
1 5 10

<210> SEQ ID NO 59
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 59

Thr Ile Gly Thr Ile Arg Arg Ala Arg Leu
1 5 10

<210> SEQ ID NO 60
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 60

Thr Ile Lys Thr Arg Arg His Ala Arg Leu
1               5                   10

<210> SEQ ID NO 61
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 61

Thr Ile Thr Thr Arg Arg Val Ala Arg Leu
1               5                   10

<210> SEQ ID NO 62
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 62

Thr Ile Leu Thr Arg Arg Ile Ala Arg Leu
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic sequence: RCL sequence of PCI variant

<400> SEQUENCE: 63

Thr Ile His Thr Arg Arg Val Ala Arg Leu
1               5                   10

<210> SEQ ID NO 64
<211> LENGTH: 10
<212> TYPE: PRT
<213> ORGANISM: Homo sapiens

<400> SEQUENCE: 64

Leu Glu Ala Ile Pro Met Ser Ile Pro Pro
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 65

Leu Glu Ala Ile Pro Arg Ser Ile Pro Pro
1               5                   10

<210> SEQ ID NO 66
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 66

Leu Glu Ala Ile Lys Arg Ser Ile Pro Pro

<210> SEQ ID NO 67
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 67

Leu Glu Ala Ile Arg Arg Ser Ile Pro Pro
1               5                   10

<210> SEQ ID NO 68
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 68

Leu Glu Ala Ile Pro Arg Glu Ile Pro Pro
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 69

Leu Glu Ala Ile Pro Arg Arg Ile Pro Pro
1               5                   10

<210> SEQ ID NO 70
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 70

Leu Glu Ala Ile Pro Arg Lys Ile Pro Pro
1               5                   10

<210> SEQ ID NO 71
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 71

Leu Glu Ala Ile Thr Arg Asn Ile Pro Pro
1               5                   10

<210> SEQ ID NO 72
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT variant

<400> SEQUENCE: 72

Leu Glu Ala Ile Gln Arg Lys Ile Pro Pro
1               5                   10

<210> SEQ ID NO 73
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 73

Leu Glu Ala Ile Arg Arg Ala Ile Pro Pro
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 74

Leu Glu Ala Ile Ser Arg Arg Ile Pro Pro
1               5                   10

<210> SEQ ID NO 75
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 75

Leu Glu Ala Ile Lys Arg Asn Ile Pro Pro
1               5                   10

<210> SEQ ID NO 76
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 76

Leu Glu Ala Ile Thr Arg Tyr Ile Pro Pro
1               5                   10

<210> SEQ ID NO 77
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 77

Leu Glu Ala Ile Arg Arg His Ile Pro Pro
1               5                   10

<210> SEQ ID NO 78

```
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 78

Leu Glu Ala Ile Thr Arg Arg Ile Pro Pro
1               5                   10

<210> SEQ ID NO 79
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 79

Leu Glu Ala Ile Val Arg Arg Ile Pro Pro
1               5                   10

<210> SEQ ID NO 80
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 80

Leu Glu Ala Ile Arg Arg Cys Ile Pro Pro
1               5                   10

<210> SEQ ID NO 81
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 81

Leu Glu Ala Ile Lys Arg His Ile Pro Pro
1               5                   10

<210> SEQ ID NO 82
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 82

Leu Glu Ala Ile Tyr Arg Arg Ile Pro Pro
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 83
```

Leu Glu Ala Ile Ala Arg Arg Ile Pro Pro
1               5                   10

<210> SEQ ID NO 84
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 84

Leu Glu Ala Ile Cys Arg Lys Ile Pro Pro
1               5                   10

<210> SEQ ID NO 85
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 85

Leu Glu Ala Ile Trp Arg Asn Ile Pro Pro
1               5                   10

<210> SEQ ID NO 86
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 86

Leu Glu Ala Ile Ser Arg Arg Ile Pro Pro
1               5                   10

<210> SEQ ID NO 87
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 87

Leu Glu Ala Ile His Arg Asn Ile Pro Pro
1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 88

Leu Glu Ala Ile Arg Arg Asn Ile Pro Pro
1               5                   10

<210> SEQ ID NO 89
<211> LENGTH: 10
<212> TYPE: PRT
<213> ORGANISM: Artificial sequence
<220> FEATURE:

```
<223> OTHER INFORMATION: Synthetic sequence: RCL sequence of alpha1 AT
      variant

<400> SEQUENCE: 89

Leu Glu Ala Ile Pro Arg Lys Ile Pro Pro
1               5                   10

<210> SEQ ID NO 90
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 90

Leu Glu Ala Ile Asn Arg Asn Ile Pro Pro
1               5                   10

<210> SEQ ID NO 91
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 91

Leu Glu Ala Ile Thr Arg Met Ile Pro Pro
1               5                   10

<210> SEQ ID NO 92
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 92

Leu Glu Ala Ile Thr Arg His Ile Pro Pro
1               5                   10

<210> SEQ ID NO 93
<211> LENGTH: 10
<212> TYPE: PRT
<213> ORGANISM: Artificial sequence
<220> FEATURE:
<223> OTHER INFORMATION: Synthetic sequence: RCL sequence of alpha1 AT
      variant

<400> SEQUENCE: 93

Leu Glu Ala Ile Thr Arg Gln Ile Pro Pro
1               5                   10
```